(12) United States Patent
Okada et al.

(10) Patent No.: US 9,243,007 B2
(45) Date of Patent: Jan. 26, 2016

(54) ORGANOPOLYSILOXANE, METHOD FOR PRODUCING THE SAME, AND CURABLE RESIN COMPOSITION CONTAINING THE ORGANOPOLYSILOXANE

(75) Inventors: Yuji Okada, Tokyo (JP); Yoshito Kuroda, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/008,611

(22) PCT Filed: Mar. 27, 2012

(86) PCT No.: PCT/JP2012/057969
§ 371 (c)(1),
(2), (4) Date: Oct. 14, 2013

(87) PCT Pub. No.: WO2012/133432
PCT Pub. Date: Oct. 4, 2012

(65) Prior Publication Data
US 2014/0114021 A1    Apr. 24, 2014

(30) Foreign Application Priority Data
Mar. 30, 2011 (WO) .................. PCT/JP2011/058115

(51) Int. Cl.
| C08G 77/08 | (2006.01) |
| C07F 7/21 | (2006.01) |
| C09D 11/00 | (2014.01) |
| C08F 299/08 | (2006.01) |
| C08G 77/20 | (2006.01) |
| C08G 77/44 | (2006.01) |
| C08G 77/50 | (2006.01) |
| C09D 11/101 | (2014.01) |
| C09D 183/14 | (2006.01) |
| C08G 77/12 | (2006.01) |
| C09J 183/14 | (2006.01) |
| C08F 130/08 | (2006.01) |
| C08K 3/20 | (2006.01) |
| C09D 183/06 | (2006.01) |

(Continued)

(52) U.S. Cl.
CPC .................. *C07F 7/21* (2013.01); *C08F 130/08* (2013.01); *C08F 299/08* (2013.01); *C08G 77/12* (2013.01); *C08G 77/20* (2013.01); *C08G 77/44* (2013.01); *C08G 77/50* (2013.01); *C08K 3/20* (2013.01); *C09D 11/00* (2013.01); *C09D 11/101* (2013.01); *C09D 183/06* (2013.01); *C09D 183/14* (2013.01); *C09J 183/14* (2013.01); *C08L 83/14* (2013.01); *H01L 33/56* (2013.01)

(58) Field of Classification Search
CPC ........ C08G 77/12; C08G 77/20; C08G 77/50; C08L 83/00; C09D 11/00; C09D 11/01; C09D 11/102; C09D 183/14
See application file for complete search history.

(56) References Cited

U.S. PATENT DOCUMENTS

| 2,848,328 A | 8/1958 | Hepher |
| 2,852,379 A | 9/1958 | Hepher et al. |
| 2,940,852 A | 6/1960 | Herrick, Jr. et al. |

(Continued)

FOREIGN PATENT DOCUMENTS

| EP | 126712 B1 | 12/1986 |
| EP | 109851 B1 | 9/1993 |

(Continued)

OTHER PUBLICATIONS

Extended European Search Report issued in related European Patent Application No. 12763457.4 dated Jul. 17, 2014.

(Continued)

*Primary Examiner* — Margaret Moore
(74) *Attorney, Agent, or Firm* — Morgan, Lewis & Bockius LLP

(57) ABSTRACT

The present invention provides organopolysiloxane comprising one or more unsaturated bond-containing group(s) in one molecule and having constitutional units F1, M1, and T in any combination of
(i) F1 and M1,
(ii) F1 and T, and
(iii) F1, M1, and T:

F1:

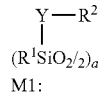

(1)

M1:

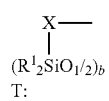

(2)

T:

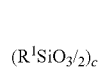

(3)

wherein $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group; $R^2$ represents an unsaturated bond-containing group having 2 to 10 carbon atoms; X represents a divalent hydrocarbon group having 2 to 10 carbon atoms; Y represents a divalent hydrocarbon group having 2 to 10 carbon atoms; and a, b, and c each independently represent an integer of 1 or larger, wherein F1 represents a unit constituting cyclic organopolysiloxane.

27 Claims, No Drawings

(51) Int. Cl.
  *C08L 83/14* (2006.01)
  *H01L 33/56* (2010.01)

(56) References Cited

U.S. PATENT DOCUMENTS

| | | | |
|---|---|---|---|
| 3,567,453 | A | 3/1971 | Borden |
| 4,026,705 | A | 5/1977 | Crivello et al. |
| 4,172,946 | A | 10/1979 | Maki |
| 4,954,414 | A | 9/1990 | Adair et al. |
| 4,988,788 | A | 1/1991 | Takarada |
| 5,545,837 | A | 8/1996 | Kobayashi |
| 6,566,413 | B1 * | 5/2003 | Weinmann et al. ............. 522/71 |
| 6,624,236 | B1 * | 9/2003 | Bissinger et al. ............. 524/588 |
| 2004/0249103 | A1 | 12/2004 | Morimoto et al. |
| 2005/0009982 | A1 | 1/2005 | Inagaki et al. |
| 2005/0256286 | A1 | 11/2005 | Asch et al. |
| 2006/0111491 | A1 * | 5/2006 | Asch et al. .................... 524/261 |
| 2006/0116500 | A1 * | 6/2006 | Chapman et al. .............. 528/15 |
| 2006/0222999 | A1 | 10/2006 | Miyazaki et al. |
| 2009/0258992 | A1 | 10/2009 | Yamamoto et al. |
| 2010/0120975 | A1 | 5/2010 | Kuroda et al. |
| 2010/0179283 | A1 | 7/2010 | Sueyoshi et al. |
| 2010/0311919 | A1 | 12/2010 | Ono et al. |

FOREIGN PATENT DOCUMENTS

| | | | |
|---|---|---|---|
| EP | 675152 | A2 | 10/1995 |
| JP | S36-022062 | B | 11/1961 |
| JP | S37-013109 | B | 9/1962 |
| JP | S38-018015 | B | 9/1963 |
| JP | S43-023684 | B | 10/1968 |
| JP | S44-006413 | B | 3/1969 |
| JP | S45-009610 | B | 4/1970 |
| JP | S47-001604 | B | 1/1972 |
| JP | S55-039162 | B | 10/1980 |
| JP | S58-501291 | A | 8/1983 |
| JP | S59-001281 | B2 | 1/1984 |
| JP | S59-001504 | A | 1/1984 |
| JP | S59-014023 | A | 1/1984 |
| JP | S59-107344 | A | 6/1984 |
| JP | S59-142205 | A | 8/1984 |
| JP | S60-060104 | A | 4/1985 |
| JP | S61-009621 | B | 3/1986 |
| JP | S61-151197 | A | 7/1986 |
| JP | S61-243807 | A | 10/1986 |
| JP | S63-168469 | A | 7/1988 |
| JP | H01-054440 | A | 3/1989 |
| JP | H02-182701 | A | 7/1990 |
| JP | H03-209477 | A | 9/1991 |
| JP | H06-213861 | A | 8/1994 |
| JP | H06-255347 | A | 9/1994 |
| JP | H06-298911 | A | 10/1994 |
| JP | H07-268100 | A | 10/1995 |
| JP | H07-309950 | A | 11/1995 |
| JP | H09-328634 | A | 12/1997 |
| JP | H10-182826 | A | 7/1998 |
| JP | 2004-331647 | A | 11/2004 |
| JP | 2005-523980 | A | 8/2005 |
| JP | 2005-529989 | A | 10/2005 |
| JP | 2006-022207 | A | 1/2006 |
| JP | 2008-131009 | A | 6/2008 |
| JP | 2008-201851 | A | 9/2008 |
| JP | 2008-274185 | A | 11/2008 |
| JP | 4235698 | B2 | 3/2009 |
| JP | 2010-001358 | A | 1/2010 |
| TW | 200906916 | A | 4/1997 |
| WO | 83/01777 | A1 | 5/1983 |
| WO | 2003/024870 | A1 | 3/2003 |
| WO | 2007/046399 | A1 | 4/2007 |
| WO | 2008/133108 | A1 | 11/2008 |
| WO | 2008/133227 | A1 | 11/2008 |
| WO | 2008/133229 | A1 | 11/2008 |
| WO | 2009/099099 | A1 | 8/2009 |

OTHER PUBLICATIONS

Crivello et al., "Diaryliodonium Salts. A New Class of Photoinitiators for Cationic Polymerization," Macromolecules, 10: 1307-1315 (1977).

International Search Report issued in corresponding International Patent Application No. PCT/JP2012/057969 dated Jul. 10, 2012.

* cited by examiner

ORGANOPOLYSILOXANE, METHOD FOR PRODUCING THE SAME, AND CURABLE RESIN COMPOSITION CONTAINING THE ORGANOPOLYSILOXANE

TECHNICAL FIELD

The present invention relates to organopolysiloxane, a method for producing the same, and a curable resin composition containing the organopolysiloxane.

BACKGROUND ART

Epoxy resin compositions containing acid anhydride curing agents have heretofore been known to form transparent cured products that are suitable as sealing materials for optical semiconductor devices such as light-emitting diodes and photodiodes.

For example, epoxy resin compositions composed mainly of an epoxy resin having an organic resin skeleton, such as bisphenol A epoxy resin, bisphenol F epoxy resin, or (3',4'-epoxycyclohexyl)methyl-3,4-epoxycyclohexane carboxylate, are used in the field of optical semiconductor devices.

The recent advance of the performance of optical semiconductors, however, has required sealing materials for optical semiconductor devices to have more excellent heat resistance, light resistance, and the like. In this respect, the conventionally known epoxy resin compositions have failed to produce sufficient properties.

In consideration of this problem, proposals have heretofore been made on resin compositions for use in various optical semiconductors.

For example, a thermosetting resin composition for use in optical semiconductors which is obtained by curing a particular silicone composition through hydrosilylation reaction has been proposed (see e.g., Patent Document 1).

A technique of applying a particular silicone composition having improved hardness to use in optical semiconductors has also been proposed (see e.g., Patent Document 2).

A composition for use in optical semiconductors containing organopolysiloxane having a particular structure has further been proposed (see e.g., Patent Document 3).

In addition, a technique of applying a methacryloxy group-containing silicone composition to use in optical semiconductors has been proposed (see e.g., Patent Document 4).

In addition, a technique of using an alicyclic epoxy compound and a vinyl ether compound in combination has been proposed as a technique of applying an epoxy resin composition to photosensitive coating materials, inks, and the like (see e.g., Patent Documents 5 and 6).

Furthermore, a technique of controlling the mechanical properties of a cured product by allowing a material containing an epoxy compound and a vinyl ether compound in combination to further contain a particular phenol resin has been proposed (see e.g., Patent Document 7).

PATENT DOCUMENT

Patent Document 1: Japanese Patent Laid-Open No. 2010-1358
Patent Document 2: Japanese Patent Laid-Open No. 2008-274185
Patent Document 3: Japanese Patent Laid-Open No. 2008-201851
Patent Document 4: Japanese Patent Laid-Open No. 2008-131009
Patent Document 5: Japanese Patent Laid-Open No. 6-298911
Patent Document 6: Japanese Patent Laid-Open No. 9-328634
Patent Document 7: Japanese Patent No. 4235698

SUMMARY OF THE INVENTION

Problems to be Solved by the Invention

The previously proposed techniques, however, have problems as shown below.

The thermosetting resin composition proposed in Patent Document 1 is excellent in thermal yellowing resistance or light resistance, but yields a cured product that is prone to flaws and difficult to handle due to its low hardness. This thermosetting resin composition also produces low gas barrier or adhesion to a base material and thus, cannot be used preferably in sealing materials for optical semiconductors.

The silicone composition proposed in Patent Document 2 employs a phenyl group for enhancing its hardness. The phenyl group, however, is responsible for reduction in thermal yellowing resistance or light resistance. Thus, this silicone composition cannot be used preferably in sealing materials for optical semiconductors.

The composition proposed in Patent Document 3 is excellent in hardness, adhesion, and gas barrier. Isocyanurate serving as the basic skeleton of this composition, however, is responsible for reduction in thermal yellowing resistance or light resistance. Thus, this composition may fall short of a satisfactory level for use in sealing materials for optical semiconductors.

The silicone composition proposed in Patent Document 4 is excellent in thermal yellowing resistance or light resistance, but lacks, in its molecular structure, a site that can relieve stress. Thus, the resulting cured product becomes cracked under environmental change test such as a heat and cold shock test. This means that the resin used in an optical semiconductor becomes cracked by repetitive switch-on/off, leading to disconnection troubles. Also, this silicon composition falls short of a satisfactory level in terms of gas barrier or adhesion to a base material.

The materials proposed in Patent Documents 5 to 7 are excellent in gas barrier and adhesion. Still, all of these materials are epoxy resin compositions prone to yellowing and thus, fall short of a satisfactory level in terms of thermal yellowing resistance or light resistance.

As mentioned above, the previously proposed resin compositions have failed to yield cured products that fully satisfy a good balance among hardness, gas barrier, thermal yellowing resistance, light resistance, heat and cold shock resistance, and adhesion to a base material, at a level required for use in optical semiconductors or in the fields of coating materials, etc.

An object of the present invention is to provide organopolysiloxane capable of forming a cured product that fully satisfies a good balance among hardness, gas barrier, thermal yellowing resistance, light resistance, heat and cold shock resistance, and adhesion to a base material, at a level required particularly for use in optical semiconductors, a method for producing the same, and a curable resin composition containing the organopolysiloxane, and to further provide a die bonding material for optical semiconductors, a coating material, a curable resin composition for nanoimprint, and an ink that require these properties.

Means for Solving the Problems

The present inventors have conducted diligent studies to attain the object and consequently completed the present invention by finding that the object can be attained by a curable resin composition containing organopolysiloxane having a particular structure.

Specifically, the present invention is as follows:

[1]

Organopolysiloxane comprising one or more unsaturated bond-containing group(s) in one molecule and having constitutional units F1, M1, and T in any combination of (i) F1 and M1, (ii) F1 and T, and (iii) F1, M1, and T, wherein the constitutional units F1, M1, and T are represented by the following general formulas (1), (2), and (3), respectively:

F1:

   (1)

M1:

   (2)

T:

   (3)

In the general formulas (1) to (3), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^2$ represents an unsaturated bond-containing group having 2 to 10 carbon atoms;

X represents a divalent hydrocarbon group having 2 to 10 carbon atoms;

Y represents a divalent hydrocarbon group having 2 to 10 carbon atoms; and a, b, and c each independently represent an integer of 1 or larger, wherein F1 represents a unit constituting cyclic organopolysiloxane.

[2]

The organopolysiloxane according to [1], wherein a, b, and c in the general formulas (1) to (3) satisfy the following formula (I):

$$0.1 \leq a/(b+c) \leq 5 \quad (I).$$

[3]

The organopolysiloxane according to [1] or [2], wherein $R^2$ in the constitutional unit F1 represented by the general formula (1) is an acryloxy group or a methacryloxy group.

[4]

The organopolysiloxane according to any one of [1] to [3], wherein the organopolysiloxane has any of constitutional units D1, D2, and D3 represented by the following general formulas (4), (5), and (6), respectively:

D1: $(R^1{}_2SiO_{2/2})$   (4)

D2:

   (5)

D3:

   (6)

In the general formulas (4) to (6), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group; and X represents a divalent hydrocarbon group having 2 to 10 carbon atoms, wherein D1 and D2 each represent a unit constituting cyclic organopolysiloxane, and D3 represents a unit constituting chain organopolysiloxane.

[5]

The organopolysiloxane according to any one of [1] to [4], wherein the organopolysiloxane contains a constitutional unit S represented by the following general formula (7), wherein the content of the constitutional unit represented by the general formula (7) satisfies the following formula (II) with respect to the content of the constitutional unit F1 represented by the general formula (1):

$$d/a \leq 0.1 \quad (II)$$

s: $(R^1HSiO_{2/2})_d$   (7)

In the general formula (7), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group, wherein the constitutional unit S represents a unit constituting cyclic or chain organopolysiloxane.

[7]

The organopolysiloxane according to any one of [1] to [5], wherein the organopolysiloxane contains only the constitutional unit F1 represented by the general formula (1) as a constitutional unit containing the $R^2$ moiety.

The organopolysiloxane according to any one of [1] to [5], wherein the organopolysiloxane contains the constitutional unit F1 represented by the general formula (1) and a constitutional unit F2 represented by the following general formula (8) as constitutional units containing the $R^2$ moiety, provided that $R^{21}$ in the following formula (8) is included in the $R^2$ moiety:

F2:

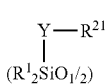   (8)

In the general formula (8), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^{21}$ represents an acryloxy group or a methacryloxy group; and

Y represents a divalent hydrocarbon group having 2 to 10 carbon atoms, wherein

F2 represents a unit constituting chain organopolysiloxane.

[8]

The organopolysiloxane according to any one of [1] to [7], further containing 0.1 to 100 parts by mass of cyclic organopolysiloxane represented by the general formula (9) based on 100 parts by mass of the organopolysiloxane according to any one of [1] to [7]:

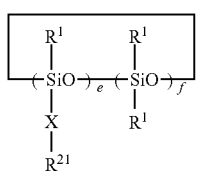
(9)

In the general formula (9), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^{21}$ represents an acryloxy group or a methacryloxy group;

X represents a divalent hydrocarbon group having 2 to 10 carbon atoms;

e represents an integer of 1 or larger;

f represents an integer of 0 or larger; and e+f represents an integer of 3 to 20.

[9]

The organopolysiloxane according to any one of [1] to [8], further containing 0.01 to 1000 parts by mass of a compound represented by the following general formula (10) based on 100 parts by mass of the organopolysiloxane according to any one of [1] to [8]:

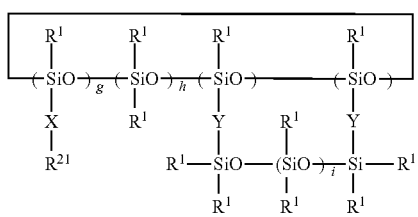
(10)

In the general formula (10), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^{21}$ represents an acryloxy group or a methacryloxy group;

X represents a divalent hydrocarbon group having 2 to 10 carbon atoms;

g represents an integer of 1 or larger;

h represents an integer of 0 or larger; and i represents an integer of 0 to 20.

[10]

The organopolysiloxane according to any one of [1] to [9], wherein the organopolysiloxane contains cyclic organopolysiloxane represented by the following general formula (9) and a compound represented by the following general formula (10):

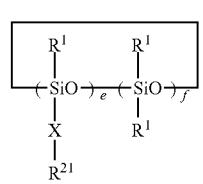
(9)

In the general formula (9), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^{21}$ represents an acryloxy group or a methacryloxy group;

X represents a divalent hydrocarbon group having 2 to 10 carbon atoms;

e represents an integer of 1 or larger;

f represents an integer of 0 or larger; and e+f represents an integer of 3 to 20, and

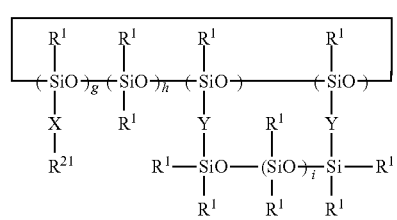
(10)

In the general formula (10), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^{21}$ represents an acryloxy group or a methacryloxy group;

X represents a divalent hydrocarbon group having 2 to 10 carbon atoms;

g represents an integer of 1 or larger;

h represents an integer of 0 or larger; and i represents an integer of 0 to 20, wherein a ratio ([WB]/[WA]) of a content [WB] of the compound represented by the general formula (10) to a content [WA] of the compound represented by the general formula (9) is 0.1 or larger and 20.0 or smaller, the ratio being calculated according to the following formula (III) from peak intensity obtained in measurement by matrix-assisted laser desorption/ionization time-of-flight mass spectrometry:

$$[WB]/[WA] = \frac{\text{Intensity of a peak corresponding to the total sum of the mass of the structure of the general formula (10) and the mass 23 of sodium}}{\text{Intensity of a peak corresponding to the total sum of the mass of the structure of the general formula (9) and the mass 23 of sodium}} \quad (\text{III})$$

[11]

The organopolysiloxane according to any one of [1] to [10], wherein $R^1$ is an alkyl group having 1 to 10 carbon atoms.

[12]

The organopolysiloxane according to any one of [1] to [11], wherein $R^1$ is a methyl group.

[13]

The organopolysiloxane according to any one of [1] to [12], wherein $R^2$ comprises an acryloxy group or a methacryloxy group, wherein the acryloxy group or the methacryloxy group has a functional group equivalent weight of 210 to 2100 g/mol.

[14]

The organopolysiloxane according to any one of [1] to [13], wherein the organopolysiloxane has a weight-average molecular weight of 700 to 5000000 and a viscosity of 50 to 1000000 mPa·s at 25° C.

[15]

A method for producing organopolysiloxane according to any one of [1] to [14], comprising the step of performing the addition reaction of hydrogen polysiloxane (a1) represented by the following general formula (11):

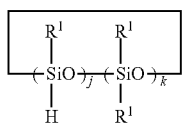

(11)

In the general formula (11), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group; j represents an integer of 1 or larger; k represents an integer of 0 or larger; and j+k represents an integer of 3 to 20, optional hydrogen polysiloxane (a2) having one or more hydrogen atom(s) directly bonded to silicon atom(s), i) vinyl group-containing organopolysiloxane (b1) having two or more vinyl groups directly bonded to silicon atoms, or polysiloxane (b2) having two or more hydroxy groups directly bonded to silicon atoms, and ii) an organic compound (c) having two or more unsaturated bonds in one molecule in the presence of a hydrosilylation reaction catalyst (d).

[16]

The method for producing organopolysiloxane according to [15], wherein the step of performing the addition reaction comprises the steps of:

preparing a reaction solution containing the hydrogen polysiloxane (a1) represented by the general formula (11), and the optional hydrogen polysiloxane (a2) having one or more hydrogen atom(s) directly bonded to silicon atom(s); and the vinyl group-containing organopolysiloxane (b1) having two or more vinyl groups directly bonded to silicon atoms, and the organic compound (c) having two or more unsaturated bonds in one molecule; or the polysiloxane (b2) having two or more hydroxy groups directly bonded to silicon atoms, and the organic compound (c) having two or more unsaturated bonds in one molecule; and adding the hydrosilylation reaction catalyst (d) to the reaction solution.

[17]

The method for producing organopolysiloxane according to [15], wherein the step of performing the addition reaction comprises, in order, the steps of:

preparing a reaction solution containing the hydrogen polysiloxane (a1) represented by the general formula (11), the optional hydrogen polysiloxane (a2) having one or more hydrogen atom(s) directly bonded to silicon atom(s), and the organic compound (c) having two or more unsaturated bonds in one molecule;

adding the hydrosilylation reaction catalyst (d) to the reaction solution to form an adduct of the hydrogen polysiloxane (a1) represented by the general formula (11), the optional hydrogen polysiloxane (a2) having one or more hydrogen atom(s) directly bonded to silicon atom(s), and the organic compound (c) having two or more unsaturated bonds in one molecule; and adding, to the reaction solution, the vinyl group-containing diorganopolysiloxane (b1) having two or more vinyl groups directly bonded to silicon atoms or the polysiloxane (b2) having two or more hydroxy groups directly bonded to silicon atoms.

[18]

A curable resin composition containing 100 parts by mass of organopolysiloxane according to any one of [1] to [14], and 0.5 to 10 parts by mass of a thermal radical generator.

[19]

A curable resin composition containing 100 parts by mass of organopolysiloxane according to any one of [1] to [14], and 0.5 to 20 parts by mass of a photo-radical generator.

[20]

The curable resin composition according to [18] or [19], further containing 0.1 to 10 parts by mass of a silane coupling agent based on 100 parts by mass of the organopolysiloxane according to any one of [1] to [14].

[21]

The curable resin composition according to any one of [18] to [20], further containing 0.001 parts by mass or less of a hydrosilylation reaction catalyst (d) based on 100 parts by mass of the organopolysiloxane according to any one of [1] to [14].

[22]

The curable resin composition according to any one of [18] to [21], further containing 0.1 to 500 parts by mass of an inorganic oxide based on 100 parts by mass of the organopolysiloxane according to any one of [1] to [14].

[23]

A sealing material for optical semiconductors, comprising a curable resin composition according to any one of [18] to [22].

[24]

A die bonding material for optical semiconductors, comprising a curable resin composition according to any one of [18] to [22].

[25]

A coating material comprising a curable resin composition according to any one of [18] to [22].

[26]

A curable resin composition for nanoimprint, comprising a curable resin composition according to any one of [18] to [22].

[27]

An ink comprising a curable resin composition according to any one of [18] to [22] and a colorant.

[28]

An optical semiconductor package obtained by molding a sealing material for optical semiconductors according to [23].

Advantageous Effects of the Invention

The present invention can provide organopolysiloxane capable of forming a cured product that fully satisfies a good balance among hardness, gas barrier, thermal yellowing resistance, light resistance, heat and cold shock resistance, and adhesion to a base material, at a level required for use in optical semiconductors, and a curable resin composition containing the organopolysiloxane.

The present invention can further provide a sealing material for optical semiconductors, a die bonding material for optical semiconductors, a coating material, a curable resin composition for nanoimprint, and a material useful in the field of inks, which have these properties, and an optical semiconductor package obtained by molding the sealing material for optical semiconductors.

MODES FOR CARRYING OUT THE INVENTION

Hereinafter, the mode for carrying out the present invention (hereinafter, referred to as the "present embodiment") will be described in detail.

The present invention is not limited by the description below, and various changes can be made without departing from the spirit of the present invention.

[Organopolysiloxane]

The organopolysiloxane of the present embodiment is organopolysiloxane comprising one or more unsaturated bond-containing group(s) in one molecule and having constitutional units F1, M1, and T in any combination of (i) F1 and M1,
(ii) F1 and T, and
(iii) F1, M1, and T, wherein the constitutional units F1, M1, and T are represented by the following general formulas (1), (2), and (3), respectively:

F1:

(1)

M1:

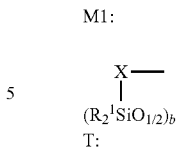

(2)

T:

(3)

$(R^1SiO_{3/2})_c$

In the general formulas (1) to (3), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^2$ represents an unsaturated bond-containing group having 2 to 10 carbon atoms;

X represents a divalent hydrocarbon group having 2 to 10 carbon atoms;

Y represents a divalent hydrocarbon group having 2 to 10 carbon atoms; and a, b, and c each independently represent an integer of 1 or larger.

In this context, F1 represents a unit constituting cyclic organopolysiloxane.

From the viewpoint of light resistance, the organopolysiloxane of the present embodiment is preferably organopolysiloxane having any of constitutional units D1, D2, and D3 represented by the following general formulas (4), (5), and (6), respectively:

D1:

(4)

$(R^1{}_2SiO_{2/2})$

D2:

(5)

D3:

(6)

$(R^1{}_2SiO_{2/2})$

In the general formulas (4) to (6), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group; and X represents a divalent hydrocarbon group having 2 to 10 carbon atoms.

In this context, D1 and D2 each represent a unit constituting cyclic organopolysiloxane, and D3 represents a unit constituting chain organopolysiloxane.

The organopolysiloxane of the present embodiment is preferably organopolysiloxane containing a constitutional unit S represented by the general formula (7) shown below, wherein the content of the constitutional unit S represented by the general formula (7) satisfies the following formula (II) with respect to the content of the constitutional unit F1 represented by the general formula (1):

$d/a \leq 0.1$ (II).

Organopolysiloxane containing a larger amount of the constitutional unit S represented by the general formula (7)

shown below may be gelled through the reaction between SiH and the unsaturated bond during solvent evaporation or during storage. Thus, the content of the constitutional unit S preferably satisfies the formula (II) from the viewpoint of the stable productivity or storage stability of a product.

$$s: (R^1HSiO_{2/2})_d \tag{7}$$

In the general formula (7), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group.

The constitutional unit S represents a unit constituting cyclic or chain organopolysiloxane.

From the viewpoint of the hardness of a cured product, the organopolysiloxane of the present embodiment is preferably organopolysiloxane containing only the constitutional unit F1 represented by the general formula (1) as a constitutional unit containing the $R^2$ moiety. This is because such organopolysiloxane containing only the constitutional unit F1 results in a cured product having a high crosslink density.

In this context, the "constitutional unit containing the $R^2$ moiety" also includes $R^{21}$ (subordinate concept of $R^2$)-containing constitutional units represented by the general formulas (8) to (10) shown below. Specifically, the phrase "containing only the constitutional unit F1 represented by the general formula (1) as a constitutional unit containing the $R^2$ moiety" means "having the constitutional unit F1 represented by the general formula (1), but being free from the $R^{21}$-containing constitutional units represented by the general formulas (8) to (10) shown below".

From the viewpoint of handleability resulting from the low viscosity of a curable resin composition containing the organopolysiloxane, the organopolysiloxane of the present embodiment is preferably organopolysiloxane containing the constitutional unit F1 represented by the general formula (1) and the constitutional unit F2 represented by the general formula (8) shown below.

This is because the replacement of up to half of tetrafunctional SiH moieties with bifunctional SiH moieties can suppress the formation of the cross-linked structure of siloxane and can reduce the viscosity.

F2:

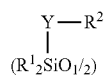

(8)

In the general formula (8), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group; $R^{21}$ represents an acryloxy group or a methacryloxy group; and Y represents a divalent hydrocarbon group having 2 to 10 carbon atoms. In this context, F2 represents a unit constituting chain organopolysiloxane.

Preferably, the organopolysiloxane of the present embodiment further contains 0.1 to 100 parts by mass of cyclic organopolysiloxane represented by the general formula (9) shown below based on 100 parts by mass of the organopolysiloxane component other than the cyclic organopolysiloxane represented by the general formula (9) shown below. The organopolysiloxane containing such a structure represented by the general formula (9) shown below increases the crosslink density of a cured product and improves hardness and gas barrier.

The content of the cyclic organopolysiloxane represented by the following general formula (9) is more preferably 1 to 90 parts by mass, further preferably 5 to 80 parts by mass:

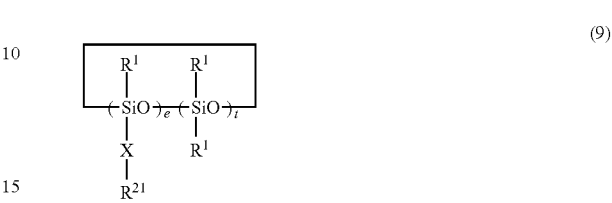

In the general formula (9), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^{21}$ represents an acryloxy group or a methacryloxy group;

X represents a divalent hydrocarbon group having 2 to 10 carbon atoms;

e represents an integer of 1 or larger;

f represents an integer of 0 or larger; and e+f represents an integer of 3 to 20.

Preferably, the organopolysiloxane of the present embodiment further contains 0.01 to 1000 parts by mass of a compound represented by the general formula (10) shown below based on 100 parts by mass of the organopolysiloxane component.

The organopolysiloxane containing the compound represented by the general formula (10) can confer flexibility to a cured product and improve heat and cold shock resistance.

The content of the compound represented by the following general formula (10) is more preferably 0.03 to 900 parts by mass, further preferably 0.05 to 750 parts by mass:

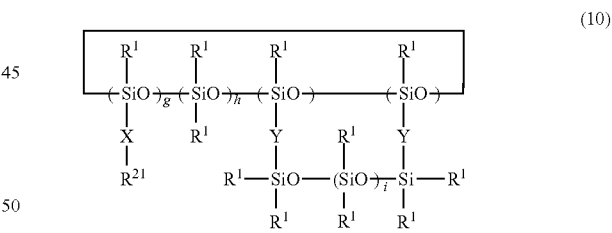

In the general formula (10), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;

$R^{21}$ represents an acryloxy group or a methacryloxy group;

X represents a divalent hydrocarbon group having 2 to 10 carbon atoms;

g represents an integer of 1 or larger;

h represents an integer of 0 or larger; and i represents an integer of 0 to 20.

From the viewpoint of a balance among hardness, gas barrier, and heat and cold shock resistance, the organopolysiloxane of the present embodiment contains the cyclic organopolysiloxane represented by the general formula (9) and the compound represented by the general formula (10), wherein a ratio ([WB]/[WA]) of a content [WB] of the compound represented by the general formula (10) to a content [WA] of the compound represented by the general formula (9) is preferably 0.1 or larger and 20.0 or smaller, more preferably 0.3 or larger and 18 or smaller, further preferably 0.5 or larger and 15 or smaller, the ratio being calculated according to the following formula (III) from peak intensity obtained in measurement by matrix-assisted laser desorption/ionization time-of-flight mass spectrometry:

$$[WB]/[WA] = \frac{\text{Intensity of a peak corresponding to the total sum of the mass of the structure of the general formula (10) and the mass 23 of sodium}}{\text{Intensity of a peak corresponding to the total sum of the mass of the structure of the general formula (9) and the mass 23 of sodium}} \quad \text{(III)}$$

As described above, $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group.

Examples of Fe include: alkyl groups having 1 to 10 carbon atoms, such as a methyl group, an ethyl group, a propyl group, a butyl group, an isobutyl group, a tertiary butyl group, a pentyl group, a neopentyl group, a hexyl group, a cyclopentyl group, a cyclohexyl group, and an octyl group; cycloalkyl groups having 3 to 10 carbon atoms, such as a cyclopropyl group, a cyclobutyl group, a cyclopentyl group, a cyclohexyl group, a cyclooctyl group, and a cyclodecane group; aryl groups such as a phenyl group, a tolyl group, a xylyl group, a cumenyl group, and a mesityl group; aralkyl groups such as a benzyl group, a phenethyl group, and a phenylpropyl group; and groups in which one or more or all hydrogen atoms bonded to the carbon atom(s) of these groups are replaced with a hydroxy group, a cyano group, a halogen atom, etc., such as a hydroxypropyl group, a cyanoethyl group, a 1-chloropropyl group, and a 3,3,3-trifluoropropyl group.

$R^1$ is preferably an alkyl group having 1 to 10 carbon atoms from the viewpoint of light resistance.

$R^1$ is more preferably a methyl group from the viewpoint of the thermal yellowing resistance and light resistance of the organopolysiloxane or the curable resin composition of the present embodiment.

As described above, $R^2$ represents an unsaturated bond-containing group having 2 to 10 carbon atoms.

Examples thereof include: unsaturated chain hydrocarbon groups such as a vinyl group, an allyl group, an isopropenyl group, a 3-butenyl group, a 2-methylpropenyl group, a 4-pentenyl group, a 5-hexenyl group, a 6-heptenyl group, a 7-octenyl group, a 8-nonenyl group, and a 9-decenyl group; unsaturated cyclic hydrocarbon groups such as a cyclohexenyl group and a norbornenyl group; ether bond-containing unsaturated hydrocarbon groups such as a vinyl ether group and an allyl ether group; unsaturated cyclic hydrocarbon groups such as a cyclohexenyl group; and unsaturated fatty acid ester groups such as an acryloxy group and a methacryloxy group.

Among them, an acryloxy group represented by the following formula (12) or a methacryloxy group represented by the following formula (13) (these groups are collectively referred to as a (meth)acryloxy group) is preferred from the viewpoint of the reactivity of a curable resin composition described later, i.e., rapid progress of reaction because of easy thermal curing or light curing:

As described above, X represents a divalent hydrocarbon group having 2 to 10 carbon atoms.

Examples thereof include —(CH$_2$)$_2$—, —(CH$_2$)$_3$—, —(CH$_2$)$_4$—, —(CH$_2$)$_5$—, —(CH$_2$)$_6$—, —(CH$_2$)$_8$—, —(CH$_2$)$_{10}$—, —CH(CH$_3$)CH$_2$—, and —C(CH$_3$)$_2$—. Particularly, —(CH$_2$)$_2$—, —(CH$_2$)$_3$—, and —(CH$_2$)$_4$— are preferred from the viewpoint of the easy availability of starting materials and reactivity, i.e., rapid progress of reaction because of easy thermal curing or light curing.

As described above, Y represents a divalent hydrocarbon group having 2 to 10 carbon atoms.

Examples thereof include —(CH$_2$)$_2$—, —(CH$_2$)$_3$—, —(CH$_2$)$_4$—, —(CH$_2$)$_5$—, —(CH$_2$)$_6$—, —(CH$_2$)$_8$—, —(CH$_2$)$_{10}$—, —CH(CH$_3$)CH$_2$—, and —C(CH$_3$)$_2$—. Particularly, —(CH$_2$)$_3$—, —(CH$_2$)$_4$—, and —(CH$_2$)$_6$— are preferred from the viewpoint of the easy availability of starting materials and reactivity, i.e., rapid progress of reaction because of easy thermal curing or light curing.

The organopolysiloxane of the present embodiment has, as mentioned above, the constitutional units in any combination of (i) F1 and M1, (ii) F1 and T, and (iii) F1, M1, and T.

In the organopolysiloxane of the present embodiment, preferably, a, b, and c in the formulas (1) to (3) satisfy the following formula (I):

$$0.1 \leq a/(b+c) \leq 5 \quad \text{(I)}.$$

The value of a/(b+c) in the formula (I) is preferably 0.1 or larger from the viewpoint of the hardness of a cured product of a curable resin composition (described later) containing the organopolysiloxane and 5 or smaller from the viewpoint of thermal yellowing resistance and light resistance.

The range of this value is more preferably 0.12 or larger and 4 or smaller, further preferably 0.15 or larger and 3 or smaller, from such a viewpoint.

Specific examples of the organopolysiloxane of the present embodiment include the following compounds:

(14)
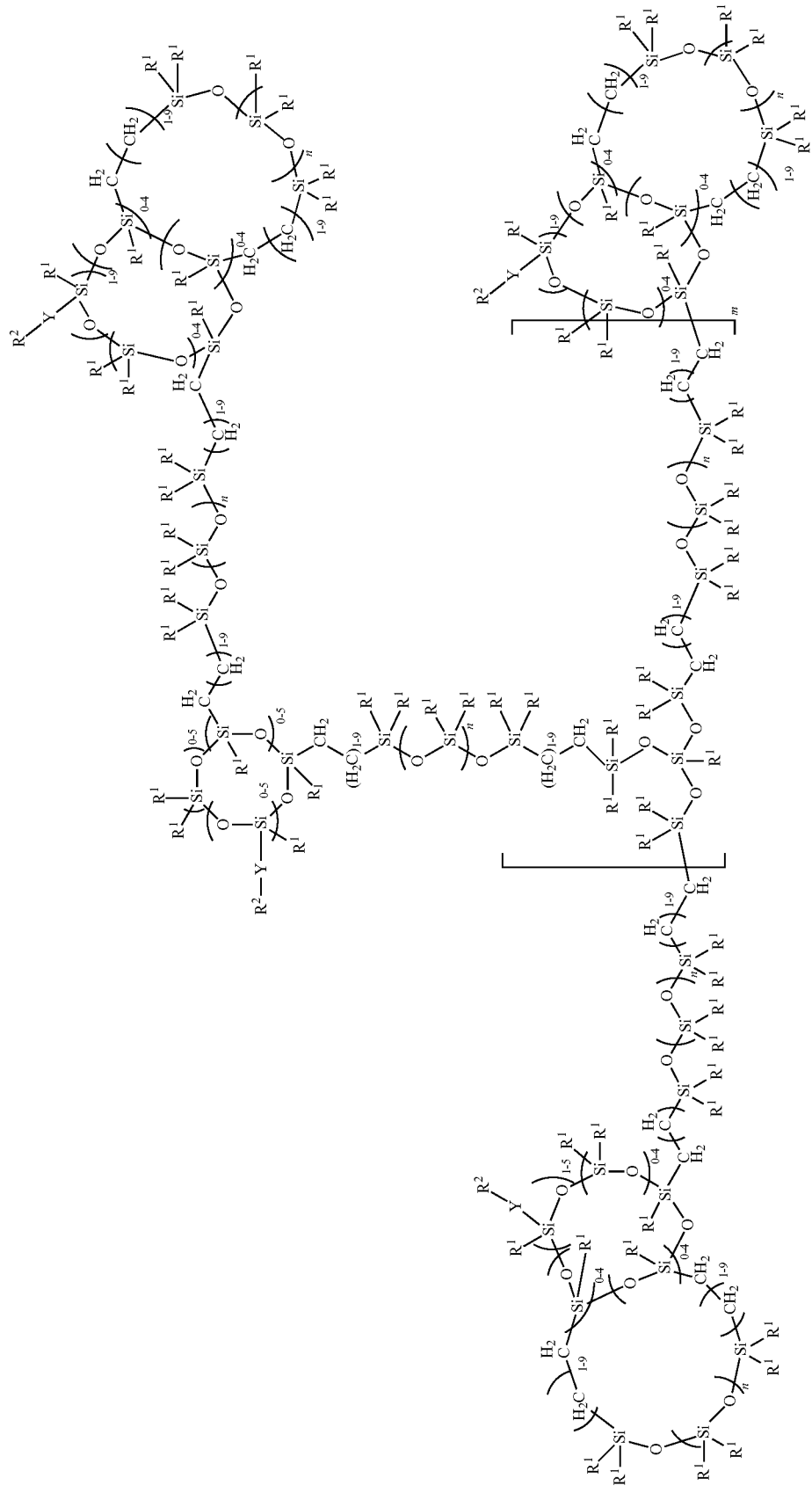

(15)
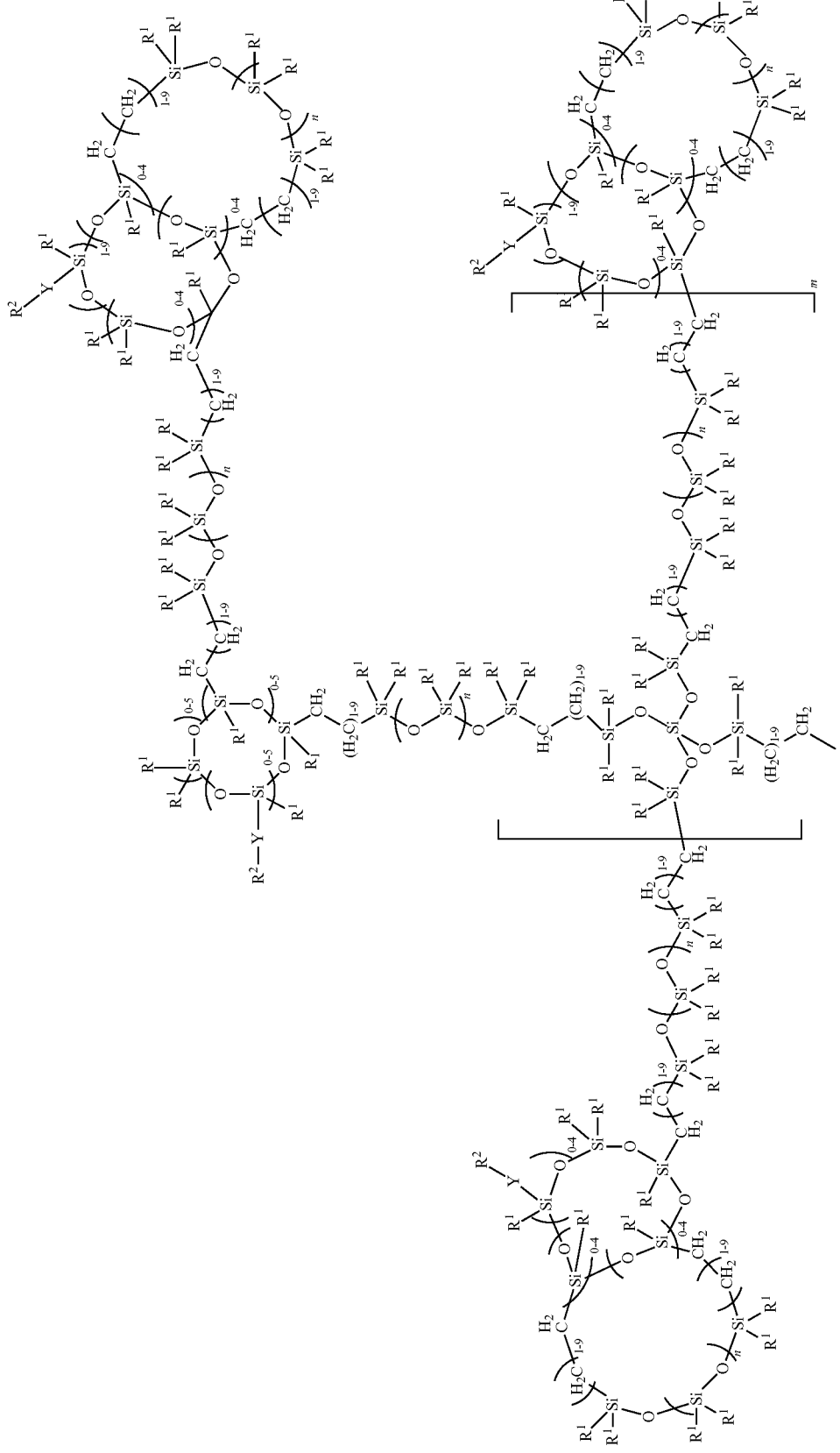

-continued
(16)
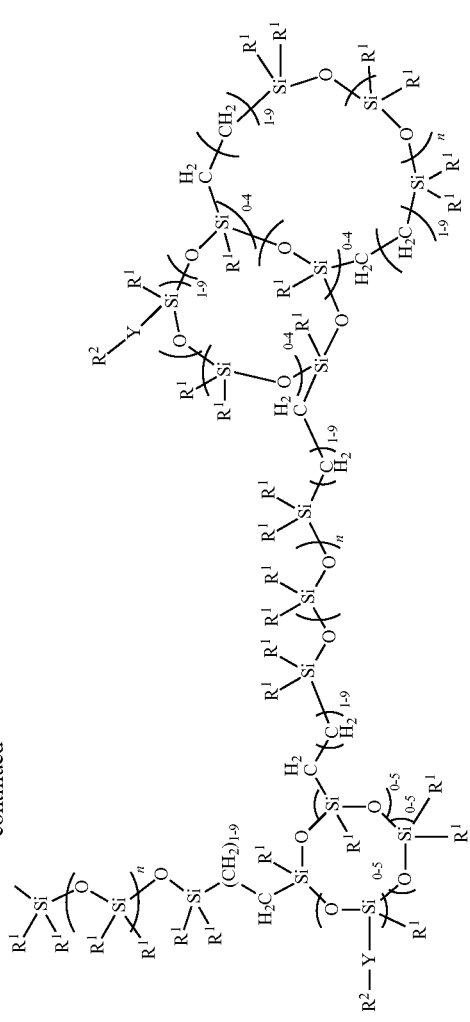
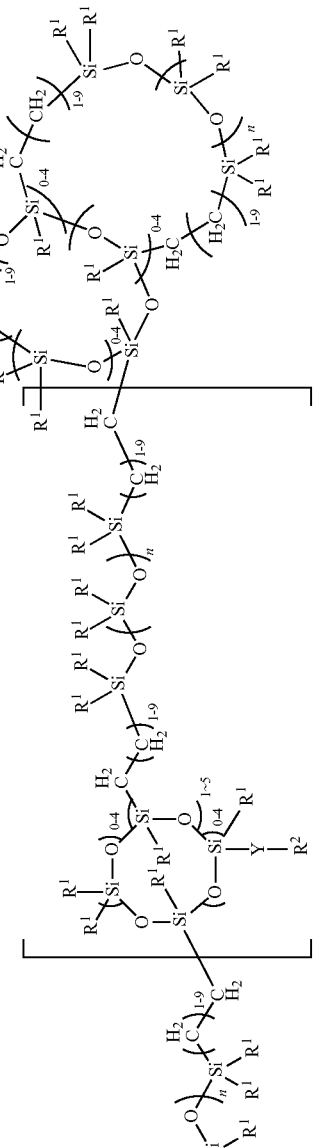

-continued
(17)
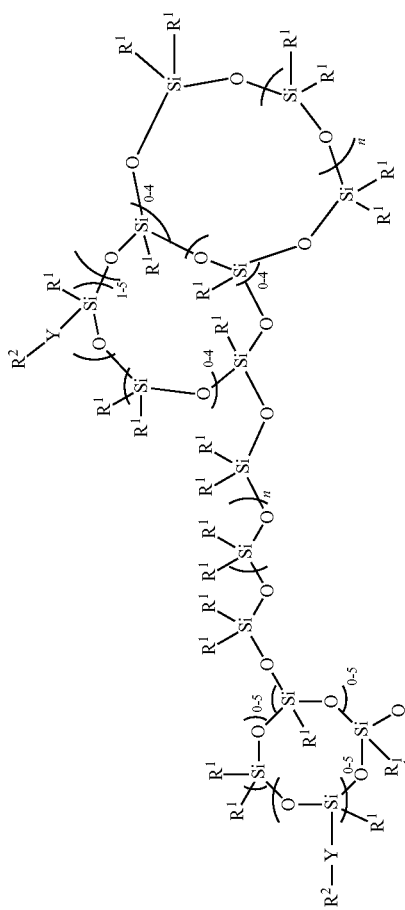
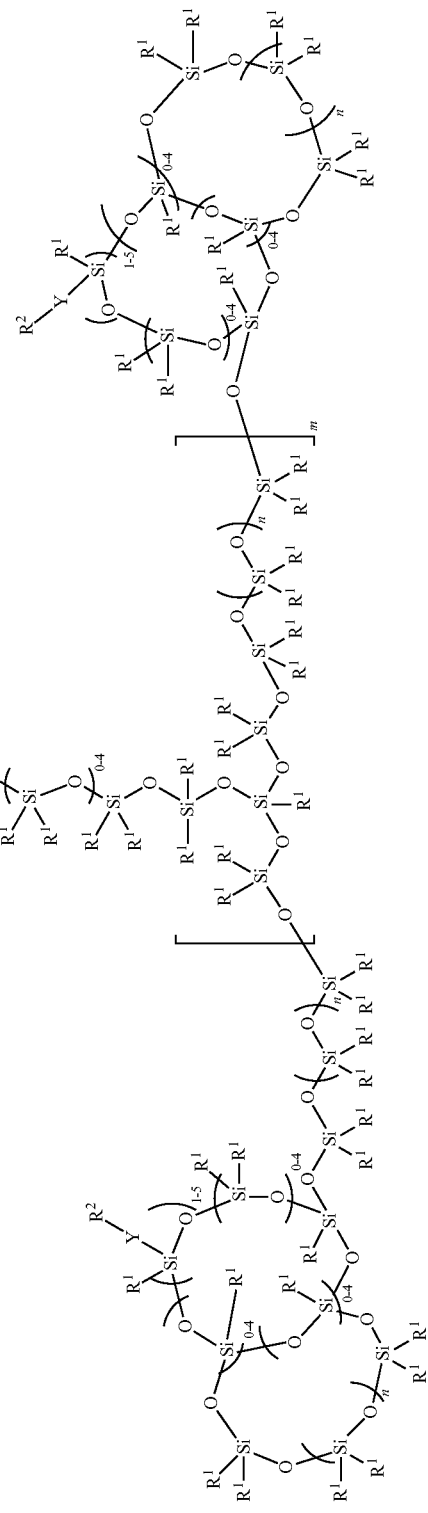

(18)
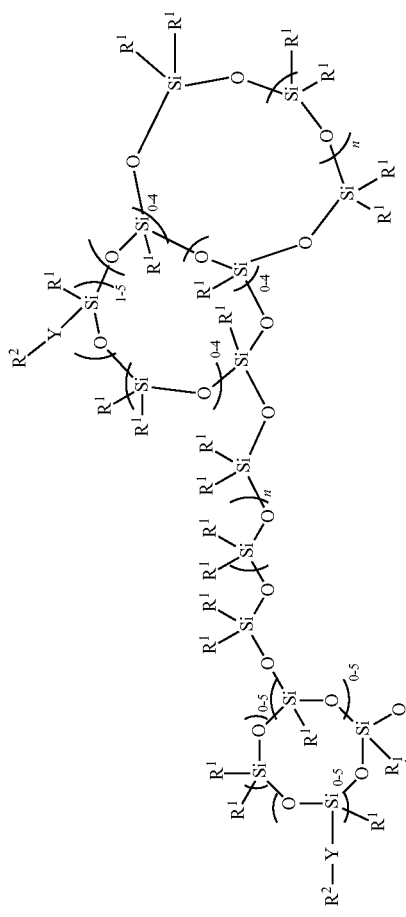
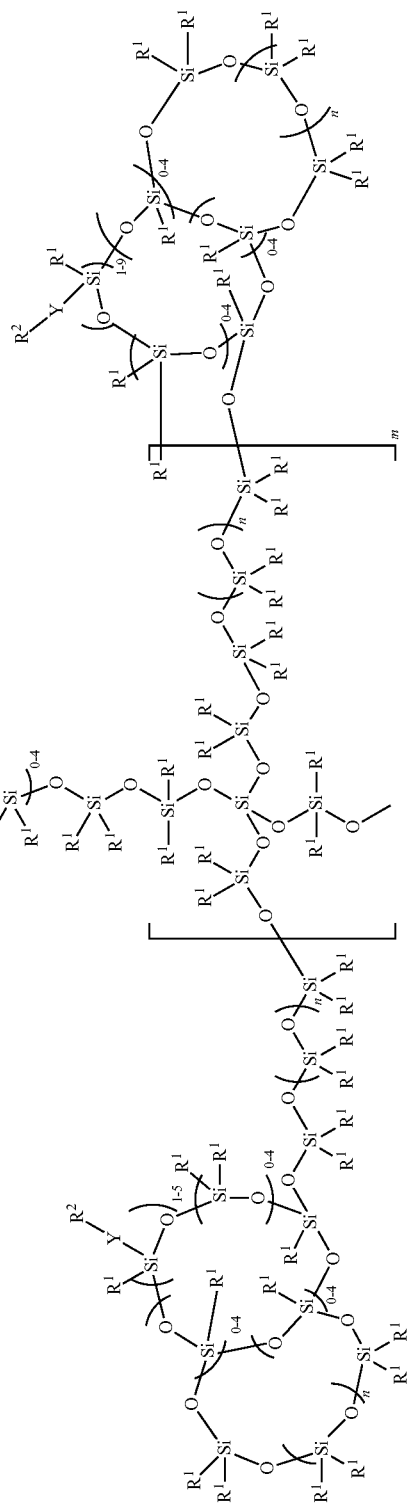

-continued
(19)
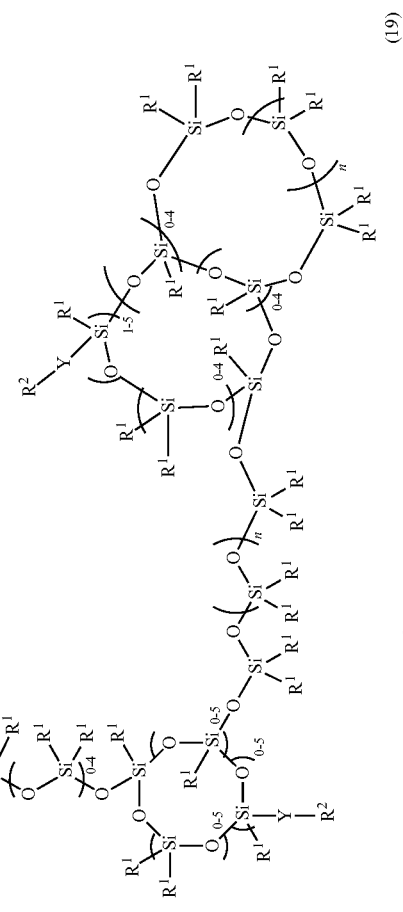
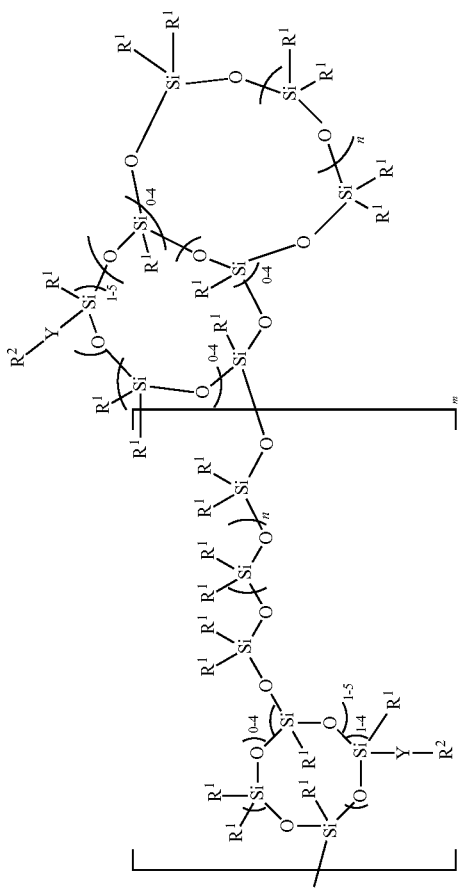
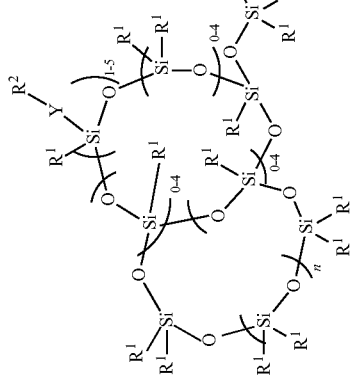

-continued
(20)
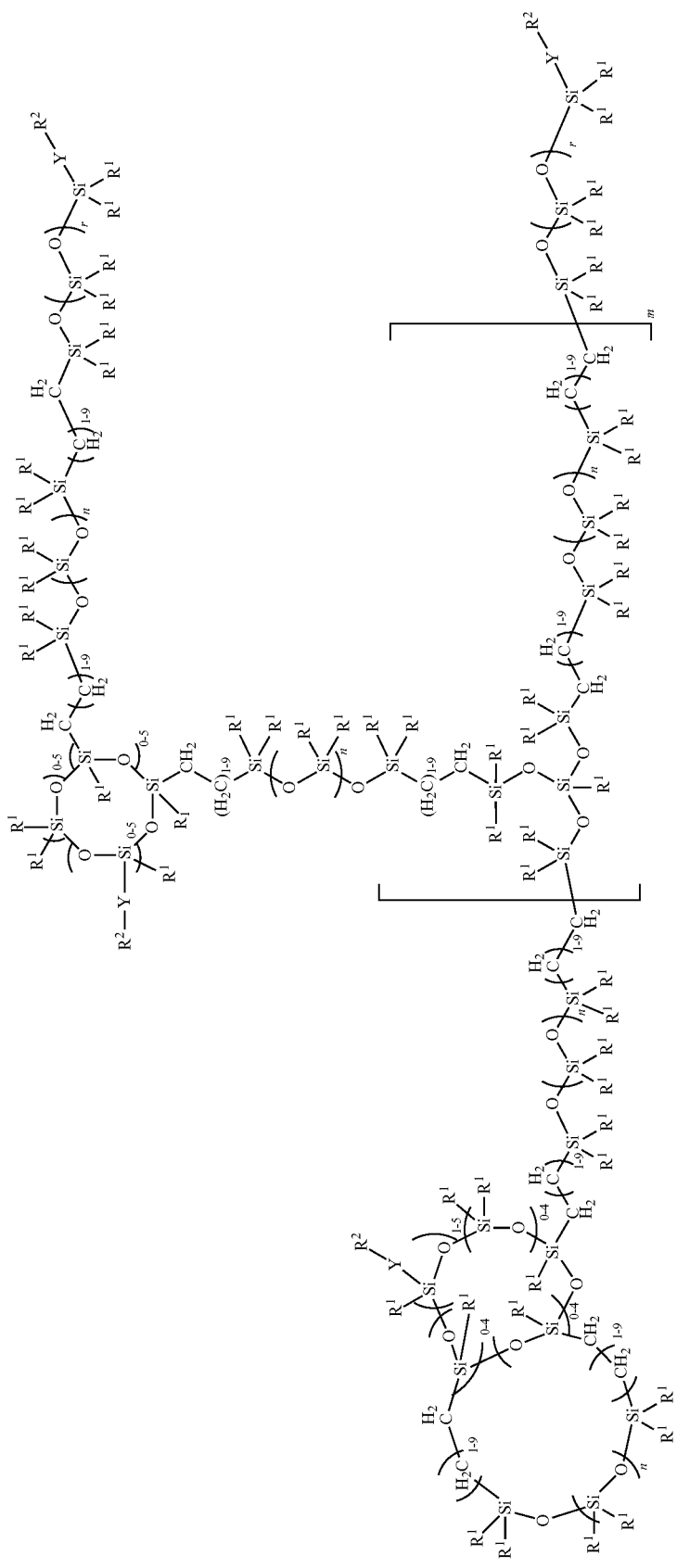

-continued
(21)
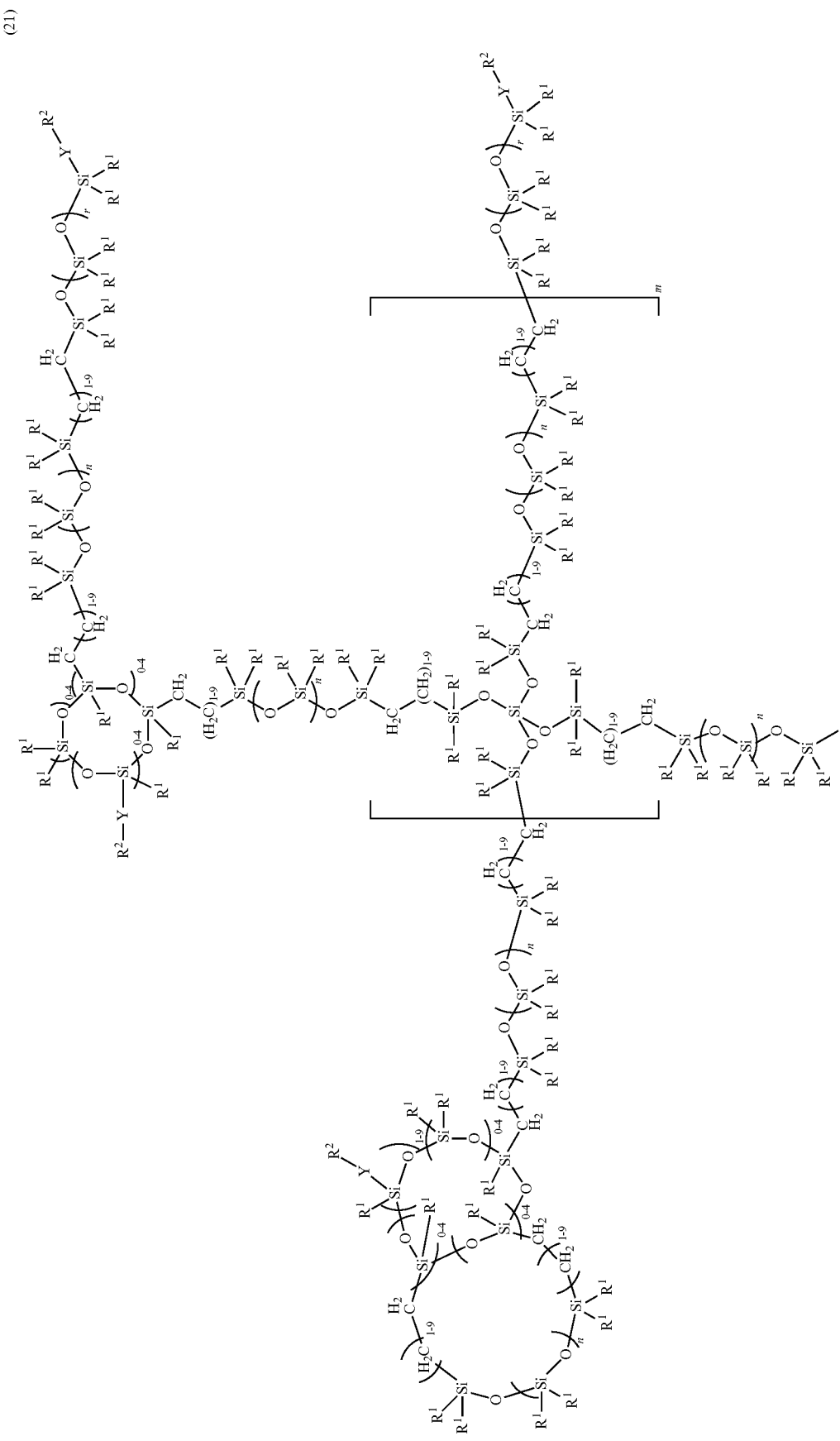

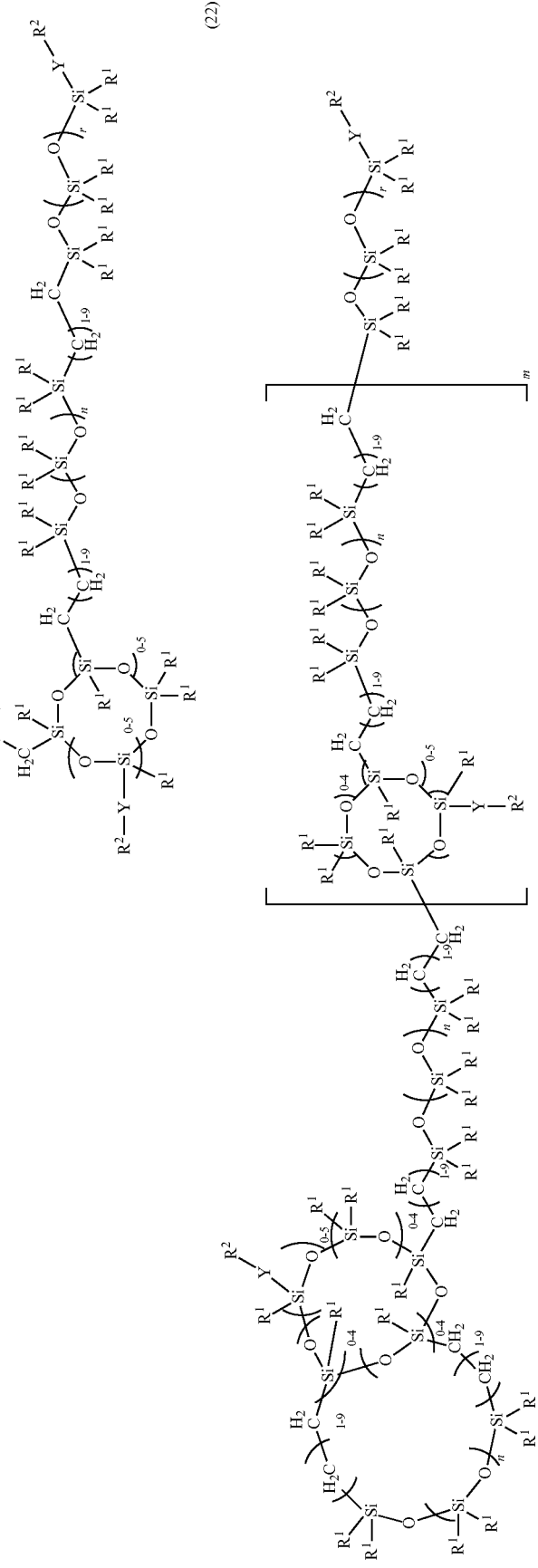

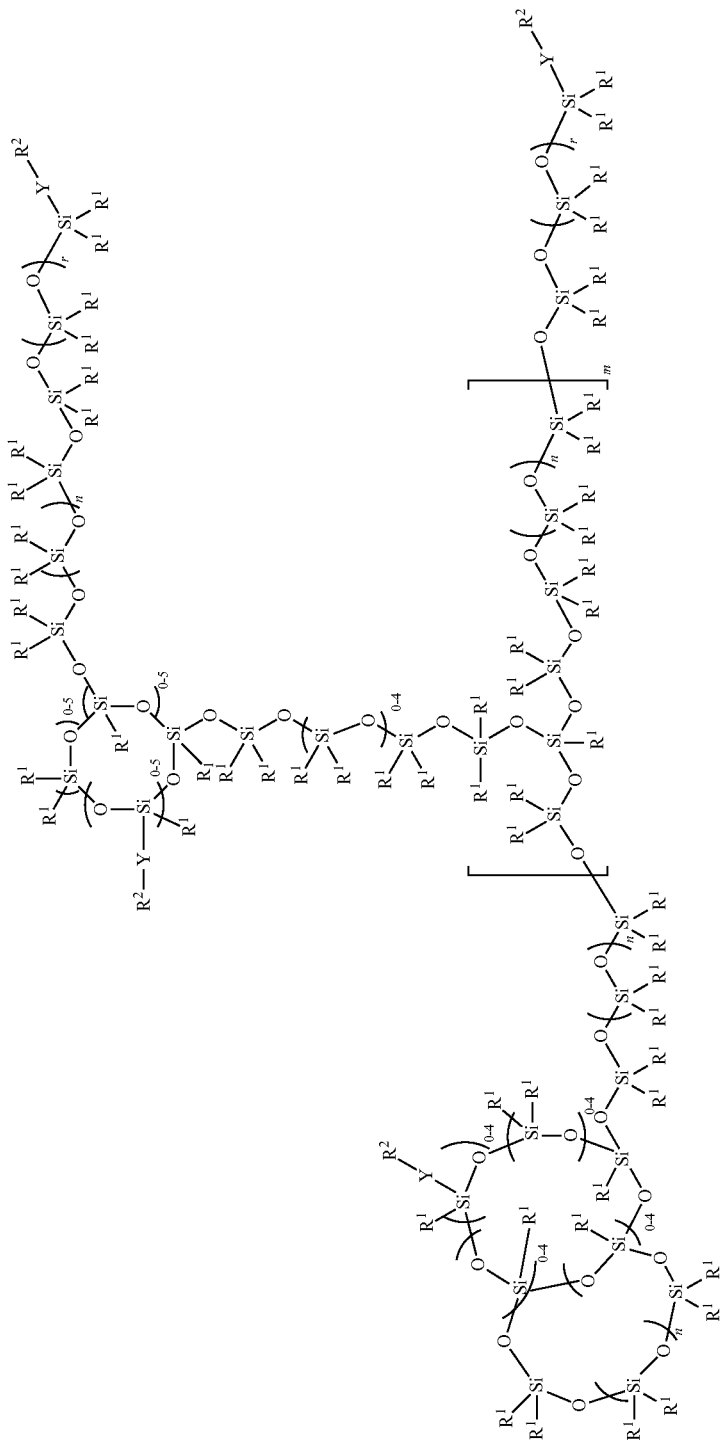
(23)

-continued
(24)
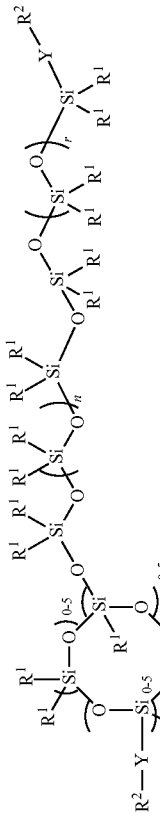 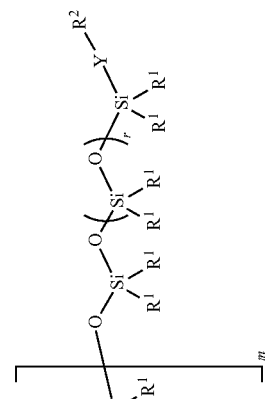 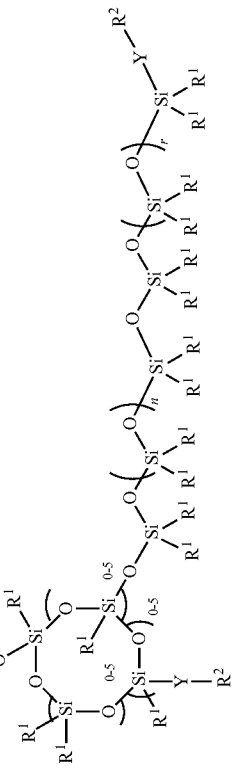
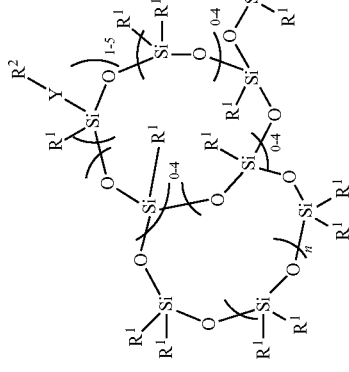

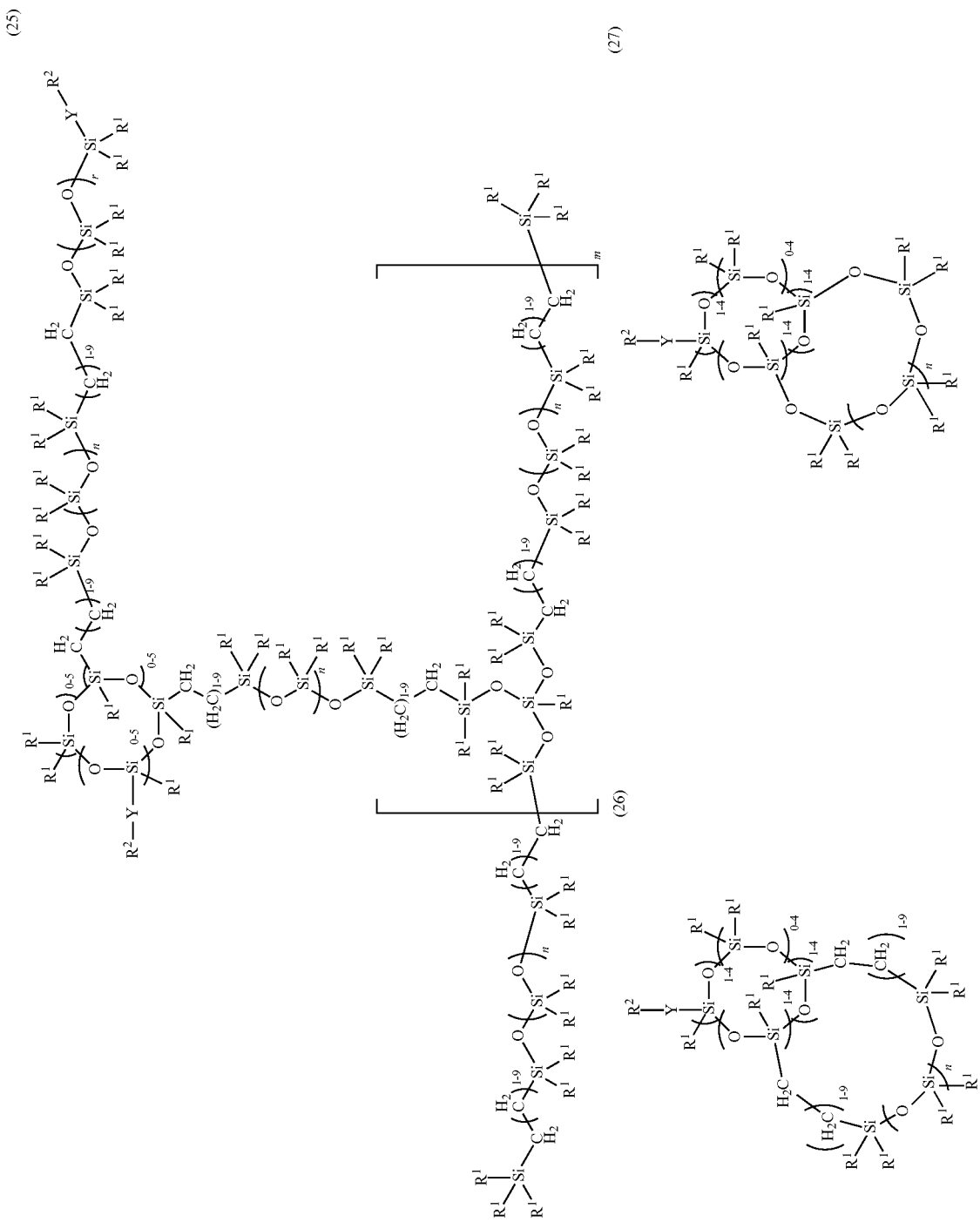

-continued
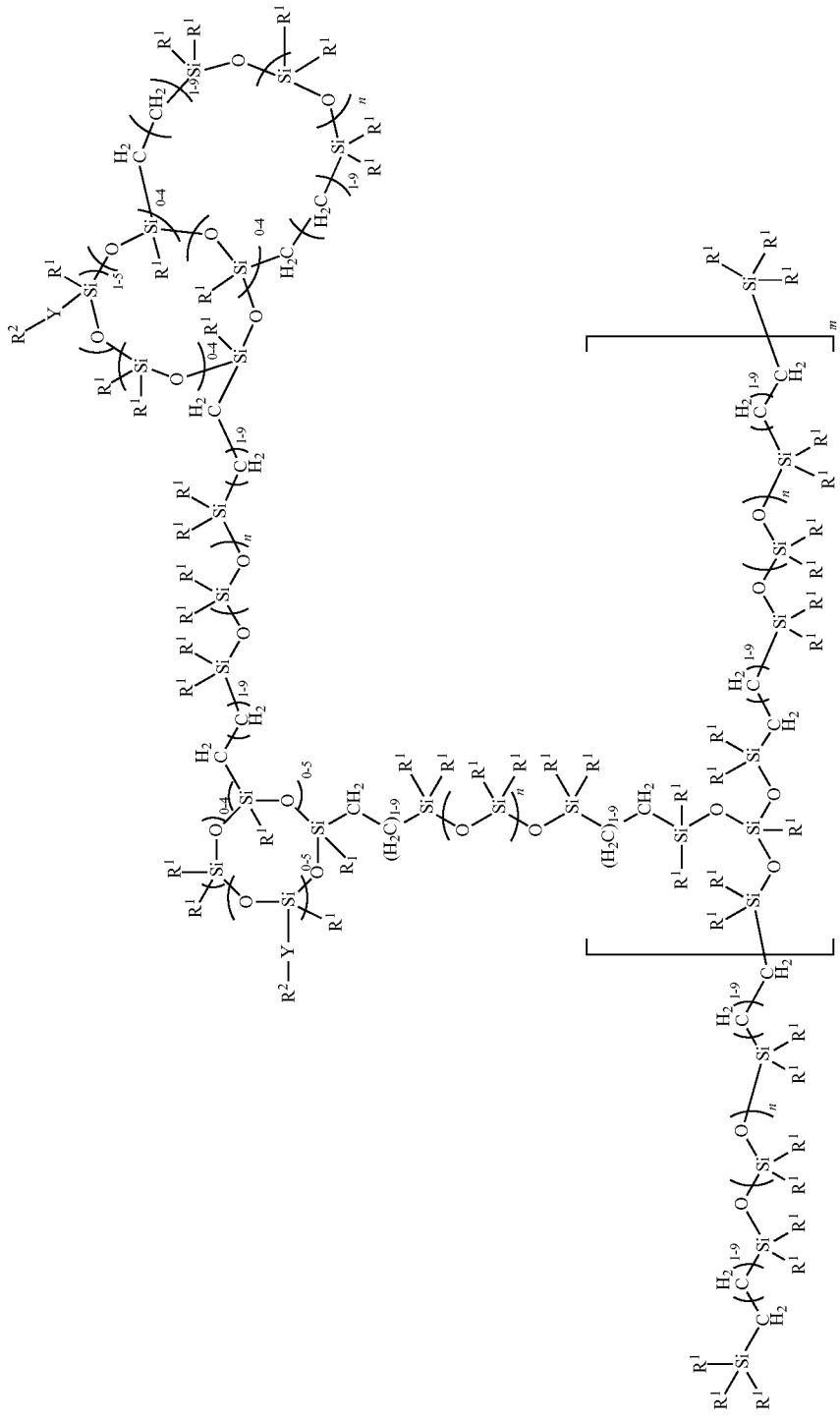
(28)

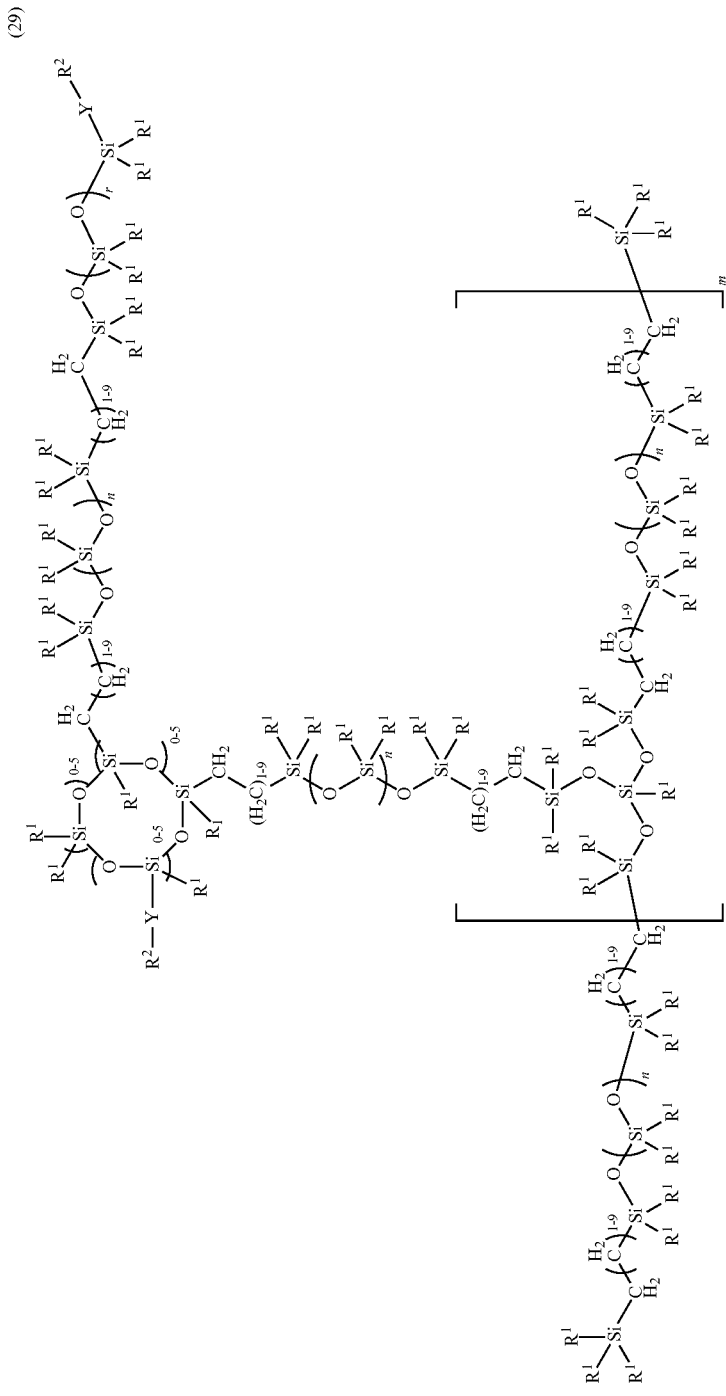
(29)

-continued
(30)
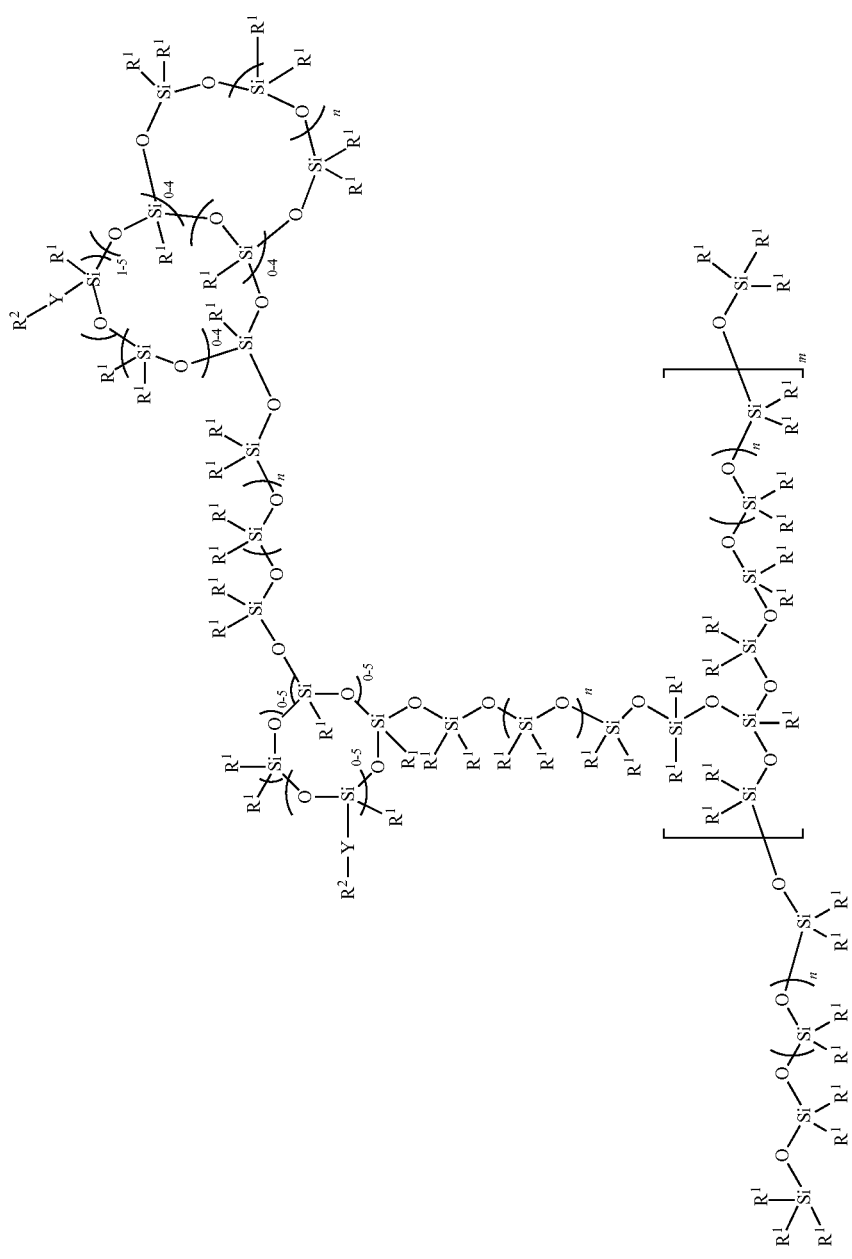

-continued
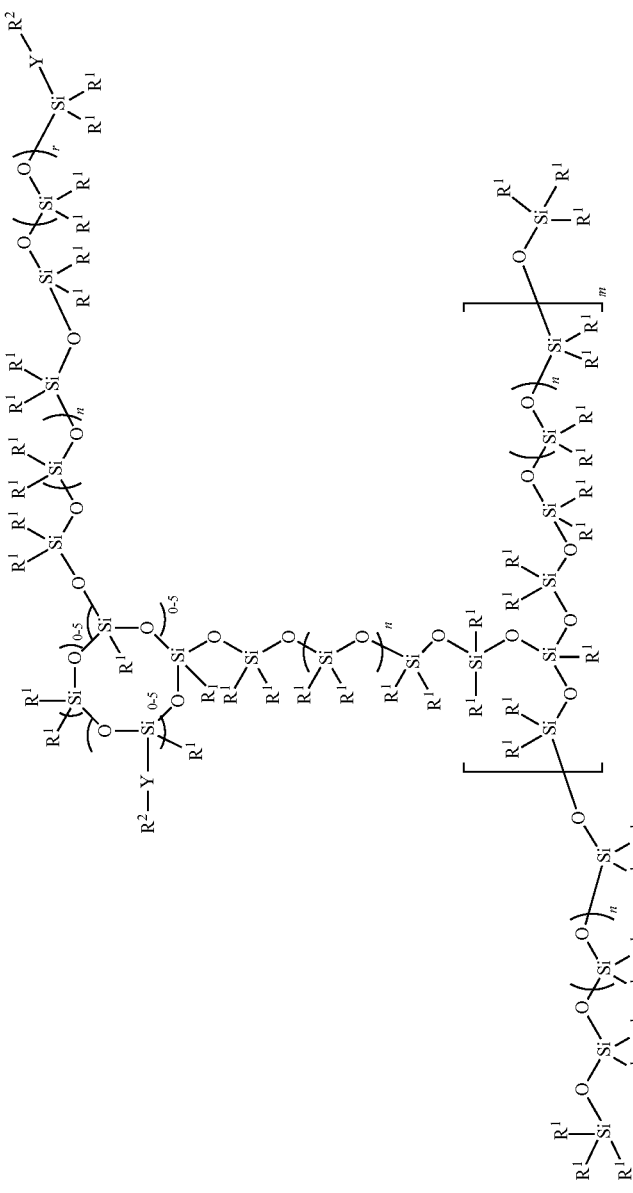
(31)

In the formulas (13) to (31), m represents an integer of 0 to 2000; n represents an integer of 0 to 20; and r represents an integer of 0 to 20.

In the organopolysiloxane of the present embodiment, $R^1$ is preferably a methyl group from the viewpoint of light resistance, $R^2$ is preferably an acryloxy group or a methacryloxy group from the viewpoint of reactivity, and Y is preferably —$(CH_2)_3$—, —$(CH_2)_4$—, or —$(CH_2)_6$— from the viewpoint of the easy availability of starting materials.

In the organopolysiloxane of the present embodiment, $R^2$ in the constitutional unit F1 represented by the general formula (1) comprises an acryloxy group or a methacryloxy group. The functional group equivalent weight of all acryloxy groups or methacryloxy groups contained in the organopolysiloxane of the present embodiment is preferably 210 g/mol or higher from the viewpoint of the thermal yellowing resistance and light resistance of a cured product of a curable resin composition (described later) containing the organopolysiloxane and 2000 g/mol or lower from the viewpoint of hardness. The functional group equivalent weight of the acryloxy groups or the methacryloxy groups is more preferably 250 g/mol and higher and 1500 g/mol or lower, further preferably 300 g/mol or higher and 1000 g/mol or lower, from such a viewpoint.

In this context, the functional group equivalent weight of the acryloxy groups or the methacryloxy groups can be measured by a method described later in Examples.

The weight-average molecular weight of the organopolysiloxane of the present embodiment is preferably 700 or larger from the viewpoint of the heat and cold shock resistance of a cured product of a curable resin composition (described later) containing the organopolysiloxane and 5000000 or smaller from the viewpoint of hardness, more preferably 1000 or larger and 3000000 or smaller, further preferably 1500 or larger and 1000000 or smaller.

The viscosity of the organopolysiloxane of the present embodiment at 25° C. is preferably 50 mPa·s or higher from the viewpoint of the dispersion stability of a phosphor or a colorant and 1000000 mPa·s or lower from the viewpoint of workability. The viscosity is more preferably 80 mPa·s or higher and 500000 mPa·s or lower, further preferably 100 mPa·s or higher and 100000 mPa·s or lower.

The weight-average molecular weight and viscosity of the organopolysiloxane can be measured by methods described later in Examples.

[Method for Producing Organopolysiloxane]

The organopolysiloxane of the present embodiment can be produced by a method comprising performing the addition reaction of hydrogen polysiloxane (a1) represented by the general formula (11) shown below, optional hydrogen polysiloxane (a2) having one or more hydrogen atom(s) directly bonded to silicon atom(s), i) vinyl group-containing organopolysiloxane (b1) having two or more vinyl groups directly bonded to silicon atoms, or polysiloxane (b2) having two or more hydroxy groups directly bonded to silicon atoms, and ii) an organic compound (c) having two or more unsaturated bonds in one molecule in the presence of a hydrosilylation reaction catalyst (d).

Specifically, the addition reaction of the hydrogen polysiloxane (a1), the optional hydrogen polysiloxane (a2), the organopolysiloxane (b1), and the compound (c) in combination or the addition reaction of the hydrogen polysiloxane (a1), the optional hydrogen polysiloxane (a2), the polysiloxane (b2), and the compound (c) in combination is performed in the presence of the catalyst (d).

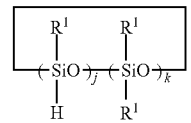

(11)

In the general formula (11), $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group; j represents an integer of 1 or larger; k represents an integer of 0 or larger; and j+k represents an integer of 3 to 20.

Examples of the hydrogen polysiloxane (a1) represented by the general formula (11) having at least one SiH group in one molecule include compounds represented by the following formulas (32), (33), and (34):

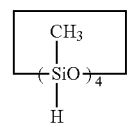

(32)

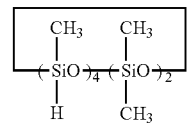

(33)

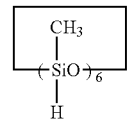

(34)

The hydrogen polysiloxane (a1) may be a combination of two or more kinds or one kind alone.

Examples of the hydrogen polysiloxane (a2) having one or more hydrogen atom(s) directly bonded to silicon atom(s) include compounds represented by the following formulas (35), (36), (37), and (38):

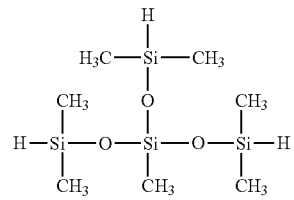

(35)

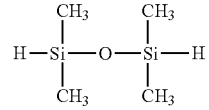

(36)

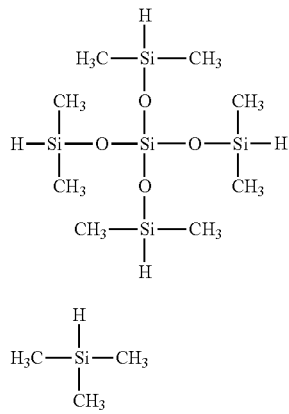

(37)

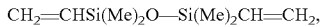

(38)

The hydrogen polysiloxane (a1) and the hydrogen polysiloxane (a2) can be combined at an arbitrary ratio as hydrogen polysiloxanes each having one or more hydrogen atom(s) directly bonded to silicon atom(s) to thereby adjust the hardness and gas barrier of a cured product and the viscosity of a curable resin composition containing the organopolysiloxane of the present embodiment.

A larger proportion of the hydrogen polysiloxane (a1) improves the hardness and gas barrier of a cured product. A larger proportion of the hydrogen polysiloxane (a2) can reduce the viscosity of a curable resin composition containing the organopolysiloxane of the present embodiment, resulting in easy handleability.

Examples of the vinyl group-containing organopolysiloxane (b1) having two or more vinyl groups directly bonded to silicon atoms include the following compounds:

$CH_2=CHSi(Me)_2O-Si(Me)_2CH=CH_2$, $CH_2=CHSi(Me)_2O-Si(Me)_2O-Si(Me)_2CH=CH_2$, $CH_2=CHSi(Me)_2O-(Si(Me))_2O)_2-Si(Me)_2CH=CH_2$, $CH_2=CHSi(Me)_2O-(Si(Me))_2O)_3-Si(Me))_2CH=CH_2$, $CH_2=CHSi(Me)_2O-(Si(Me))_2O)_6-Si(Me)_2CH=CH_2$, $CH_2=CHSi(Me)_2O-(Si(Me))_2O)_8-Si(Me)_2CH=CH_2$, $CH_2=CHSi(Me)_2O-(Si(Me))_2O)_{11}-Si(Me)_2CH=CH_2$, $CH_2=CHSi(Me))_2O-(Si(Me))_2O)_{12}-Si(Me)_2CH=CH_2$, $CH_2=CHSi(Me)_2O-(Si(Me))_2O)_{20}-Si(Me)_2CH=CH_2$, $CH_2=CHCH_2Si(Me)_2O-Si(Me)_2CH_2CH=CH_2$, and $CH_2=CHCH_2Si(Me)_2O-Si(Me)_2O-Si(Me)_2CH_2CH=CH_2$.

In these formulas, Me represents a methyl group.

The vinyl group-containing organopolysiloxane (b1) having two or more vinyl groups directly bonded to silicon atoms may be a combination of two or more kinds or one kind alone.

Examples of the polysiloxane (b2) having two or more hydroxy groups directly bonded to silicon atoms include the following compounds:

$HO-Si(Me)_2O-Si(Me)_2-OH$, $HO-Si(Me)_2O-Si(Me)_2O-Si(Me)_2-OH$, $HO-Si(Me)_2O-(Si(Me)_2O)_2-Si(Me)_2-OH$, $HO-Si(Me)_2O-(Si(Me)_2O)_3-Si(Me)_2-OH$, $HO-Si(Me)_2O-(Si(Me)_2O)_6-Si(Me)_2-OH$, $HO-Si(Me)_2O-(Si(Me)_2O)_8-Si(Me)_2-OH$, $HO-Si(Me)_2O-(Si(Me)_2O)_{11}-Si(Me)_2-OH$, $HO-Si(Me)_2O-(Si(Me)_2O)_{12}-Si(Me))_2-OH$, and $HO-Si(Me)_2O-(Si(Me)_2O)_{20}-Si(Me)_2-OH$.

In these formulas, Me represents a methyl group.

The polysiloxane (b2) having two or more hydroxy groups directly bonded to silicon atoms may be a combination of two or more kinds or one kind alone.

The organic compound (c) having two or more unsaturated bonds in one molecule is represented by the following general formula (39):

$$CH_2=CH-R^3-R^2 \qquad (39)$$

In the general formula (39), $R^2$ represents an unsaturated bond-containing group having 2 to 10 carbon atoms; and $R^3$ represents a divalent hydrocarbon group having 1 to 8 carbon atoms.

The number of carbon atoms in $R^3$ is particularly preferably 1 to 4. This allows the hydrosilylation reaction to be securely performed.

The number of carbon atoms in $R^3$ can be set to 4 or less to thereby reduce the boiling point of the compound (c). Thus, the excess compound (c) can be distilled off easily from the reaction solution.

The organic compound (c) having two or more unsaturated bonds in one molecule may be a combination of two or more kinds or one kind alone.

In the step of producing the organopolysiloxane of the present embodiment, preferably, the usage amount (molar quantity) of the organic compound (c) having two or more unsaturated bonds in one molecule is in excess with respect to a difference between the sum of the molar quantity of the SiH group derived from the hydrogen polysiloxane (a1) represented by the general formula (11) and the molar quantity of the SiH group derived from the optionally added hydrogen polysiloxane (a2) having one or more hydrogen atom(s) directly bonded to silicon atom(s) and the molar quantity of the vinyl groups of the vinyl group-containing organopolysiloxane (b1) having two or more vinyl groups directly bonded to silicon atoms or the molar quantity of the hydroxy groups of the polysiloxane (b2) having two or more hydroxy groups directly bonded to silicon atoms, i.e., [Molar quantity of the SiH group of (a1)+Molar quantity of the SiH group of (a2)]–[Molar quantity of the vinyl groups of (b1) or Molar quantity of the hydroxy groups of (b2)], from the viewpoint of the complete reaction of the SiH groups without being left.

Specifically, [Molar quantity of the organic compound (c) having two or more unsaturated bonds in one molecule]/[(Molar quantity of the SiH groups derived from (a1) and (a2))–(Molar quantity of the vinyl groups derived from (b1) or Molar quantity of the hydroxy groups derived from (b2))] =1.2 to 3.0 is preferred.

The hydrosilylation reaction catalyst (d) is not particularly limited, and any conventionally known hydrosilylation reaction catalyst can be used.

Examples thereof include: platinum-based catalysts such as platinum black, platinum(II) chloride, chloroplatinic acid, reaction products of chloroplatinic acid and monohydric alcohols, complexes of chloroplatinic acid and olefins, and platinum bisacetoacetate; and platinum-group metal catalysts other than platinum-based catalysts, such as palladium-based catalysts and rhodium-based catalysts.

The hydrosilylation reaction catalyst (d) may be a combination of two or more kinds or one kind alone.

The amount of the hydrosilylation reaction catalyst (d) is not particularly limited and is preferably 0.01 to 100 ppm based on the weight of the organopolysiloxane which is a product obtained by the addition reaction of the hydrogen polysiloxane (a1) represented by the general formula (11), the optional hydrogen polysiloxane (a2) having one or more hydrogen atom(s) directly bonded to silicon atom(s), i) the vinyl group-containing organopolysiloxane (b1) having two or more vinyl groups directly bonded to silicon atoms, or the polysiloxane (b2) having two or more hydroxy groups directly bonded to silicon atoms, and ii) the organic compound (c) having two or more unsaturated bonds in one molecule.

The amount of the hydrosilylation reaction catalyst (d) is preferably 0.01 ppm or higher from the viewpoint of the sufficient obtainment of effects brought about by the addition of the catalyst (d) and 100 ppm or lower from the viewpoint of cost.

The hydrosilylation reaction catalyst (d) can be removed using an adsorbent such as active alumina or active carbon after the addition reaction.

From the viewpoint of thermal yellowing resistance and light resistance, the amount of the hydrosilylation reaction catalyst (d) described later is preferably 0.001 parts by mass or less based on 100 parts by mass of the organopolysiloxane which is a product obtained by the addition reaction of the hydrogen polysiloxane (a1) represented by the general formula (11), the optional hydrogen polysiloxane (a2) having one or more hydrogen atom(s) directly bonded to silicon atom(s), i) the vinyl group-containing organopolysiloxane (b1) having two or more vinyl groups directly bonded to silicon atoms, or the polysiloxane (b2) having two or more hydroxy groups directly bonded to silicon atoms, and ii) the organic compound (c) having two or more unsaturated bonds in one molecule.

The amount of the hydrosilylation reaction catalyst (d) in the curable resin composition can be measured by analysis on the curable resin composition as described later.

The addition reaction in the step of producing the organopolysiloxane of the present embodiment can usually be performed at room temperature to 100° C.

In the case where $R^2$ is a (meth)acryloxy group, the reaction temperature is preferably 40° C. to 70° C. because the (meth)acryloxy group easily reacts at a high temperature to cause gelling.

The addition reaction is performed in a solvent, if necessary.

Examples of the solvent that can be used include: aromatic-based solvents such as toluene and xylene; aliphatic-based solvents such as hexane and octane; ketone-based solvents such as methyl ethyl ketone and methyl isobutyl ketone; ester-based solvents such as ethyl acetate and isobutyl acetate; ether-based solvents such as diisopropyl ether, 1,4-dioxane, diethyl ether, tetrahydrofuran, ethylene glycol dimethyl ether, ethylene glycol diethyl ether, and propylene glycol monomethyl ether acetate; and alcohol-based solvents such as isopropanol; and mixed solvents thereof.

The atmosphere in which the addition reaction is performed may be any of air and inert gases. The addition reaction is preferably performed in an inert gas such as nitrogen, argon, or helium in terms of the low coloring of the obtained organohydropolysiloxane. In the case where $R^2$ is a (meth) acryloxy group, a small amount of oxygen may be introduced to the reaction atmosphere for the purpose of preventing the polymerization reaction of the (meth)acryloxy group.

In the case where $R^2$ is a (meth)acryloxy group, a polymerization inhibitor such as phenothiazine, a hindered phenol compound, an amine-based compound, or a quinone-based compound is preferably added to the reaction system for the purpose of preventing the polymerization reaction of the (meth)acryloxy group. The kind and amount of such a polymerization inhibitor are not particularly limited as long as the addition thereof can prevent the polymerization reaction of the (meth)acryloxy group, i.e., the acryloxy group or the methacryloxy group, without hindering the progress of the hydrosilylation reaction.

After the completion of the addition reaction, the addition reaction catalyst can be removed from the reaction mixture by a general method such as washing with water or active carbon treatment. In the case of using the excess organic compound (c) having two or more unsaturated bonds in one molecule and the solvent, the solvent, etc., is distilled off by heating and/or under reduced pressure to obtain organopolysiloxane having constitutional units F1, M1, and T in any combination of (i) F1 and M1,
(ii) F1 and T, and
(iii) F1, M1, and T, wherein the constitutional units F1, M1, and T are represented by the general formulas (1), (2), and (3), respectively.

In the step of producing the organopolysiloxane of the present embodiment, the addition reaction can be carried out by one-stage synthesis involving preparing in advance a reaction solution containing the hydrogen polysiloxane (a1), the optional hydrogen polysiloxane (a2), the vinyl group-containing organopolysiloxane (b1), and the organic compound (c) having two or more unsaturated bonds in one molecule, or the hydrogen polysiloxane (a1), the optional hydrogen polysiloxane (a2), the polysiloxane (b2) containing two or more hydroxy groups directly bonded to silicon atoms, and the organic compound (c) having two or more unsaturated bonds in one molecule, and adding the hydrosilylation reaction catalyst (d) to the reaction solution.

Alternatively, in the step of producing the organopolysiloxane of the present embodiment, the addition reaction may be carried out by performing, in order, the steps of preparing a reaction solution containing the hydrogen polysiloxane (a1), the optional hydrogen polysiloxane (a2), and the organic compound (c) having two or more unsaturated bonds in one molecule, adding the hydrosilylation reaction catalyst (d) to the reaction solution to form an adduct of the hydrogen polysiloxane (a1), the optional hydrogen polysiloxane (a2), the organic compound (c) having two or more unsaturated bonds in one molecule (first stage), and adding the vinyl group-containing diorganopolysiloxane (b1) or the polysiloxane (b2) having two or more hydroxy groups directly bonded to silicon atoms to the reaction solution (second stage).

[Curable Resin Composition]

(Thermal Radical Generator)

One example of the curable resin composition of the present embodiment includes a so-called thermosetting resin composition containing the organopolysiloxane and a thermal radical generator.

The thermal radical generator is not particularly limited as long as the radical generator causes radical polymerization of (meth)acryloxy groups by heat.

Examples thereof include: organic peroxides such as benzoyl peroxide, lauryl peroxide, t-butyl peroxide, and cumene hydroperoxide; and azo compounds such as azobisisobutyronitrile.

Specific examples thereof include, but not particularly limited to, organic peroxides such as: azonitrile compounds such as 2,2-azobis(4-methoxy-2,4-dimethylvaleronitrile) (V-70, manufactured by Wako Pure Chemical Industries, Ltd.), 2,2'-azobis(2,4-dimethylvaleronitrile) (V-65, manufactured by Wako Pure Chemical Industries, Ltd.), 2,2'-azobisisobutyronitrile (V-60, manufactured by Wako Pure Chemical Industries, Ltd.), and 2,2'-azobis(2-methylbutyronitrile) (V-59, manufactured by Wako Pure Chemical Industries, Ltd.); diacyl peroxides such as octanoyl peroxide (PEROYL O, manufactured by NOF Corp.), lauroyl peroxide (PEROYL L, manufactured by NOF Corp.), stearoyl peroxide (PEROYL S, manufactured by NOF Corp.), succinic acid peroxide (PEROYL SA, manufactured by NOF Corp.), benzoyl peroxide (NYPER BW, manufactured by NOF Corp.), isobutyryl peroxide (PEROYL IB, manufactured by NOF Corp.), 2,4-dichlorobenzoyl peroxide (NYPER CS, manufactured by NOF Corp.), and 3,5,5-trimethylhexanoyl peroxide (PEROYL 355, manufactured by NOF Corp.); peroxydicarbonates such as di-n-propyl peroxydicarbonate (PEROYL NPP-50M, manufactured by NOF Corp.), diisopropyl peroxydicarbonate (PEROYL IPP-50, manufactured by NOF Corp.), bis(4-t-butylcyclohexyl) peroxydicarbonate (PEROYL TCP, manufactured by NOF Corp.), di-2-ethoxyethyl peroxydicarbonate (PEROYL EEP, manufactured by NOF Corp.), di-2-ethoxyhexyl peroxydicarbonate (PEROYL OPP, manufactured by NOF Corp.), di-2-methoxybutyl peroxydicarbonate (PEROYL MBP, manufactured by NOF Corp.), and di(3-methyl-3-methoxybutyl) peroxydicarbonate (PEROYL SOP, manufactured by NOF Corp.); hydroperoxides such as t-butyl hydroperoxide (PERBUTYL H-69, manufactured by NOF Corp.), and 1,1,3,3-tetramethylbutyl hydroperoxide (PEROCTA H, manufactured by NOF Corp.); dialkyl peroxides such as di-t-butyl peroxide (PERBUTYL D, manufactured by NOF Corp.) and 2,5-dimethyl-2,5-bis(t-butylperoxy)hexane (PERHEXA 25B, manufactured by NOF Corp.); and peroxyesters such as α,α'-bis(neodecanoylperoxy)diisopropylbenzene (NYPER ND, manufactured by NOF Corp.), cumyl peroxyneodecanoate (PERCUMYL ND, manufactured by NOF Corp.), 1,1,3,3-tetramethylbutyl peroxyneodecanoate (PEROCTA ND, manufactured by NOF Corp.), 1-cyclohexyl-1-methylethyl peroxyneodecanoate (PERCYCLO ND, manufactured by NOF Corp.), t-hexyl peroxyneodecanoate (PERHEXYL ND, manufactured by NOF Corp.), t-butyl peroxyneodecanoate (PERBUTYL ND, manufactured by NOF Corp.), t-hexyl peroxypivalate (PERHEXYL PV, manufactured by NOF Corp.), t-butyl peroxypivalate (PERBUTYL PV, manufactured by NOF Corp.), 1,1,3,3,-tetramethylbutyl peroxy-2-ethylhexanoate (PEROCTA O, manufactured by NOF Corp.), 2,5-dimethyl-2,5-bis(2-ethylhexanoylperoxy)hexane (PERHEXA 250, manufactured by NOF Corp.), 1-cyclohexyl-1-methylethyl peroxy-2-ethylhexanoate (PERCYCLO O, manufactured by NOF Corp.), t-hexyl peroxy-2-ethylhexanoate (PERHEXYL O, manufactured by NOF Corp.), t-butyl peroxy-2-ethylhexanoate (PERBUTYL O, manufactured by NOF Corp.), t-butyl peroxyisobutyrate (PERBUTYL IB, manufactured by NOF Corp.), t-hexyl peroxyisopropylmonocarbonate (PERHEXYL I, manufactured by NOF Corp.), t-butylperoxymaleic acid (PERBUTYL MA, manufactured by NOF Corp.), t-amyl peroxy-2-ethylhexanoate (Trigonox 121, manufactured by Kayaku Akzo Corp.), and t-amyl peroxy-3,5,5-trimethylhexanoate (Kayaester AN, manufactured by Kayaku Akzo Corp.).

These thermal radical generators may be used alone or in combination of two or more thereof.

The content of the thermal radical generator is preferably 0.5 to 10 parts by mass based on 100 parts by mass of the organopolysiloxane of the present embodiment which is a product of the addition reaction of the hydrogen polysiloxane (a1) represented by the general formula (11), the optional hydrogen polysiloxane (a2) having one or more hydrogen atom(s) directly bonded to silicon atom(s), i) the vinyl group-containing organopolysiloxane (b1) having two or more vinyl groups directly bonded to silicon atoms, or the polysiloxane (b2) having two or more hydroxy groups directly bonded to silicon atoms, and ii) the organic compound (c) having two or more unsaturated bonds in one molecule.

The content of the thermal radical generator of 0.5 parts by mass or more offers excellent curability. The content of 10 parts by mass or less produces a curable resin composition and a cured product excellent in thermal yellowing resistance. The content of the thermal radical generator is more preferably 1 part by mass or more and 8 parts by mass or less, further preferably 2 parts by mass or more and 5 parts by mass or less, from such a viewpoint.

(Photo-Radical Generator)

Another example of the curable resin composition of the present embodiment includes a so-called photo-curable resin composition containing the organopolysiloxane and a photo-radical generator.

The photo-radical generator is not particularly limited as long as the radical generator causes radical polymerization of (meth)acryloxy groups by light.

Specific examples thereof include: triazine derivatives described in Japanese Patent Publication No. 59-1281, Japanese Patent Publication No. 61-9621, and Japanese Patent Laid-Open No. 60-60104; organic peroxides described in Japanese Patent Laid-Open No. 59-1504 and Japanese Patent Laid-Open No. 61-243807; diazonium compounds described in Japanese Patent Publication No. 43-23684, Japanese Patent Publication No. 44-6413, Japanese Patent Publication No. 44-6413, and Japanese Patent Publication No. 47-1604, and U.S. Pat. No. 3,567,453; organic azide compounds described in U.S. Pat. No. 2,848,328, U.S. Pat. No. 2,852,379, and U.S. Pat. No. 2,940,853; ortho-quinonediazides described in Japanese Patent Publication No. 36-22062, Japanese Patent Publication No. 37-13109, Japanese Patent Publication No. 38-18015, and Japanese Patent Publication No. 45-9610; various onium compounds described in Patent Documents such as Japanese Patent Publication No. 55-39162 and Japanese Patent Laid-Open No. 59-14023, and Macromolecules, Vol. 10, p. 1307 (1977); azo compounds described in Japanese Patent Laid-Open No. 59-142205; metal-allene complexes described in Japanese Patent Laid-Open No. 1-54440, European Patent No. 109,851, European Patent No. 126,712, and J. Imag. Sci., Vol. 30, p. 174 (1986); (oxo)sulfonium-organic boron complexes described in Japanese Patent Laid-Open No. 6-213861 and Japanese Patent Laid-Open No. 6-255347; titanocenes described in Japanese Patent Laid-Open No. 61-151197; transition metal complexes containing a transition metal such as ruthenium, described in Coordination Chemistry Review, Vol. 84, No. 85, p. 277 (1988), and Japanese Patent Laid-Open No. 2-182701; 2,4,5-triarylimidazole dimers described in Japanese Patent Laid-Open No. 3-209477; carbon tetrabromide; and organic halogen compounds described in Japanese Patent Laid-Open No. 59-107344.

These photo-radical generators may be used alone or in combination of two or more thereof.

The content of the photo-radical generator is preferably 0.5 to 20 parts by mass based on 100 parts by mass of the organopolysiloxane of the present embodiment which is a product of the addition reaction of the hydrogen polysiloxane (a1) represented by the general formula (11), the optional hydrogen polysiloxane (a2) having one or more hydrogen atom(s) directly bonded to silicon atom(s),
i) the vinyl group-containing organopolysiloxane (b1) having two or more vinyl groups directly bonded to silicon atoms, or the polysiloxane (b2) having two or more hydroxy groups directly bonded to silicon atoms, and
ii) the organic compound (c) having two or more unsaturated bonds in one molecule.

The content of the photo-radical generator of 0.5 parts by mass or more offers excellent curability. The content of 20 parts by mass or less produces a curable resin composition and a cured product excellent in light resistance. The content of the photo-radical generator is more preferably 0.1 parts by mass or more and 15 parts by mass or less, further preferably 1 part by mass or more and 10 parts by mass or less, from such a viewpoint.

(Other Components)

The curable resin composition of the present embodiment may be supplemented with, for example, a radical polymerizable compound (e.g., (meth)acrylate monomers or oligomers and vinyl (meth)acrylate), if necessary, for the purpose of promoting curability by (improving sensitivity to) energy such as heat or ultraviolet rays.

The curable resin composition of the present embodiment may additionally contain additives such as an antidegradant, a mold release agent, a diluent, an antioxidant, a heat stabilizer, a flame retardant, a plasticizer, and a surfactant within a quantitative or qualitative range that does not depart from the scope of the present invention.

Also, the curable resin composition of the present embodiment may contain an inorganic material such as glass, metal, or silica stone or an organic material such as a synthetic resin. In the case where the inorganic material or the organic material is contained in the curable resin composition, a silane coupling agent is preferably added to a product obtained by the addition reaction of the hydrogen polysiloxane (a1) represented by the general formula (11), the optional hydrogen polysiloxane (a2) having one or more hydrogen atom(s) directly bonded to silicon atom(s),
i) the vinyl group-containing organopolysiloxane (b1) having two or more vinyl groups directly bonded to silicon atoms, or the polysiloxane (b2) having two or more hydroxy groups directly bonded to silicon atoms, and
ii) the organic compound (c) having two or more unsaturated bonds in one molecule
in the step of producing the organopolysiloxane constituting the curable resin composition.

The silane coupling agent is not particularly limited as long as the compound has, in one molecule, a reactive group that chemically binds to the inorganic material such as glass, metal, or silica stone and/or a reactive group that chemically binds to the organic material such as a synthetic resin or a substituent that is highly compatible with the organic material.

Examples of the reactive group that chemically binds to the inorganic material include a methoxy group and an ethoxy group.

Examples of the reactive group that chemically binds to the organic material include a vinyl group, an epoxy group, an amino group, a methacryl group, an acryl group, a mercapto group, and an isocyanato group.

Examples of the substituent that is highly compatible with the organic material include an isocyanurate group. Specific examples of the silane coupling agent include, but not particularly limited to, vinyltrimethoxysilane (KBM-1003, manufactured by Shin-Etsu Chemical Co., Ltd.), vinyltriethoxysilane (KBE-1003, manufactured by Shin-Etsu Chemical Co., Ltd.), 2-(3,4-epoxycyclohexyl)ethyltrimethoxysilane (KBM-303, manufactured by Shin-Etsu Chemical Co., Ltd.), 3-glycidoxypropylmethyldimethoxysilane (KBM-402, manufactured by Shin-Etsu Chemical Co., Ltd.), 3-glycidoxypropyltrimethoxysilane (KBM-403, manufactured by Shin-Etsu Chemical Co., Ltd.), 3-glycidoxypropylmethyldiethoxysilane (KBE-402, manufactured by Shin-Etsu Chemical Co., Ltd.), 3-glycidoxypropyltriethoxysilane (KBE-403, manufactured by Shin-Etsu Chemical Co., Ltd.), p-styryltrimethoxysilane (KBM-1403, manufactured by Shin-Etsu Chemical Co., Ltd.), 3-methacryloxypropylmethyldimethoxysilane (KBM-502, manufactured by Shin-Etsu Chemical Co., Ltd.), 3-methacryloxypropyltrimethoxysilane (KBM-503, manufactured by Shin-Etsu Chemical Co., Ltd.), 3-methacryloxypropylmethyldiethoxysilane (KBE-502, manufactured by Shin-Etsu Chemical Co., Ltd.), 3-methacryloxypropyltriethoxysilane (KBE-503, manufactured by Shin-Etsu Chemical Co., Ltd.), 3-acryloxypropyltrimethoxysilane (KBM-5103, manufactured by Shin-Etsu Chemical Co., Ltd.), N-2-(aminoethyl)-3-aminopropylmethyldimethoxysilane (KBM-602, manufactured by Shin-Etsu Chemical Co., Ltd.), N-2-(aminoethyl)-3-aminopropyltrimethoxysilane (KBM-603, manufactured by Shin-Etsu Chemical Co., Ltd.), 3-aminopropyltrimethoxysilane (KBM-903, manufactured by Shin-Etsu Chemical Co., Ltd.), 3-aminopropyltriethoxysilane (KBE-903, manufactured by Shin-Etsu Chemical Co., Ltd.), 3-triethoxysilyl-3-N-(1,3-dimethyl-butylidene)propylamine (KBE-9103, manufactured by Shin-Etsu Chemical Co., Ltd.), N-phenyl-3-aminopropyltrimethoxysilane (KBM-573, manufactured by Shin-Etsu Chemical Co., Ltd.), N-(vinylbenzyl)-2-aminoethyl-3-aminopropyltrimethoxysilane hydrochloride (KBM-575, manufactured by Shin-Etsu Chemical Co., Ltd.), 3-ureidopropyltriethoxysilane (KBE-585, manufactured by Shin-Etsu Chemical Co., Ltd.), 3-mercaptopropylmethyldimethoxysilane (KBM-802, manufactured by Shin-Etsu Chemical Co., Ltd.), 3-mercaptopropyltrimethoxysilane (KBM-803, manufactured by Shin-Etsu Chemical Co., Ltd.), bis(triethoxysilylpropyl)tetrasulfide (KBE-846, manufactured by Shin-Etsu Chemical Co., Ltd.), 3-isocyanatopropyltriethoxysilane (KBE-9007, manufactured by Shin-Etsu Chemical Co., Ltd.), and tris-(3-trimethoxysilylpropyl)isocyanurate (X-12-965, manufactured by Shin-Etsu Chemical Co., Ltd.).

These silane coupling agents may be used alone or in combination of two or more thereof.

The content of the silane coupling agent in the curable resin composition of the present embodiment is preferably 0.5 to 10 parts by mass based on 100 parts by mass of the organopolysiloxane.

The content of the silane coupling agent of 0.5 parts by mass or more offers excellent adhesion. The content of 10 parts by mass or less offers excellent thermal yellowing resistance. The content of the silane coupling agent is more preferably 0.7 parts by mass or more and 8 parts by mass or less, further preferably 1 part by mass or more and 5 parts by mass or less, from such a viewpoint.

In the case of using the hydrosilylation reaction catalyst (d) in the step of performing the addition reaction for the organopolysiloxane, the curable resin composition of the present embodiment may contain 0.001 parts by mass or less of the hydrosilylation reaction catalyst (d) based on 100 parts by mass of the organopolysiloxane.

The hydrosilylation reaction catalyst (d) can be removed, as mentioned above, using an adsorbent such as active alumina or active carbon after the addition reaction for the organopolysiloxane.

The content of the hydrosilylation reaction catalyst (d) is preferably 0.001 parts by mass or less, more preferably 0.0008 parts by mass or less, further preferably 0.0005 parts by mass or less, from the viewpoint of thermal yellowing resistance and light resistance.

Also, the curable resin composition of the present embodiment may contain a filler typified by an inorganic oxide, if necessary, in the organopolysiloxane of the present embodiment, for the purpose of, for example, improving thermal yellowing resistance, light resistance, hardness, conductivity, thermal conductivity, thixotropy, and low thermal expansion.

Examples of the filler include: inorganic oxides or inorganic nitrides such as silica (e.g., fumed silica, colloidal silica, and precipitated silica), silicon nitride, boron nitride, alumina, zirconia, titania, and barium titanate; and glass, ceramics, silver powders, gold powders, and copper powders.

The filler may or may not be surface-treated for use. The surface-treated filler is industrially preferred because the resulting curable resin composition can have increased flowability and an enhanced filling rate.

Examples of the surface-treated fine particles of the inorganic filler include methoxylated, trimethylsilylated, octylsilylated, or silicone oil-surface-treated particles.

The content of the inorganic oxide in the curable resin composition of the present embodiment is 0.1 to 500 parts by mass based on 100 parts by mass of the organopolysiloxane.

[Cured Product]

The curable resin composition of the present embodiment is in a liquid or solid state before curing and can be subjected to predetermined treatment to thereby prepare a cured product.

For example, the curable resin composition containing the thermal radical generator is subjected to heat treatment to obtain a cured product. The curing temperature is usually 100 to 250° C.

Methods for curing and molding the curable resin composition are not particularly limited. The curable resin composition in a liquid state can be molded by, for example, casting, low-pressure transfer molding, potting, dipping, pressing, or injection molding.

The curable resin composition in a solid state can be molded by thermal curing under pressure using a pressing machine, a low-pressure transfer molding machine, or the like.

The cured product of the curable resin composition of the present embodiment is preferably used as a sealing material for optical semiconductor devices.

The curable resin composition of the present embodiment can also be used as a die bonding paste, while its cured product can be used as a die bonding material.

Furthermore, the cured product of the curable resin composition of the present embodiment can be used preferably as a coating material with which a chip is covered, a lens material, or the like, for use in optical semiconductor devices.

In this case, examples of the optical semiconductor include LED lamps, chip LEDs, semiconductor lasers, photocouplers, and photodiodes.

The optical semiconductor device comprising the cured product of the curable resin composition of the present embodiment as an optical semiconductor sealing material comprises: a housing; a silicon chip disposed in the housing; and a sealing material that is the cured product of the curable resin composition of the present embodiment and seals the silicon chip.

Examples of a material for the housing include, but not particularly limited to, aromatic polyamide such as polyphthalamide, engineering plastics such as nylon 66, and ceramics. The polyphthalamide exhibits particularly high adhesion.

The housing containing glass fiber is preferred because of its high bonding strength. The content of the glass fiber is preferably 5 to 40% by mass, more preferably 10 to 30% by mass, particularly preferably 15 to 25% by mass, based on the mass of the housing. The content of the glass fiber within the range of these numeric values more markedly exerts adhesion.

The curable resin composition of the present embodiment is in a liquid or solid state before curing, as mentioned above. The curable resin composition containing the predetermined photo-radical generator can be irradiated with energy beams such as ultraviolet rays to thereby prepare a cured product.

The curable resin composition containing the photo-radical generator is also preferably used as a coating material for resin films, substrates, or the like, required to be cured at a high rate without heating.

Examples thereof include coating materials for antireflection film formation that are used in flat panel displays (FPDs) or the like.

Particularly, the curable resin composition used as the coating material for antireflection film formation preferably contains porous fine particles having pores, for forming a cured film having a refractive index of 1.4 or lower.

Examples of the porous fine particles include silica particles having an average particle size of 5 nm to 1 μm. The porous fine particles are preferably silica particles having an average particle size of 5 to 100 nm from the viewpoint of the transparency of the cured film. Specific examples of commercially available products thereof include "Aerosil" (trade name, manufactured by Nippon Aerosil Co., Ltd.), which is hydrophilically treated or hydrophobically surface-treated fumed silica, and "Snowtex PS" (trade name, manufactured by Nissan Chemical Industries, Ltd.), which is a pearl necklace-like silica sol containing linearly linked silica particles. These porous fine particles are preferably used by addition in the range of 10 to 70 parts by mass in total of the porous fine particles based on 100 parts by mass of the curable resin composition. Preferably, the porous fine particles are uniformly dispersed in the curable resin composition using a homogenizer or the like.

In the case of using the curable resin composition of the present embodiment as a coating material, examples of methods for forming a cured film include methods involving applying the coating material comprising the curable resin composition of the present embodiment onto the surface of a transparent base material (e.g., resin base materials such as polymethyl methacrylate, polycarbonate, polystyrene, and triacetylcellulose, and inorganic materials such as glass) and light-curing the coating film to thereby form a cured film having a thickness of 10 nm to 1 μm, such as an antireflection film or a scratch-resistant film.

The application onto a base material requires forming a relatively thin film with high precision and thus employs, for example, a micro-gravure, roll coat, flow coat, spin coat, die coat, cast transfer, or spray coat method.

If necessary, the curable resin composition may be diluted with a solvent or the like for adjusting viscosity or may be used in the form of a sol containing porous fine particles or the like. The curable resin composition diluted with a solvent or the like or used in the form of a sol containing porous fine particles or the like may be heated at 50 to 150° C. for a few minutes before curing in order to volatilize the solvent component beforehand.

A colorant can be added to the curable resin composition of the present embodiment to thereby prepare a curable ink.

Various organic and inorganic pigments may be used as the colorant. Examples thereof include: white pigments such as titanium oxide, zinc oxide, white lead, lithopone, and antimony oxide; black pigments such as aniline black, iron black, and carbon black; yellow pigments such as chrome yellow, yellow iron oxide, Hanza yellow (100, 50, 30, etc.), titan yellow, benzine yellow, and permanent yellow; orange pigments such as chrome vermilion, permanent orange, Vulcan fast orange, and indanthrene brilliant orange; brown pigments such as iron oxide, permanent brown, and para brown; red pigments such as colcothar, cadmium red, antimony vermilion, permanent red, rhodamine lake, alizarin lake, thioindigo red, PV-carmine, Monolite fast red, and quinacridone-based red pigments; violet pigments such as cobalt violet, manganese violet, fast violet, methyl violet lake, indanthrene brilliant violet, and dioxazine violet; blue pigments such as ultramarine, iron blue, cobalt blue, alkali blue lake, metal-free phthalocyanine blue, copper phthalocyanine blue, indanthrene blue, and indigo; green pigments such as chrome green, chromium oxide, emerald green, naphthol green, green gold, acid green lake, malachite green lake, phthalocyanine green, and polychlorobromocopper phthalocyanine; and other various fluorescent pigments, metallic flake pigments, and extender pigments. The amount of the colorant is preferably 1 to 50% by mass, more preferably 5 to 25% by mass, based on the total amount of the curable resin composition.

In addition to the colorant, a pigment dispersant may be used, if necessary, in the curable ink.

Examples of the pigment dispersant include: activators such as higher fatty acid salt, alkyl sulfate, alkyl ester sulfate, alkyl sulfonate, sulfosuccinate, naphthalene sulfonate, alkyl phosphate, polyoxyalkylene alkyl ether phosphate, polyoxyalkylene alkylphenyl ether, glycerin ester, sorbitan ester, and polyoxyethylene fatty acid amide; block copolymers or random copolymers composed of two or more monomers selected from styrene, styrene derivatives, vinylnaphthalene derivatives, acrylic acid, acrylic acid derivatives, maleic acid, maleic acid derivatives, itaconic acid, itaconic acid derivatives, fumaric acid, and fumaric acid derivatives; and salts thereof.

Examples of methods for dispersing the colorant in the curable ink include methods using various dispersing machines such as ball mills, sand mills, attritors, roll mills, agitators, Henschel mixers, colloid mills, ultrasound homogenizers, pearl mills, wet jet mills, and paint shakers.

The curable ink may be subjected to predetermined treatment using a centrifuge or a filter for the purpose of removing a coarse-grained fraction of the dispersed pigment in the curable ink.

In the case of using a pigment ink as the colorant, the average particle size of pigment particles in the pigment ink is selected in consideration of stability in the curable ink, image density, luster, light resistance, etc. Preferably, the average particle size of pigment particles is appropriately selected from the viewpoint of improvement in luster and improvement in texture.

The curable resin composition of the present embodiment is also preferably used in lens materials such as lenses for eyewear, lenses for optical instruments, lenses for CD or DVD pickup, lenses for automobile headlamps, and lenses for projectors, and various optical elements such as optical fibers, optical waveguides, light filters, optical adhesives, optical disk substrates, display substrates, and curable resins for nanoimprint, by exploiting its thermal yellowing resistance or high transparency.

The curable resin composition of the present embodiment can also be used as a sealing material for optical semiconductors, while its cured product is suitable as a transparent resin for semiconductor packages. Such a semiconductor package is obtained by molding the sealing material for optical semiconductors.

The sealing material for optical semiconductors is formed by the direct coating of a primer-treated object after plasma treatment using a coating apparatus such as a dispenser or a spinner.

The thus-applied sealing material for optical semiconductors may be cured or cured using a molding machine or the like.

EXAMPLES

Hereinafter, the present invention will be described with reference to specific Examples and Comparative Examples. However, the present invention is not limited by Examples below.

In Examples and Comparative Examples, measurement and evaluation were performed by the following methods:

<(1) Calculation of Rate of Reaction of SiH>

0.05 g of each sampled reaction solution (solution collected after a lapse of 72 hours from the start of the reaction from each reaction solution for organopolysiloxane synthesis in Examples and Comparative Examples described later) was dissolved in 1 g of a deuterated chloroform solvent to prepare a measurement sample.

$^1$H NMR measurement was performed with 100 transients at 400 MHz (α-400 manufactured by JASCO Corp.) using this measurement sample. The obtained results were analyzed.

The rate of reaction of SiH was calculated according to the formula shown below from the area ratios between Si—$CH_3$-derived peaks at 0.2 ppm and SiH-derived peaks at 4.6 ppm determined before and after the reaction.

A sample having 98% higher rate of reaction of SiH was evaluated as being excellent; a sample having 90% or higher and less than 98% rate of reaction of SiH was evaluated as being good; and a sample having less than 90% rate of reaction of SiH was evaluated as being poor.

$$\text{Rate of reaction of SiH (\%)} = [((X1-Y1)/X1] \times 100$$

X1: Peak Area Ratio Before the Reaction (Peak area of SiH before the reaction)/(Peak area of Si—$CH_3$ before the reaction)

Y1: Peak Area Ratio after the Reaction (Peak area of SiH after the reaction)/(Peak area of Si—$CH_3$ after the reaction)

<(2) Identification of Molecular Structure>

Each of samples of organopolysiloxanes (A1) to (A17) prepared in Examples and Comparative Examples described later was dissolved at a ratio of 20 mg to 1 g in a deuterated chloroform solvent, and the resulting solution was used as a measurement sample. $^1$H NMR measurement was performed with 200 transients in α-400 (manufactured by JASCO Corp.) using this measurement sample. The obtained results were analyzed.

Each sample was dissolved at a ratio of 0.3 g to 1 g in a deuterated chloroform solvent, and the resulting solution was used as a measurement sample. $^{13}$C NMR measurement was performed with 20000 transients in α-400 (manufactured by JASCO Corp.) using this measurement sample. The obtained results were analyzed.

Each sample was dissolved at a ratio of 0.15 g to 1 g in a deuterated chloroform solvent and supplemented with 8% by mass (based on silicone) of Cr(acac)$_3$, and the resulting solution was used as a measurement sample. $^{29}$Si NMR measurement was performed with 4000 transients in α-400 (manufactured by JASCO Corp.) using this measurement sample. The obtained results were analyzed.

The results obtained by $^1$H NMR, $^{13}$C NMR, and $^{29}$Si NMR were analyzed to identify the molecular structures of the organopolysiloxanes (A1) to (A17).

<(3) Calculation of Functional Group Equivalent Weight of (Meth)Acryloxy Group>

Each of samples of organopolysiloxanes (A1) to (A17) prepared in Examples and Comparative Examples described later was dissolved at a ratio of 30 mg to 1 g in a deuterated chloroform solvent, and the resulting solution was used as a measurement sample. $^1$H NMR measurement was performed with 200 transients in α-400 (manufactured by JASCO Corp.) using this measurement sample. The obtained results were analyzed to determine the average composition of one organopolysiloxane molecule.

Each sample was dissolved at a ratio of 0.15 g to 1 g in a deuterated chloroform solvent and supplemented with 8% by mass (based on silicone) of Cr(acac)$_3$, and the resulting solution was used as a measurement sample. $^{29}$Si NMR measurement was performed with 4000 transients in α-400 (manufactured by JASCO Corp.) using this measurement sample. The obtained results were analyzed to determine the average composition of one organopolysiloxane molecule.

The results obtained by $^1$H NMR and $^{29}$Si NMR were analyzed to calculate the functional group equivalent weight (mass per mol of functional groups) of (meth)acryloxy groups.

<(4) Calculation of Weight-Average Molecular Weight>

Each of samples for measurement of organopolysiloxanes (A1) to (A17) prepared in Examples and Comparative Examples described later was dissolved at a ratio of 100 mg to 2 g in a chloroform solvent and filtered through a 0.45-μm filter to prepare a measurement sample solution.

An eluent (chloroform) was applied under flow rate conditions of 1 mL/min. to a column [the column was constituted by Tsk guard column Hhr-H (registered trademark) (manufactured by Tosoh Corp.) as a gourd column with one each of columns Tskgel (registered trademark) G5000Hhr (manufactured by Tosoh Corp.), Tskgel (registered trademark) G3000Hhr (manufactured by Tosoh Corp.), and Tskgel (registered trademark) G1000Hhr (manufactured by Tosoh Corp.) arranged in series] with a column temperature of 40° C. A calibration curve was determined and prepared in advance from elution times in the RI detection of monodisperse polystyrene standards (manufactured by Polymer Laboratories Ltd.) having a known molecular weight of 7,500,000, 2,560,000, 841,700, 320,000, 148,000, 59,500, 28,500, 10,850, 2,930, or 580 and a styrene monomer (molecular weight: 104).

The molecular weight was calculated using the calibration curve from the elution time and detection intensity of the measurement sample solution.

<(5) Viscosity Measurement>

The viscosity of each of samples for measurement of organopolysiloxanes (A1) to (A17) prepared in Examples and Comparative Examples described later was measured at a temperature of 25° C. using TVE-22H manufactured by Toki Sangyo Co., Ltd.

<(6) Calculation of Ratio ([WB]/[WA]) of Content [WB] of Compound Represented by General Formula (10) to Content [WA] of Compound Represented by General Formula (9)>

The values of [WA] and [WB] represent the intensities of peaks corresponding to the total sums of the masses of the structures of the general formulas (9) and (10), respectively, and the mass 23 of sodium and are obtained by the matrix-assisted laser desorption/ionization time-of-flight mass spectrometry (hereinafter, referred to as MALDI-TOF/MS) measurement of the organopolysiloxane.

The masses of the structures of the general formulas (9) and (10) refer to values calculated using the mass of the most abundant isotope among the masses of isotopes of each element in the case where elements constituting the structures have isotopes.

If there existed a plurality of peaks corresponding to the general formula (9) or (10), the content [WA] of the compound having the structure of the general formula (9) or the content [WB] of the compound represented by the general formula (10) was defined as the total value of the intensities of the peaks corresponding to the structure.

In this context, the intensity of a peak having intensity of 3% or lower based on the maximum intensity of a peak corresponding to the total sum of the mass of the structure of the general formula (9) or (10) and the mass 23 of sodium was excluded from the calculation of the total value of the peak intensities.

The MALDI-TOF/MS measurement was performed by the following method:

<Method for MALDI-TOF/MS Measurement>

0.1 g each of the organopolysiloxanes (A5), (A6), (A11), and (A12) prepared in Examples and Comparative Examples described later was dissolved in 100 mL of tetrahydrofuran at room temperature. This solution was uniformly mixed at a ratio of 1:1 by volume at room temperature with a solution containing 10 mg of dithranol dissolved in 1 mL of tetrahydrofuran to prepare a solution a. Subsequently, 10 mg of sodium iodide was dissolved in 10 mL of acetone, and 1 μL of the solution was placed on a sample plate. 1 μL of the solution a was added dropwise thereto. The solvent was evaporated at room temperature. Then, the sample was measured by MALDI-TOF/MS under the following measurement conditions:

(Measurement Condition)
Apparatus: AXIMA CFRplus manufactured by Shimadzu Corp.
Laser: Nitrogen laser (337 nm)
Detector mode: Linear mode
Ion detection: Cation (positive mode)
The number of transients: 500

<(7) Thermal Yellowing Resistance>

A cured product having a thickness of 3 mm was used as each of samples for measurement of cured products prepared in Examples and Comparative Examples described later. Its yellowness index (YI) was measured using a spectrocolorimeter CM-3600d (trade name) manufactured by Konica Minolta, Inc.

Next, the cured product was wrapped in aluminum foil and heat-treated at 150° C. for 150 hours in air. Then, its yellowness index (YI) was measured again using a spectrocolorimeter CM-3600d (trade name) manufactured by Konica Minolta, Inc.

Change in YI between before and after this heat treatment was defined as ΔYI. A sample having ΔYI less than 1.0 was evaluated as being excellent; a sample having ΔYI of 1.0 or more and less than 3.0 was evaluated as being good; and a sample having ΔYI of 3.0 or more was evaluated as being poor.

<(8) Light Resistance>

A cured product having a thickness of 3 mm was used as each of samples for measurement of cured products prepared in Examples and Comparative Examples described later. Its yellowness index (YI) was measured using a spectrocolorimeter CM-3600d (trade name) manufactured by Konica Minolta, Inc.

Next, the cured product was loaded in a constant-temperature dryer set to a constant temperature of 50° C. and irradiated with an illuminance of 4 W/cm² at 365 nm for 100 hours using a UV irradiation apparatus (manufactured by Ushio Inc., trade name: SP-7) equipped with a 365-nm band-pass filter.

Then, its yellowness index (YI) was measured again using a spectrocolorimeter CM-3600d (trade name) manufactured by Konica Minolta, Inc. Change in YI between before and after this UV irradiation was defined as ΔYI. A sample having ΔYI less than 1.0 was evaluated as being excellent; a sample having ΔYI of 1.0 or more and less than 3.0 was evaluated as being good; and a sample having ΔYI of 3.0 or more was evaluated as being poor.

<(9) Heat and Cold Shock Resistance>

A 5 mm×5 mm×0.2 mm silicon chip was placed in a housing which was a molded 20 mm×20 mm×2 mm flat plate of polyphthalamide resin (Amodel 4122 manufactured by Solvay Specialty Polymers Japan K.K.) provided with 10 mmφ depression with a depth of 1 mm in the center thereof.

Next, each of curable resin compositions prepared in Examples 1 to 17 and Comparative Examples 1 to 6 was casted thereto and heat- or light-cured to form a cured product (sealing material) for sealing a silicon chip. This product was used as a test piece of an optical semiconductor device.

The obtained test piece was visually observed to confirm the number of cycles (each involving room temperature→−40° C. (15 min.)→120° C. (15 min.)→room temperature in a small heat and cold shock apparatus TSE-11 manufactured by Espec Corp.) at which exfoliation occurred.

A sample having no exfoliation even after 100 or more cycles was evaluated as being excellent; a sample in which exfoliation occurred at 50 or more and less than 100 cycles was evaluated as being good; and a sample in which exfoliation occurred at less than 50 cycles was evaluated as being poor.

<(10) Hardness>

A 35 mm long×8 mm wide×2 mm thick cured product was used as each of samples for measurement of cured products prepared in Examples and Comparative Examples described later. Its dynamic viscoelasticity was measured from −120° C. to 150° C. (temperature rising rate: 2° C./min.) using MCR-301 manufactured by Anton Paar GmbH.

In terms of hardness, a sample having a G' (storage elastic modulus) value of $10^7$ or larger at 30° C. was evaluated as being excellent; a sample having a G' value of $10^6$ or larger and smaller than $10^7$ was evaluated as being good; and a sample having a G' value smaller than $10^6$ was evaluated as being poor.

<(11) Adhesion>

Each of curable resin compositions prepared in Examples 1 to 17 and Comparative Examples 1 to 6 was casted to a mold made of a 20 mm×20 mm×2 mm flat plate of polyphthalamide resin (Amodel 4122 manufactured by Solvay Specialty Polymers Japan K.K.) provided with 10 mmφ depression with a depth of 1 mm in the center thereof, and heat- or light-cured to obtain a test piece.

The obtained test piece was visually observed to confirm the number of cycles (each involving room temperature→−40° C. (15 min.)→120° C. (15 min.)→room temperature in a small heat and cold shock apparatus TSE-11 manufactured by Espec Corp.) at which exfoliation occurred.

A sample having no exfoliation even after 100 or more cycles was evaluated as being excellent; a sample in which exfoliation occurred at 50 or more and less than 100 cycles was evaluated as being good; and a sample in which exfoliation occurred at less than 50 cycles was evaluated as being poor.

<(12) Gas Barrier>

A 100 mm×100 mm cured product having a thickness of 0.2 mm was used as each of samples for measurement of cured products prepared in Examples and Comparative Examples described later. Its oxygen transmission rate was measured at a temperature of 23° C. under dry conditions using an oxygen transmission rate measurement apparatus Model 8001 manufactured by Systech Illinois Ltd. A sample having an oxygen transmission rate lower than 500 cc/m²/day was evaluated as being excellent; a sample having an oxygen transmission rate of 500 cc/m²/day or higher and lower than 1000 cc/m²/day was evaluated as being good; and a sample having an oxygen transmission rate of 1000 cc/m²/day or higher was evaluated as being poor.

Example 1

Production of Organopolysiloxane (A1) Having Unsaturated Bond-Containing Group 53 g (0.2 mol) of 1,3,5,7-tetramethylcyclotetrasiloxane as the component (a1), 27 g (0.1 mol) of methyltris(dimethylsiloxy)silane as the component (a2), 242 g (0.3 mol) of vinyldimethylsiloxy-terminated polydimethylsiloxane (weight-average molecular weight: 780) represented by the average composition formula (B1-1) shown below as the component (b1), 101 g (0.9 mol) of 6-vinylbicyclo[2.2.1]hept-2-ene as the component (c)

1600 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

$$CH_2=CHSi(Me)_2O-(Si(Me)_2O)_8-Si(Me)_2CH=CH_2 \quad (B1-1)$$

In the average composition formula (B1-1), Me represents a methyl group (the same holds true for average composition formulas shown in Examples and Comparative Examples in the present specification).

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 98%.

Then, the reaction system was treated with active carbon, and volatile matter was distilled off to obtain 350 g of organopolysiloxane (A1) having an unsaturated bond-containing group represented by the general formula (40) shown below.

The obtained organopolysiloxane (A1) having an unsaturated bond-containing group was free from a (meth)acryloxy group, but had a functional group equivalent weight of the unsaturated bond-containing group of 694 g/mol, a weight-average molecular weight of 37500 calculated by GPC measurement, and a viscosity of 2800 mPa·s at 25° C.

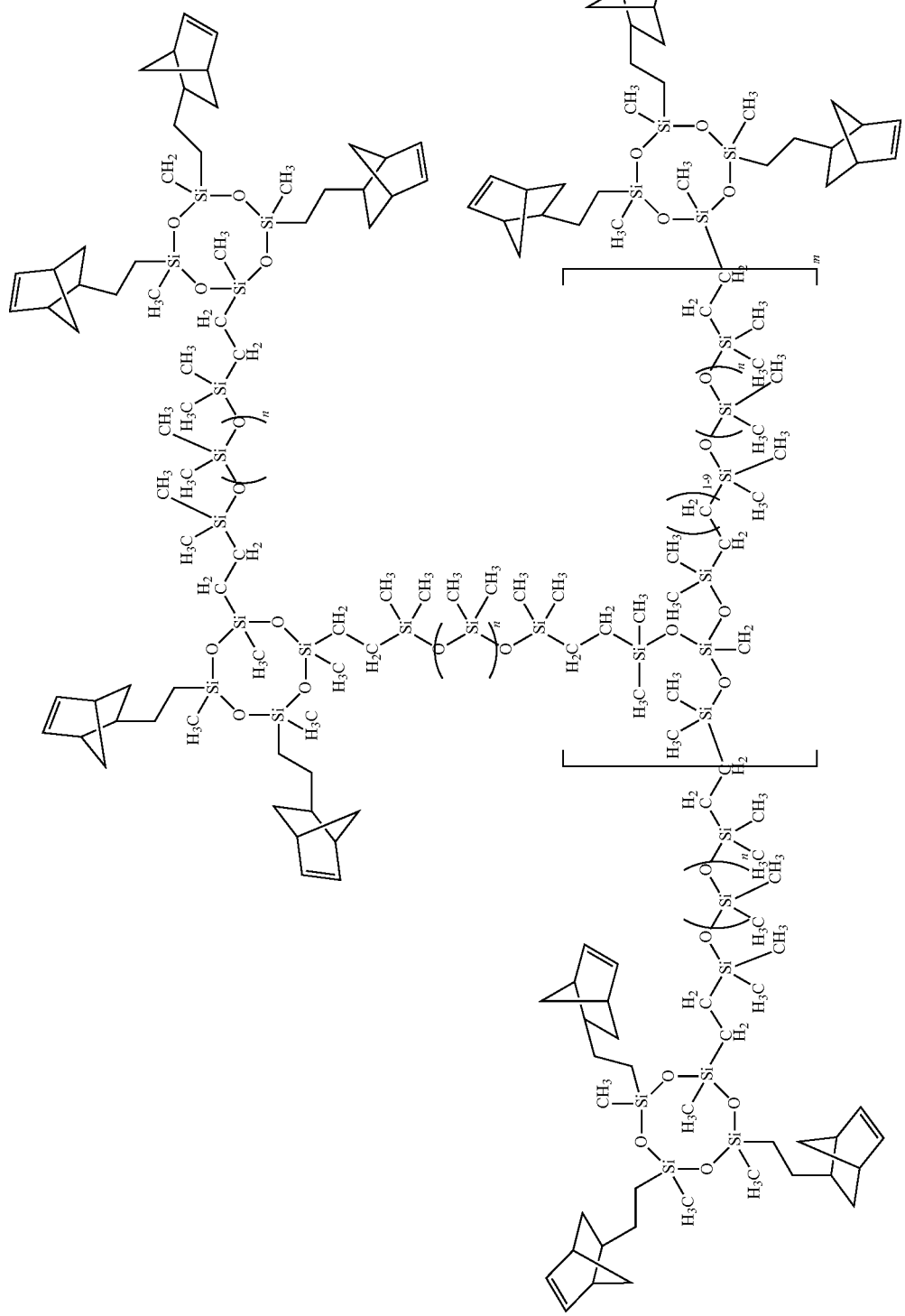
(40)

In the formula (40), m represents an integer of 10 on average, and n represents an integer of 8 on average.

As a result of Si NMR measurement, the following peaks corresponding to the constitutional units were observed:
F1: −17.2 ppm
M1: +8.8 ppm
T: −66.2 ppm
D2: −19.8 ppm
D3: −21.2 ppm
The value of a/(b+c) was 0.78.
S: No peak was observed at −32.3 ppm, and the value of d/a was 0.

<Production of Cured Product and Evaluation of Property>

100 parts by mass of the organopolysiloxane (A1) having an unsaturated bond-containing group were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 2

Production of Methacryloxy Group-Containing Organopolysiloxane (A2)

53 g (0.2 mol) of 1,3,5,7-tetramethylcyclotetrasiloxane as the component (a1), 27 g (0.1 mol) of methyltris(dimethylsiloxy)silane as the component (a2), 242 g (0.3 mol) of vinyldimethylsiloxy-terminated polydimethylsiloxane (weight-average molecular weight: 780) represented by the average composition formula (B1-2) shown below as the component (b1), 118 g (0.9 mol) of 3-butenylmethacrylate as the component (c)

1600 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

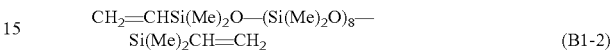

$$CH_2=CHSi(Me)_2O-(Si(Me)_2O)_8-Si(Me)_2CH=CH_2 \quad (B1-2)$$

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 370 g of methacryloxy group-containing organopolysiloxane (A2) represented by the general formula (41) shown below.

The obtained methacryloxy group-containing organopolysiloxane (A2) had a functional group equivalent weight of 714 g/mol, a weight-average molecular weight of 38200 calculated by GPC measurement, and a viscosity of 2600 mPa·s at 25° C.

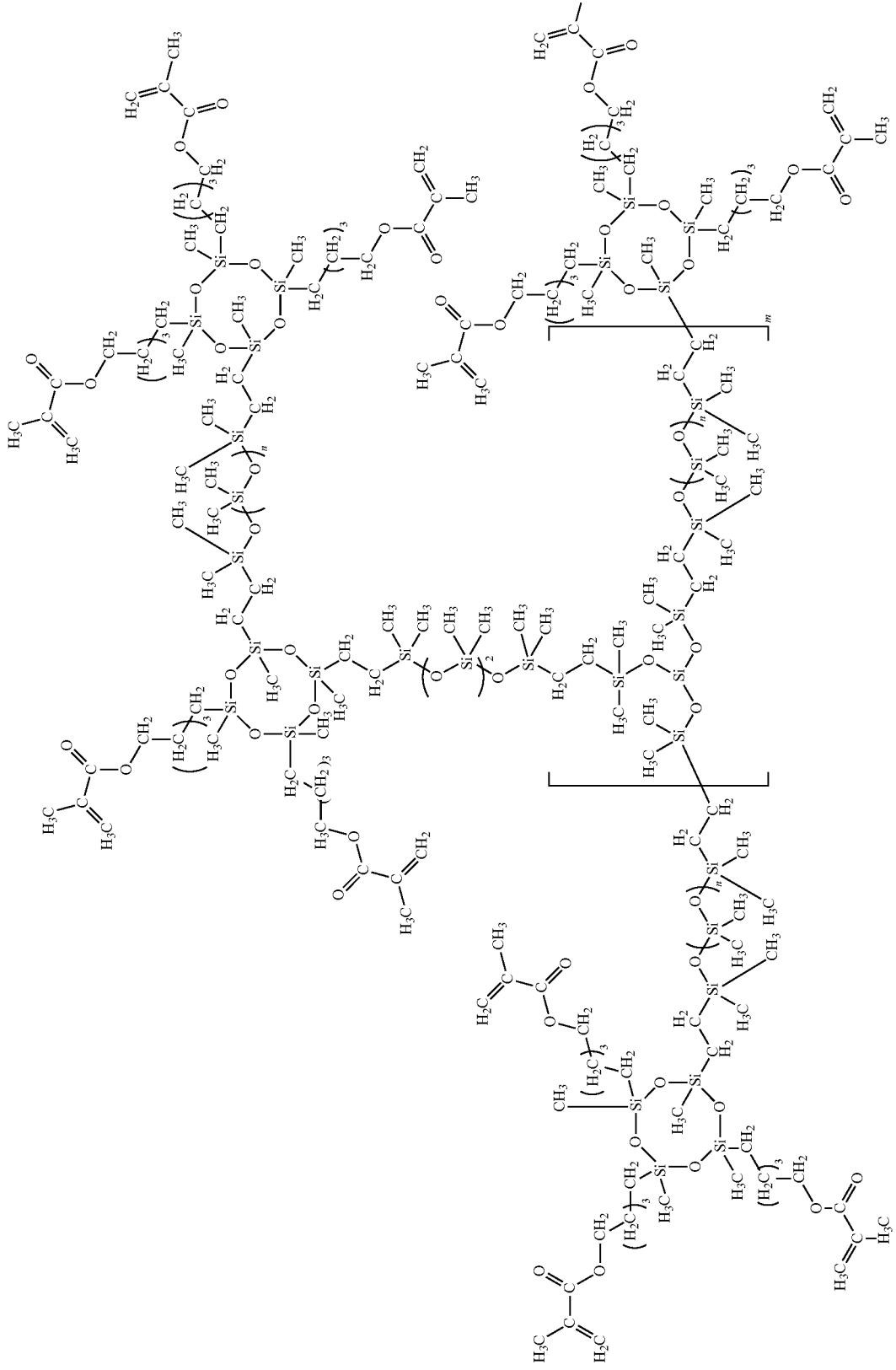

In the formula (41), m represents an integer of 10 on average, and n represents an integer of 8 on average.

As a result of Si NMR measurement, the following peaks corresponding to the constitutional units were observed:
F1: −18.2 ppm
M1: +8.8 ppm
T: −66.2 ppm
D2: −19.8 ppm
D3: −21.2 ppm
The value of a/(b+c) was 0.78.
S: No peak was observed at −32.3 ppm, and the value of d/a was 0.

<Production of Cured Product and Evaluation of Property>

100 parts by mass of the methacryloxy group-containing organopolysiloxane (A2) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 3

Production of Methacryloxy Group-Containing Organopolysiloxane (A3)

53 g (0.2 mol) of 1,3,5,7-tetramethylcyclotetrasiloxane as the component (a1), 16 g (0.05 mol) of tetrakis(dimethylsiloxy)silane as the component (a2), 203 g (0.3 mol) of vinyldimethylsiloxy-terminated polydimethylsiloxane (weight-average molecular weight: 780) represented by the average composition formula (B1-3) shown below as the component (b1), 118 g (0.9 mol) of 3-butenylmethacrylate as the component (c)

1500 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

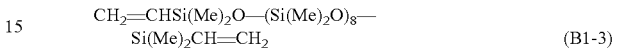

(B1-3)

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 97%.

Then, the reaction system was treated with active carbon, and volatile matter was distilled off to obtain 330 g of methacryloxy group-containing organopolysiloxane (A3) represented by the general formula (42) shown below.

The obtained methacryloxy group-containing organopolysiloxane (A3) had a functional group equivalent weight of 626 g/mol, a weight-average molecular weight of 34200 calculated by GPC measurement, and a viscosity of 3500 mPa·s at 25° C.

(42)
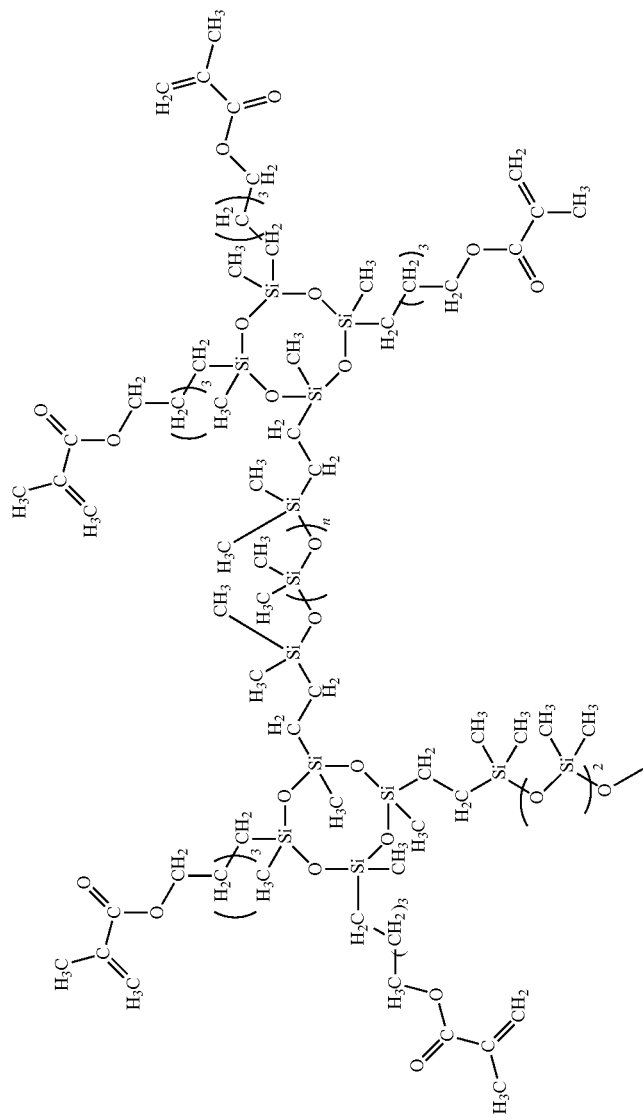

-continued
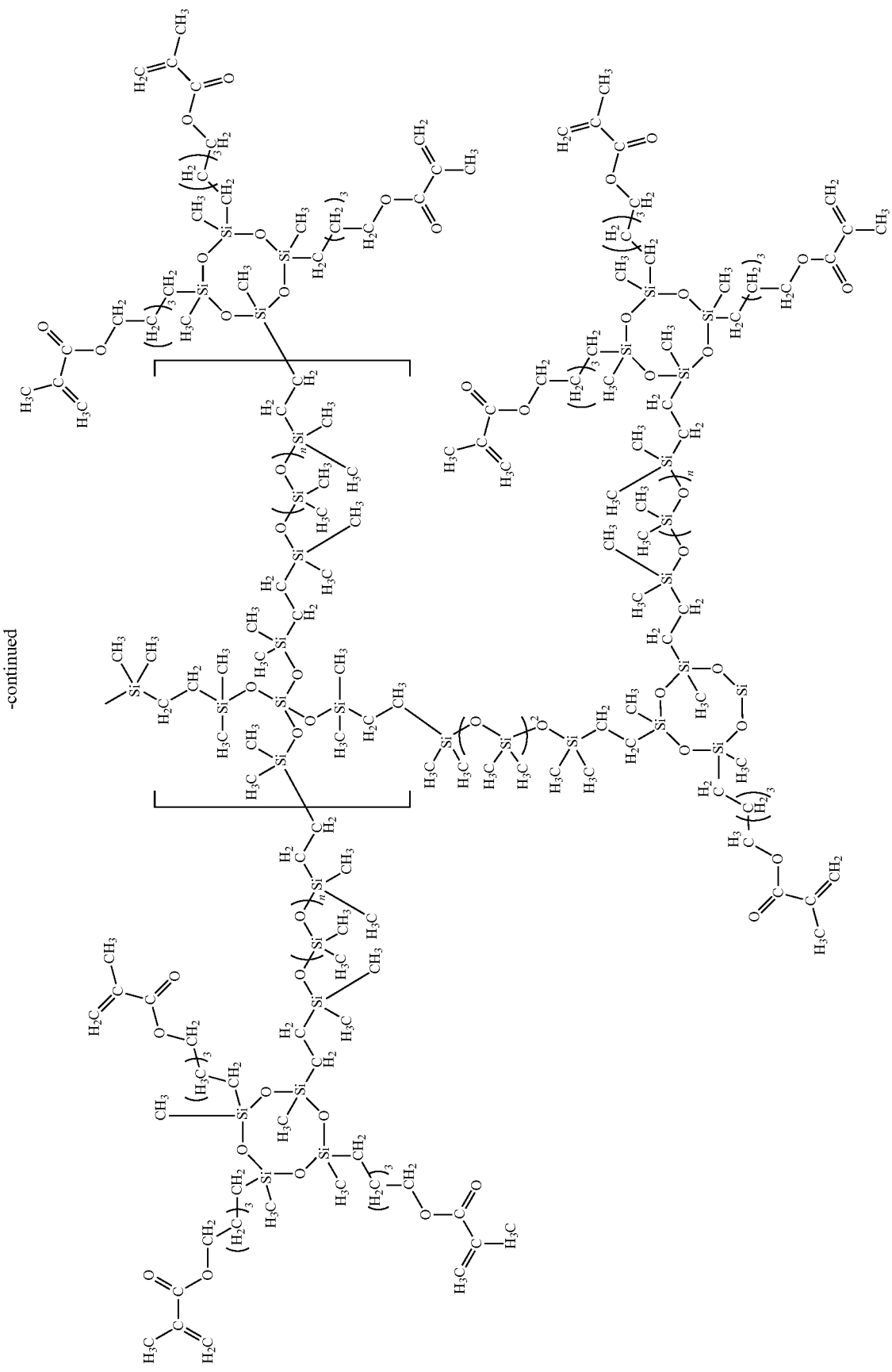

In the formula (42), m represents an integer of 5 on average, and n represents an integer of 8 on average.

As a result of Si NMR measurement, the following peaks corresponding to the constitutional units were observed:

F1: −18.2 ppm
M1: +8.8 ppm
D2: −19.8 ppm
D3: −21.2 ppm
S: −32.3 ppm

The value of a/(b+c) was 1.08, and the value of d/a was 0.08.

<Production of Cured Product and Evaluation of Property>

100 parts by mass of the methacryloxy group-containing organopolysiloxane (A3) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 4

Production of Methacryloxy Group-Containing Organopolysiloxane (A4)

41 g (0.2 mol) of 1,3,5,7-tetramethylcyclotetrasiloxane as the component (a1), 125 g (0.2 mol) of vinyldimethylsiloxy-terminated polydimethylsiloxane (weight-average molecular weight: 780) represented by the average composition formula (B1-4) shown below as the component (b1), 76 g (0.6 mol) of 3-butenylmethacrylate as the component (c)

864 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

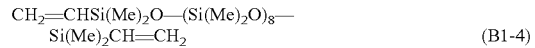

$$CH_2=CHSi(Me)_2O-(Si(Me)_2O)_8-Si(Me)_2CH=CH_2 \quad (B1\text{-}4)$$

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 205 g of methacryloxy group-containing organopolysiloxane (A4) represented by the general formula (43) shown below.

The obtained methacryloxy group-containing organopolysiloxane (A4) had a functional group equivalent weight of 600 g/mol, a weight-average molecular weight of 19800 calculated by GPC measurement, and a viscosity of 4500 mPa·s at 25° C.

(43)
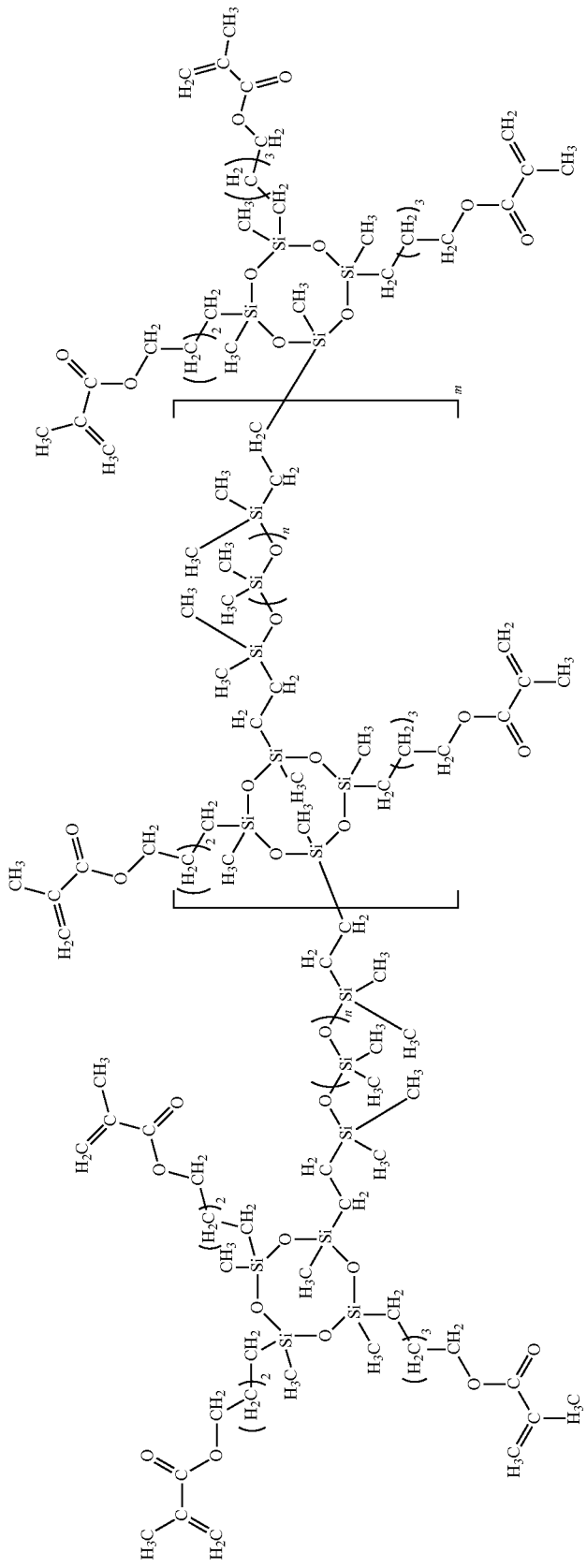

In the formula (43), m represents an integer of 15 on average, and n represents an integer of 8 on average.

As a result of Si NMR measurement, the following peaks corresponding to the constitutional units were observed:
F1: −18.2 ppm
M1: +8.8 ppm
D2: −19.8 ppm
D3: −21.2 ppm
The value of a/(b+c) was 1.13.
S: No peak was observed at −32.3 ppm, and the value of d/a was 0.

<Production of Cured Product and Evaluation of Property>

100 parts by mass of the methacryloxy group-containing organopolysiloxane (A4) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 5

Production of Methacryloxy Group-Containing Organopolysiloxane (A5)

68 g (0.3 mol) of 1,3,5,7-tetramethylcyclotetrasiloxane as the component (a1), 51 g (0.3 mol) of vinyldimethylsiloxy-terminated dimethyldisiloxane (molecular weight: 186) represented by the average composition formula (B1-5) shown below as the component (b1), 119 g (0.9 mol) of 3-butenylmethacrylate as the component (c)

795 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

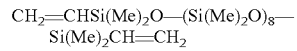

(B1-5)

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 188 g of methacryloxy group-containing organopolysiloxane (A5) represented by the general formula (44), the general formula (45) and the general formula (46) shown below.

The obtained methacryloxy group-containing organopolysiloxane (A5) had a functional group equivalent weight of 350 g/mol, a weight-average molecular weight of 16400 calculated by GPC measurement, and a viscosity of 15000 mPa·s at 25° C.

The obtained methacryloxy group-containing organopolysiloxane (A5) had a [WB]/[WA] value of 1.7. In this context, the general formula (45) corresponds to the general formula (9), and the general formula (46) corresponds to the general formula (10).

(44)
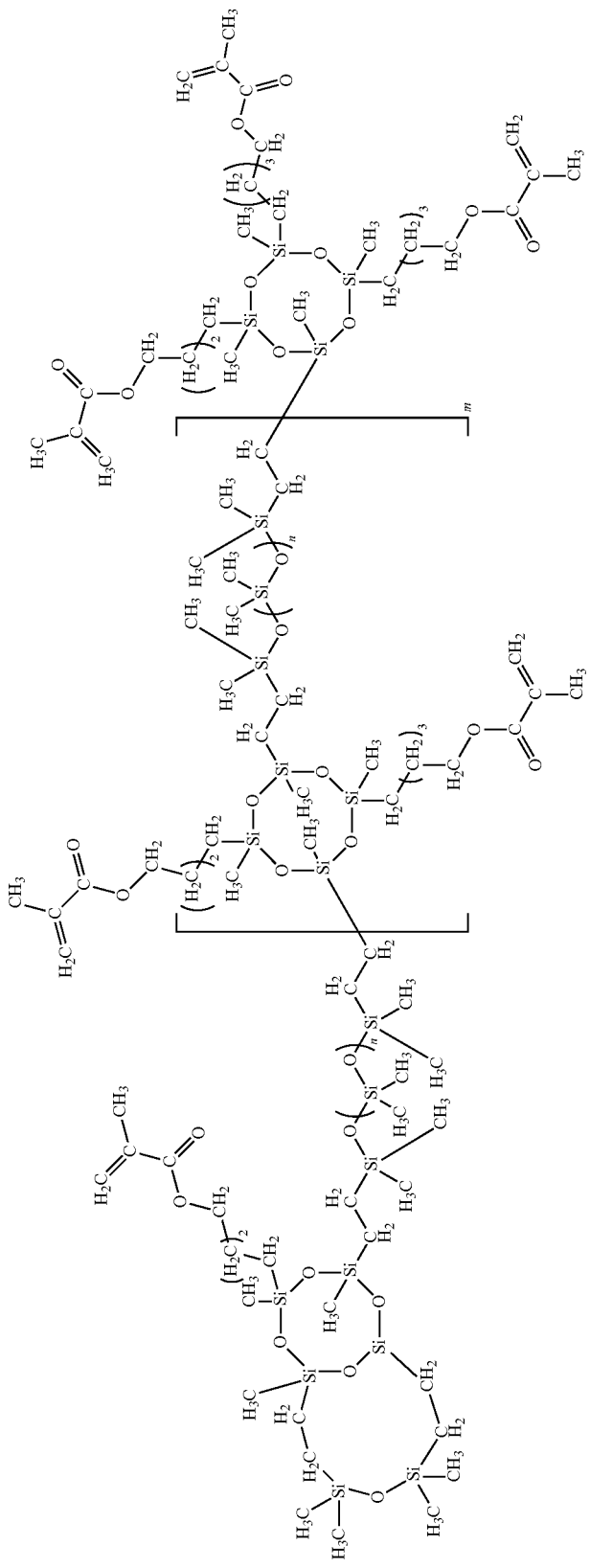

(45)

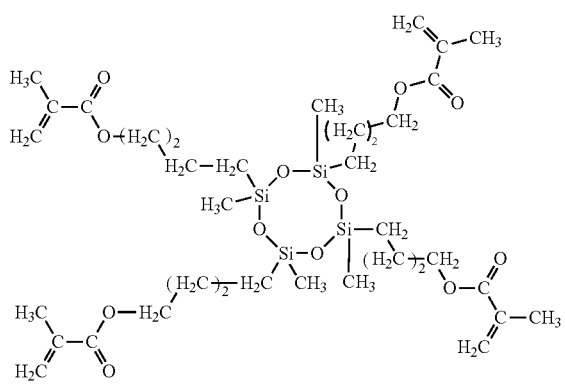

(46)

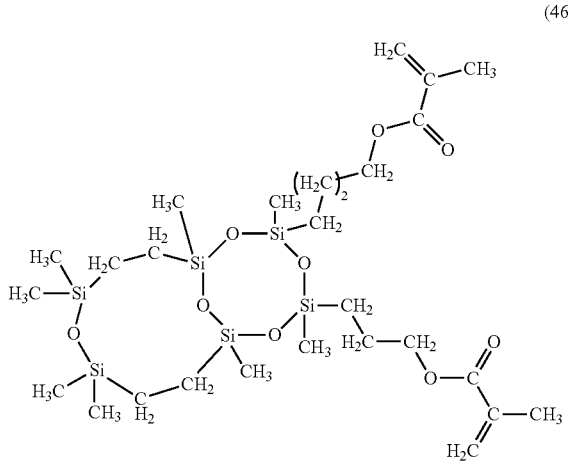

In the formula (44), m represents an integer of 25 on average, and n represents an integer of 0 on average.

As a result of Si NMR measurement, the following peaks corresponding to the constitutional units were observed:

F1: −18.2 ppm
M1: +8.8 ppm
D2: −19.8 ppm

The value of a/(b+c) was 1.04.

S: No peak was observed at −32.3 ppm, and the value of d/a was 0.

<Production of Cured Product and Evaluation of Property>

100 parts by mass of the methacryloxy group-containing organopolysiloxane (A5) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 6

Production of Methacryloxy Group-Containing Organopolysiloxane (A6)

201 g (0.8 mol) of 1,3,5,7-tetramethylcyclotetrasiloxane as the component (a1), 269 g (1.4 mol) of vinyldimethylsiloxy-terminated dimethyldisiloxane (molecular weight: 186) represented by the average composition formula (B1-6) shown below as the component (b1), 97 g (0.7 mol) of 3-butenylmethacrylate as the component (c)

2138 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

$$CH_2=CHSi(Me)_2O—(Si(Me)_2O)_8—Si(Me)_2CH=CH_2 \quad (B1\text{-}6)$$

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 520 g of methacryloxy group-containing organopolysiloxane (A6) represented by the general formula (47), the general formula (48) and the general formula (49) shown below.

The obtained methacryloxy group-containing organopolysiloxane (A6) had a functional group equivalent weight of 1157 g/mol, a weight-average molecular weight of 98600 calculated by GPC measurement, and a viscosity of 26000 mPa·s at 25° C.

The obtained methacryloxy group-containing organopolysiloxane (A6) had a [WB]/[WA] value of 10.1. In this context, the general formula (48) corresponds to the general formula (9), and the general formula (49) corresponds to the general formula (10).

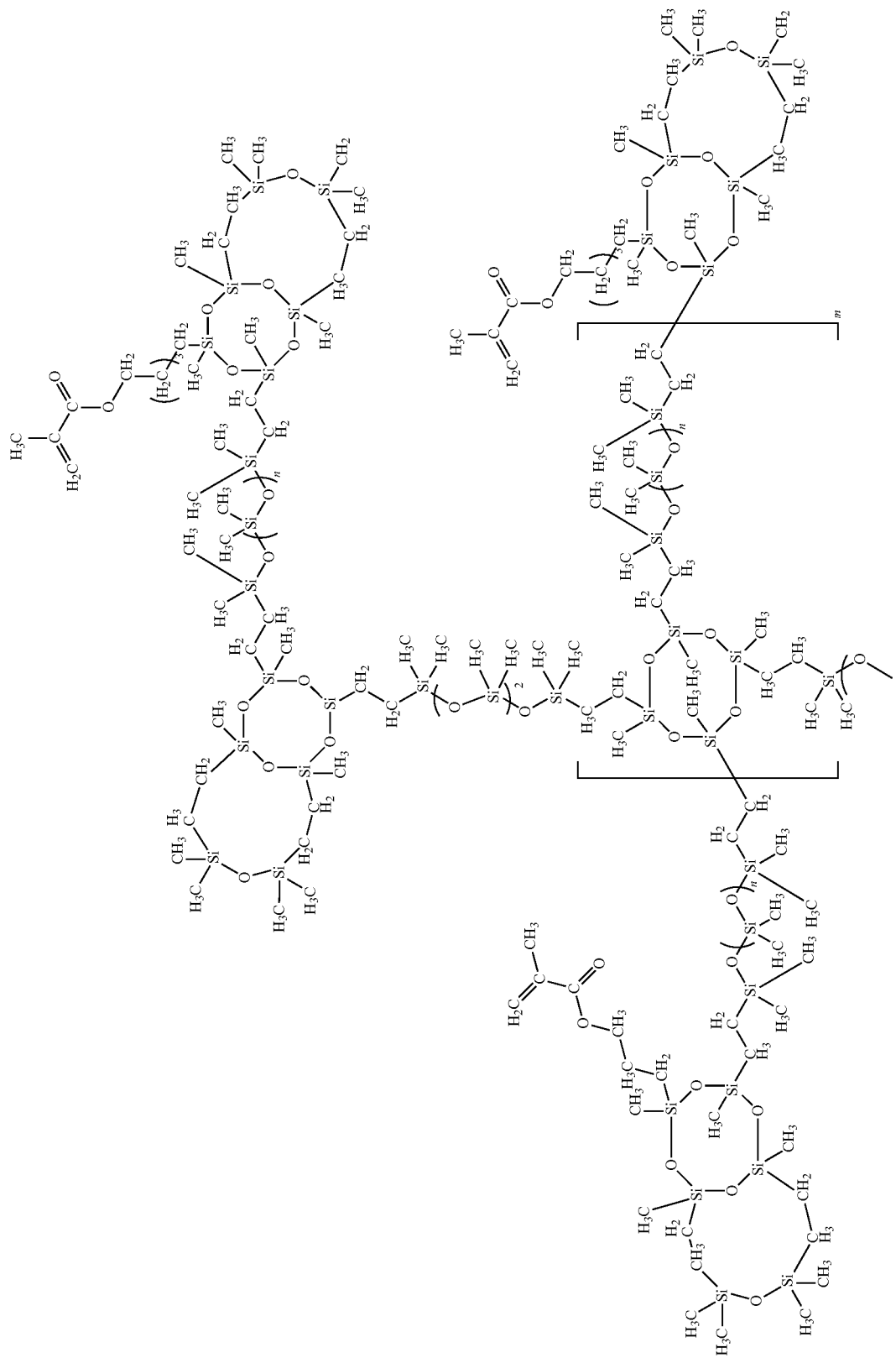

-continued
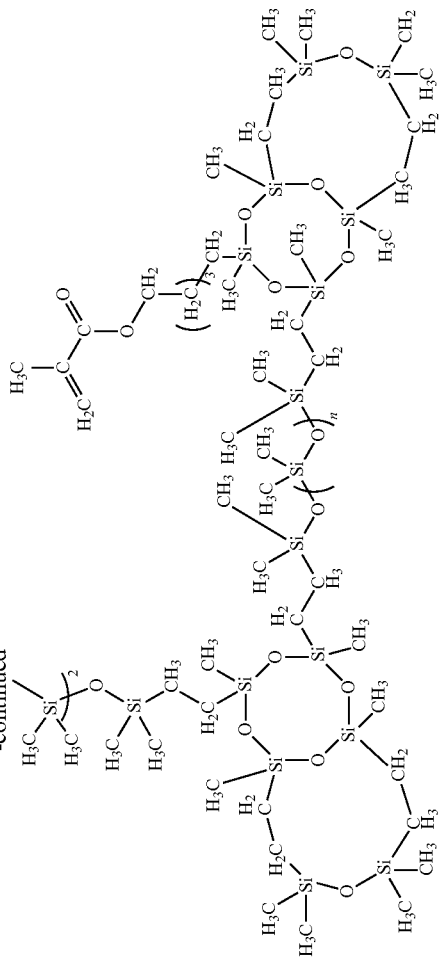

(48)

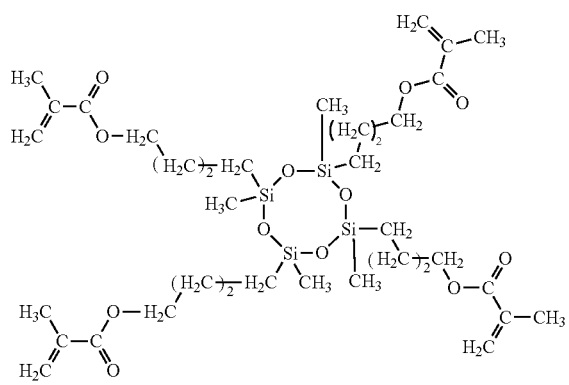

(49)

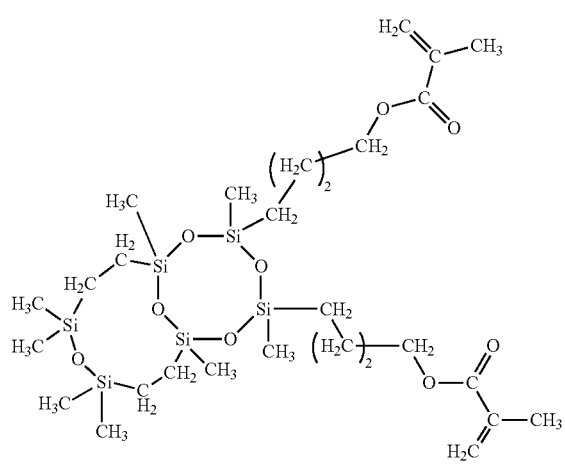

In the formula (47), m represents an integer of 30 on average, and n represents an integer of 0 on average.

As a result of Si NMR measurement, the following peaks corresponding to the constitutional units were observed:

F1: −18.2 ppm

M1: +8.8 ppm

D2: −19.8 ppm

The value of a/(b+c) was 0.16.

S: No peak was observed at −32.3 ppm, and the value of d/a was 0.

<Production of Cured Product and Evaluation of Property>

100 parts by mass of the methacryloxy group-containing organopolysiloxane (A6) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 7

Production of Methacryloxy Group-Containing Organopolysiloxane (A7)

24 g (0.1 mol) of 1,3,5,7-tetramethylcyclotetrasiloxane as the component (a1), 13 g (0.05 mol) of methyltris(dimethylsiloxy)silane and 0.1 g (0.002 mol) of tetramethlsilane as the component (a2), 119 g (0.2 mol) of vinyldimethylsiloxy-terminated polydimethylsiloxane (weight-average molecular weight: 780) represented by the average composition formula (B1-7) shown below as the component (b1), 53 g (0.3 mol) of 3-butenylmethacrylate as the component (c)

768 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

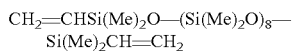

(B1-7)

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 180 g of methacryloxy group-containing organopolysiloxane (A7) represented by the general formula (50) shown below.

The obtained methacryloxy group-containing organopolysiloxane (A7) had a functional group equivalent weight of 767 g/mol, a weight-average molecular weight of 189800 calculated by GPC measurement, and a viscosity of 45000 mPa·s at 25° C.

(50)

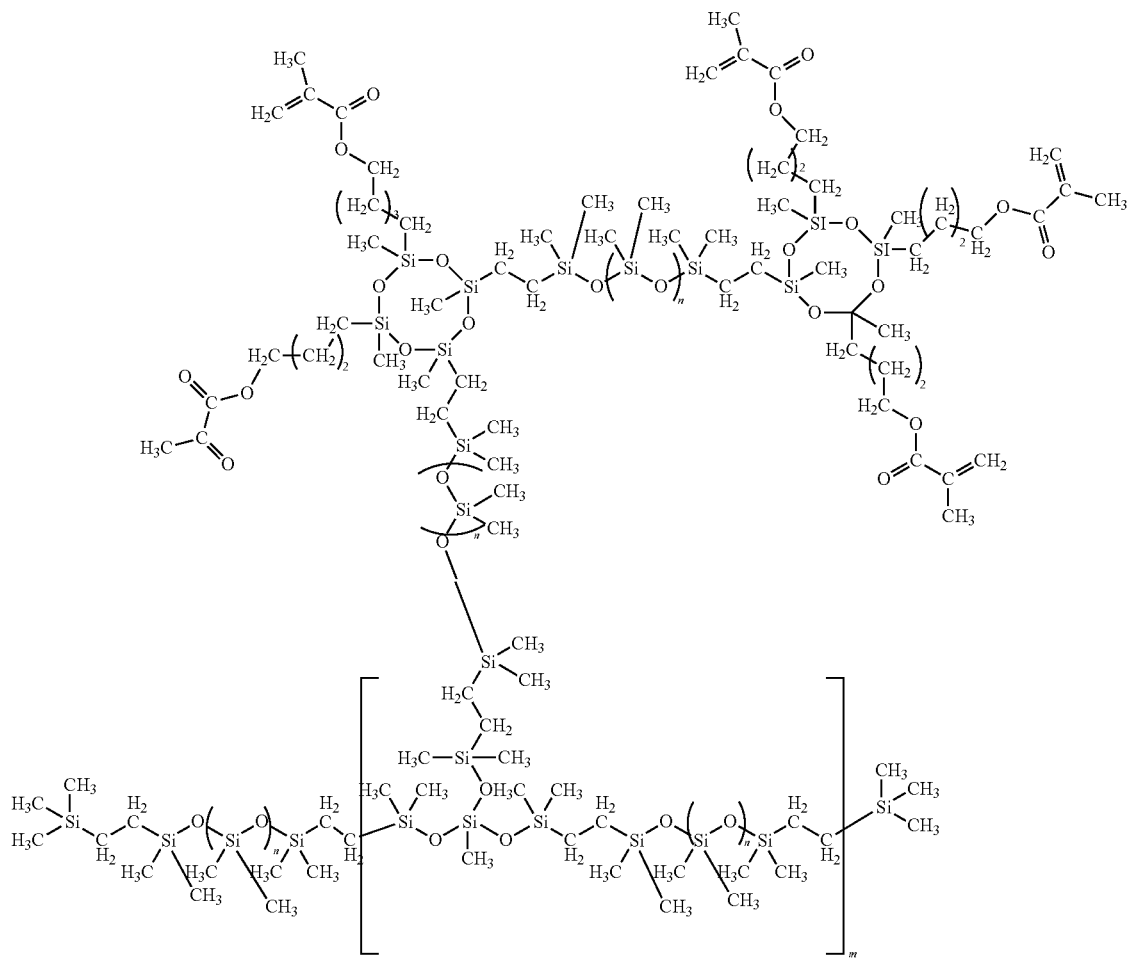

In the formula (50), m represents an integer of 50 on average, and n represents an integer of 8 on average.

As a result of Si NMR measurement, the following peaks corresponding to the constitutional units were observed:

F1: −18.2 ppm
M1: +8.8 ppm
T: −66.2 ppm
D2: −19.8 ppm
D3: −21.2 ppm

The value of a/(b+c) was 0.70.

S: No peak was observed at −32.3 ppm, and the value of d/a was 0.

<Production of Cured Product and Evaluation of Property>

100 parts by mass of the methacryloxy group-containing organopolysiloxane (A7) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 8

Production of Methacryloxy Group-Containing Organopolysiloxane (A8)

53 g (0.2 mol) of 1,3,5,7-tetramethylcyclotetrasiloxane as the component (a1), 27 g (0.1 mol) of methyltris(dimethylsiloxy)silane as the component (a2), 235 g (0.3 mol) of hydroxydimethylsiloxy-terminated polydimethylsiloxane (weight-average molecular weight: 760) represented by the average composition formula (B1-8) shown below as the component (b2), 118 g (0.9 mol) of 3-butenylmethacrylate as the component (c)

1600 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

HO—Si(Me)$_2$O—(Si(Me)$_2$O)$_8$—Si(Me)$_2$—OH  (B1-8)

Then, an isopropanol solution of chloroplatinic acid was added so that the amount of the platinum metal was 40 ppm based on the weight of organopolysiloxane which was an addition reaction product.

The start of dehydration reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 96%.

Then, the reaction system was treated with active carbon, and volatile matter was distilled off to obtain 370 g of methacryloxy group-containing organopolysiloxane (A8) represented by the general formula (51) shown below.

The obtained methacryloxy group-containing organopolysiloxane (A8) had a functional group equivalent weight of 703 g/mol, a weight-average molecular weight of 34500 calculated by GPC measurement, and a viscosity of 2500 mPa·s at 25° C.

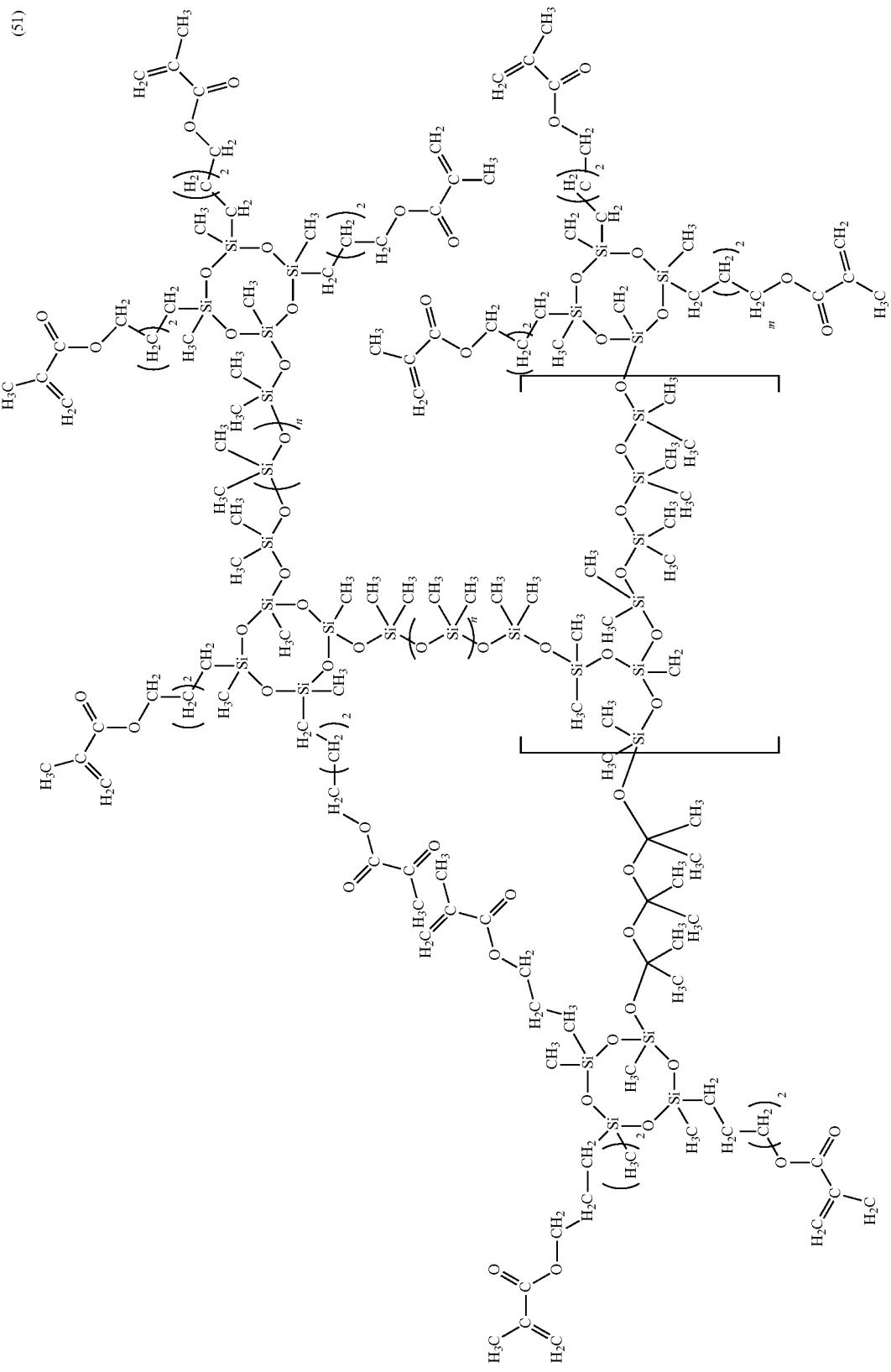
(51)

In the formula (51), m represents an integer of 10 on average, and n represents an integer of 8 on average.

As a result of Si NMR measurement, the following peaks corresponding to the constitutional units were observed:
F1: −18.2 ppm
T: −66.2 ppm
D1 and D2: −19.8 ppm
D3: −21.2 ppm
S: −32.3 ppm The value of a/(b+c) was 1.33, and the value of d/a was 0.09.

<Production of Cured Product and Evaluation of Property>

100 parts by mass of the methacryloxy group-containing organopolysiloxane (A8) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 1 below.

Example 9

Production of Methacryloxy Group-Containing Organopolysiloxane (A9)

53 g (0.2 mol) of 1,3,5,7-tetramethylcyclotetrasiloxane as the component (a1), 16 g (0.05 mol) of tetrakis(dimethylsiloxy)silane as the component (a2), 197 g (0.3 mol) of hydroxydimethylsiloxy-terminated polydimethylsiloxane (weight-average molecular weight: 760) represented by the average composition formula (B1-9) shown below as the component (b2), 118 g (0.9 mol) of 3-butenylmethacrylate as the component (c)

1500 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

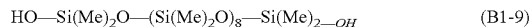
$$\text{HO—Si(Me)}_2\text{O—(Si(Me)}_2\text{O)}_8\text{—Si(Me)}_2\text{—OH} \tag{B1-9}$$

Then, an isopropanol solution of chloroplatinic acid was added so that the amount of the platinum metal was 40 ppm based on the weight of organopolysiloxane which was an addition reaction product.

The start of dehydration reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 97%.

Then, the reaction system was treated with active carbon, and volatile matter was distilled off to obtain 325 g of methacryloxy group-containing organopolysiloxane (A9) represented by the general formula (52) shown below.

The obtained methacryloxy group-containing organopolysiloxane (A9) had a functional group equivalent weight of 617 g/mol, a weight-average molecular weight of 33200 calculated by GPC measurement, and a viscosity of 3400 mPa·s at 25° C.

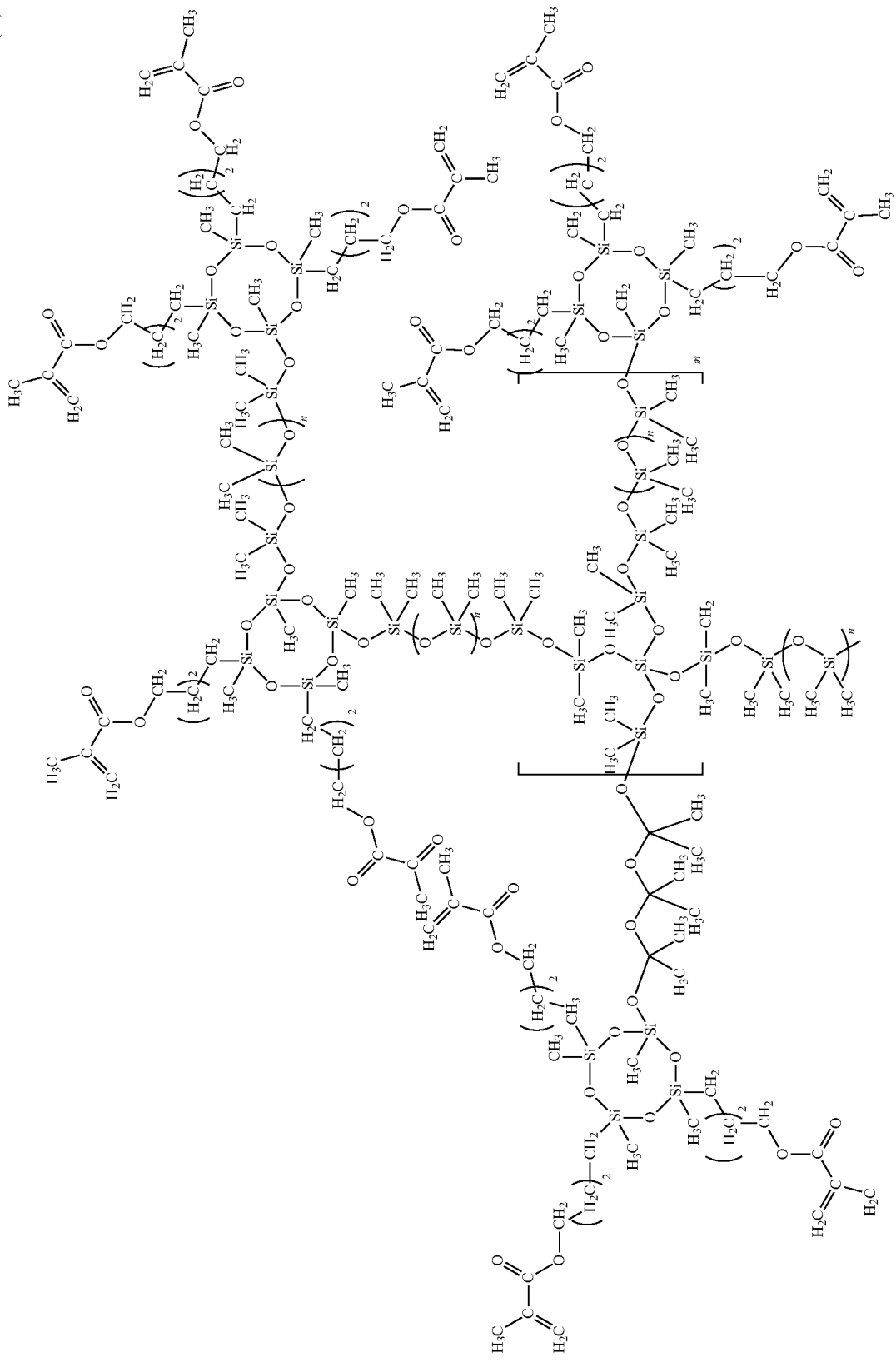

-continued
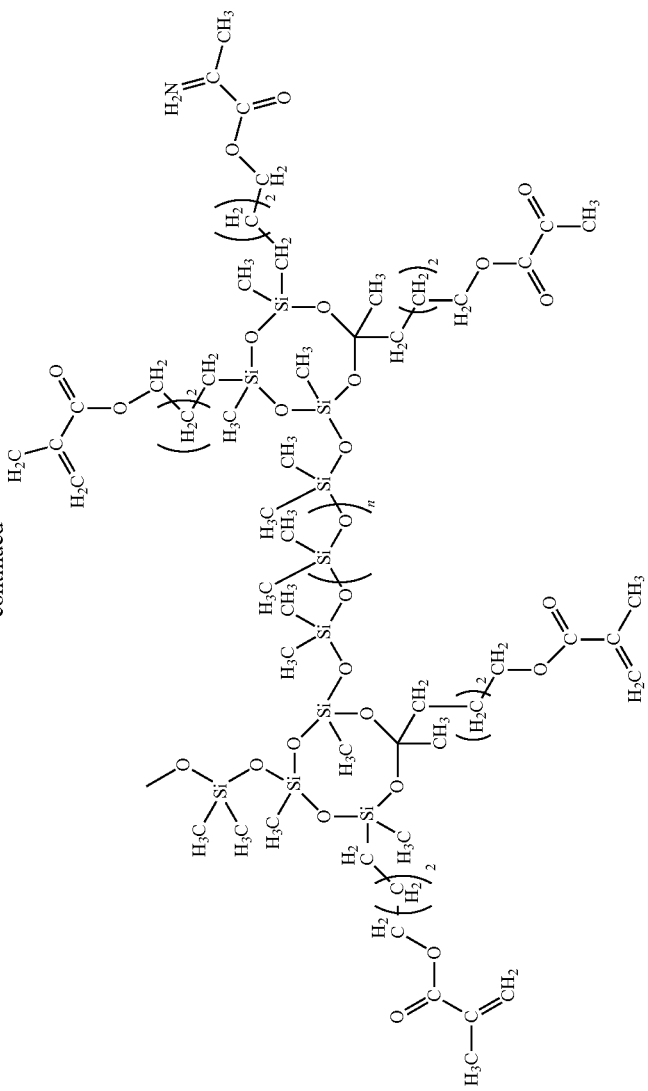

In the formula (52), m represents an integer of 5 on average, and n represents an integer of 8 on average.

As a result of Si NMR measurement, the following peaks corresponding to the constitutional units were observed:
F1: −18.2 ppm
T: −66.2 ppm
D3: −21.2 ppm
S: −32.3 ppm The value of a/(b+c) was 1.75, and the value of d/a was 0.08.

<Production of Cured Product and Evaluation of Property>

100 parts by mass of the methacryloxy group-containing organopolysiloxane (A9) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 2 below.

Example 10

Production of Methacryloxy Group-Containing Organopolysiloxane (A10)

41 g (0.2 mol) of 1,3,5,7-tetramethylcyclotetrasiloxane as the component (a1),
122 g (0.2 mol) of hydroxydimethylsiloxy-terminated polydimethylsiloxane (weight-average molecular weight: 760) represented by the average composition formula (B1-10) shown below as the component (b2),
76 g (0.6 mol) of 3-butenylmethacrylate as the component (c)
864 g of toluene, and
0.05 g of hydroquinone monomethyl ether (polymerization inhibitor)
were added to a 3.0-L three-neck flask equipped with a stirrer, a thermometer, and a reflux condenser, and the mixture was heated to 60° C. with stirring in a nitrogen gas atmosphere.

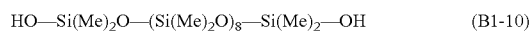

$$HO-Si(Me)_2O-(Si(Me)_2O)_8-Si(Me)_2-OH \quad (B1-10)$$

Then, an isopropanol solution of chloroplatinic acid was added so that the amount of the platinum metal was 40 ppm based on the weight of organopolysiloxane which was an addition reaction product.

The start of dehydration reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 96%.

Then, the reaction system was treated with active carbon, and volatile matter was distilled off to obtain 201 g of methacryloxy group-containing organopolysiloxane (A10) represented by the general formula (53) shown below.

The obtained methacryloxy group-containing organopolysiloxane (A10) had a functional group equivalent weight of 591 g/mol, a weight-average molecular weight of 19500 calculated by GPC measurement, and a viscosity of 4200 mPa·s at 25° C.

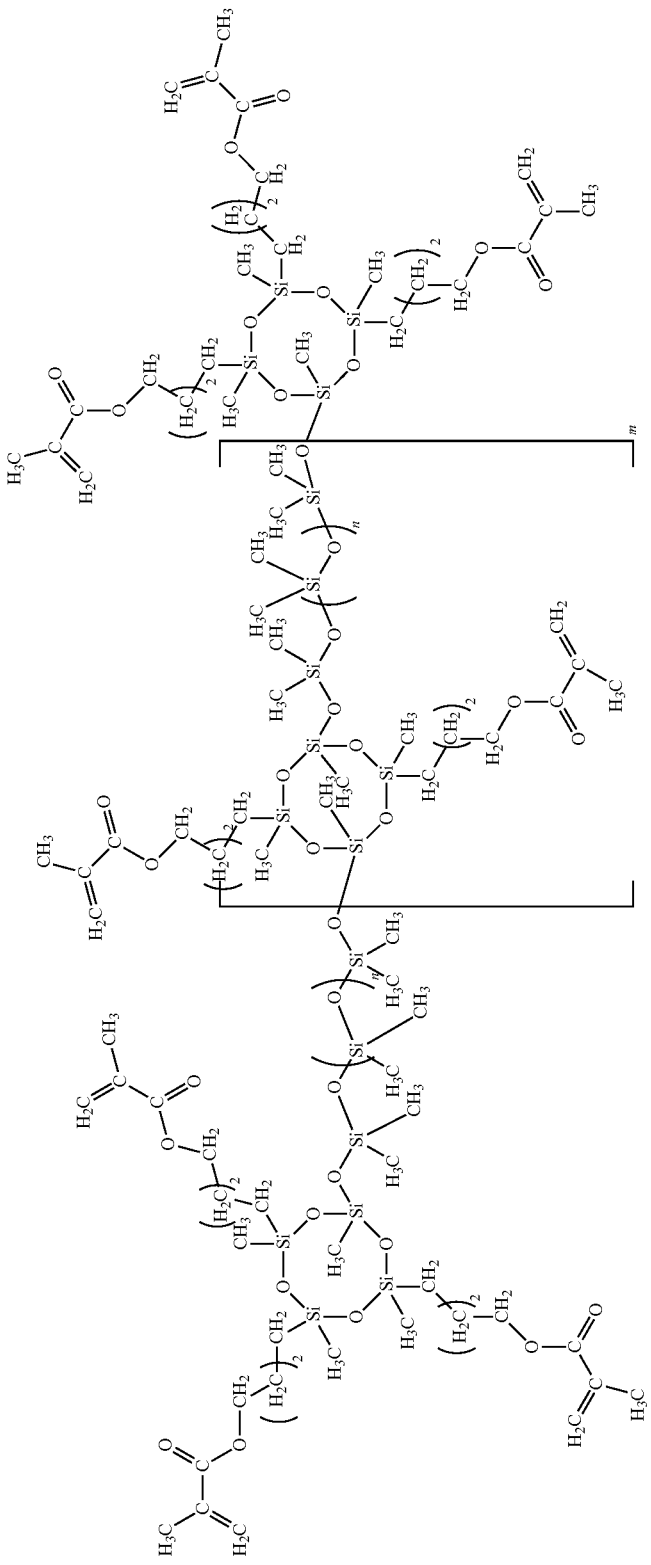
(53)

In the formula (53), m represents an integer of 15 on average, and n represents an integer of 8 on average.

As a result of Si NMR measurement, the following peaks corresponding to the constitutional units were observed:

F1: −18.2 ppm
T: −66.2 ppm
D3: −21.2 ppm
S: −32.3 ppm

The value of a/(b+c) was 1.13, and the value of d/a was 0.08.

<Production of Cured Product and Evaluation of Property>

100 parts by mass of the methacryloxy group-containing organopolysiloxane (A10) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 9 hours and further at 150° C. for 1 hour to obtain a cured product.

Results of evaluating the properties of the obtained cured product are shown in Table 2 below.

Example 11

Production of Methacryloxy Group-Containing Organopolysiloxane (A11)

68 g (0.3 mol) of 1,3,5,7-tetramethylcyclotetrasiloxane as the component (a1), 45 g (0.3 mol) of hydroxydimethylsiloxy-terminated dimethyldisiloxane (molecular weight: 166) represented by the average composition formula (B1-11) shown below as the component (b2), 119 g (0.9 mol) of 3-butenylmethacrylate as the component (c)

795 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

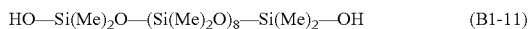

$$\text{HO—Si(Me)}_2\text{O—(Si(Me)}_2\text{O)}_8\text{—Si(Me)}_2\text{—OH} \quad (B1\text{-}11)$$

Then, an isopropanol solution of chloroplatinic acid was added so that the amount of the platinum metal was 40 ppm based on the weight of organopolysiloxane which was an addition reaction product.

The start of dehydration reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 183 g of methacryloxy group-containing organopolysiloxane (A11) represented by the general formula (54), the general formula (55) and the general formula (56) shown below.

The obtained methacryloxy group-containing organopolysiloxane (A11) had a functional group equivalent weight of 340 g/mol, a weight-average molecular weight of 17600 calculated by GPC measurement, and a viscosity of 14500 mPa·s at 25° C.

The obtained methacryloxy group-containing organopolysiloxane (A11) had a [WB]/[WA] value of 1.9. In this context, the general formula (55) corresponds to the general formula (9), and the general formula (56) corresponds to the general formula (10).

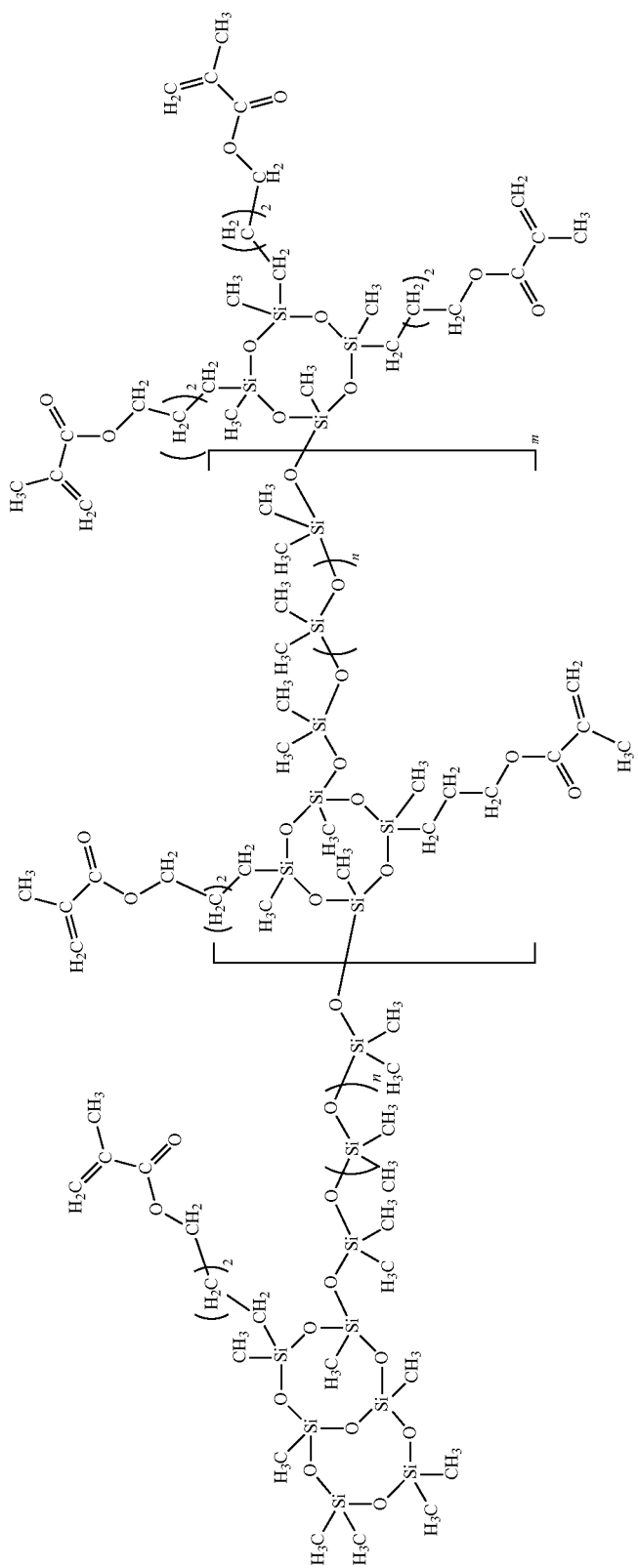

-continued
(55)
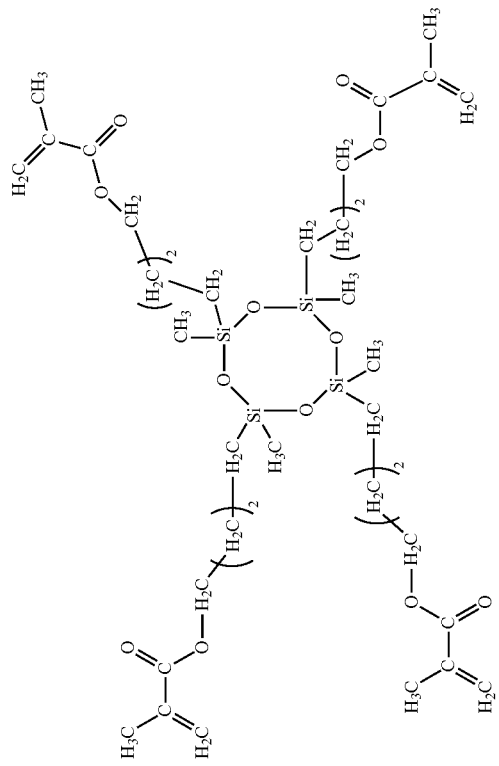
(56)
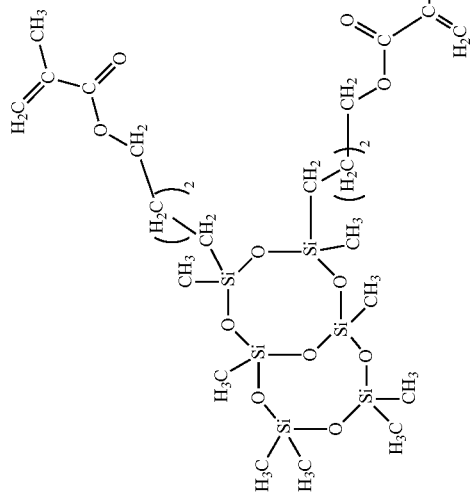

In the formula (54), m represents an integer of 25 on average, and n represents an integer of 0 on average.

As a result of Si NMR measurement, the following peaks corresponding to the constitutional units were observed:

F1: −18.2 ppm

T: −66.2 ppm

The value of a/(b+c) was 1.00.

S: No peak was observed at −32.3 ppm, and the value of d/a was 0.

<Production of Cured Product and Evaluation of Property>

100 parts by mass of the methacryloxy group-containing organopolysiloxane (A11) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 2 below.

Example 12

Production of Methacryloxy Group-Containing Organopolysiloxane (A12)

201 g (0.8 mol) of 1,3,5,7-tetramethylcyclotetrasiloxane as the component (a1), 240 g (1.4 mol) of hydroxydimethylsiloxy-terminated dimethyldisiloxane (molecular weight: 166) represented by the average composition formula (B1-12) shown below as the component (b2), 97 g (0.7 mol) of 3-butenylmethacrylate as the component (c)

2138 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

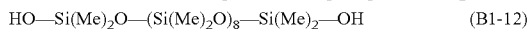

$HO-Si(Me)_2O-(Si(Me)_2O)_8-Si(Me)_2-OH$  (B1-12)

Then, an isopropanol solution of chloroplatinic acid was added so that the amount of the platinum metal was 40 ppm based on the weight of organopolysiloxane which was an addition reaction product.

The start of dehydration reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 93%.

Then, the reaction system was treated with active carbon, and volatile matter was distilled off to obtain 490 g of methacryloxy group-containing organopolysiloxane (A12) represented by the general formula (57), the general formula (58) and the general formula (59) shown below.

The obtained methacryloxy group-containing organopolysiloxane (A12) had a functional group equivalent weight of 1094 g/mol, a weight-average molecular weight of 99700 calculated by GPC measurement, and a viscosity of 25500 mPa·s at 25° C.

The obtained methacryloxy group-containing organopolysiloxane (A12) had a [WB]/[WA] value of 9.6. In this context, the general formula (58) corresponds to the general formula (9), and the general formula (59) corresponds to the general formula (10).

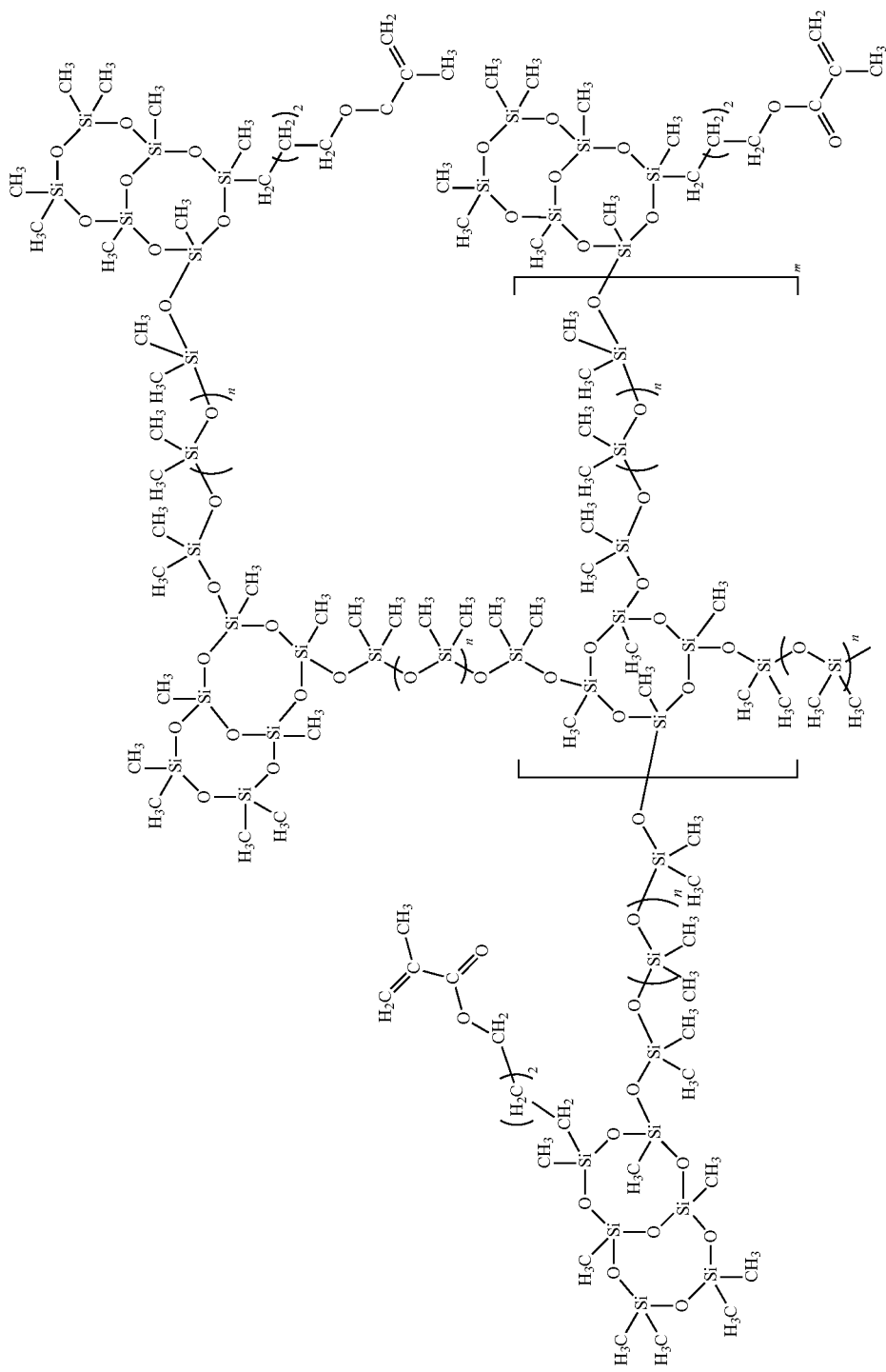

-continued
(59)
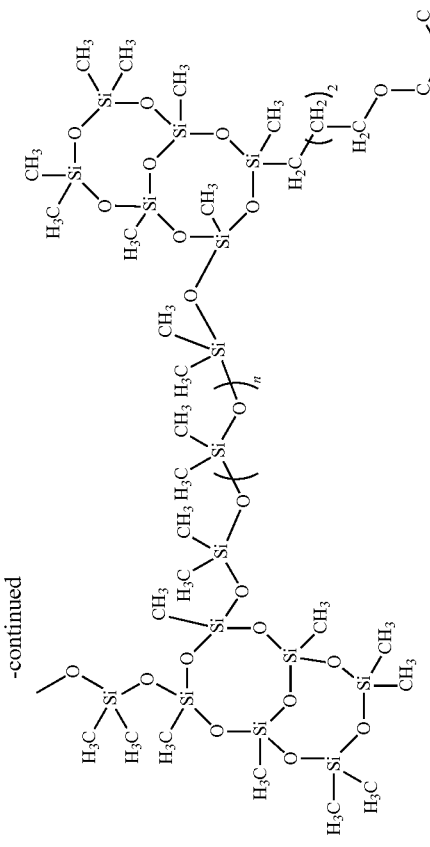
(58)
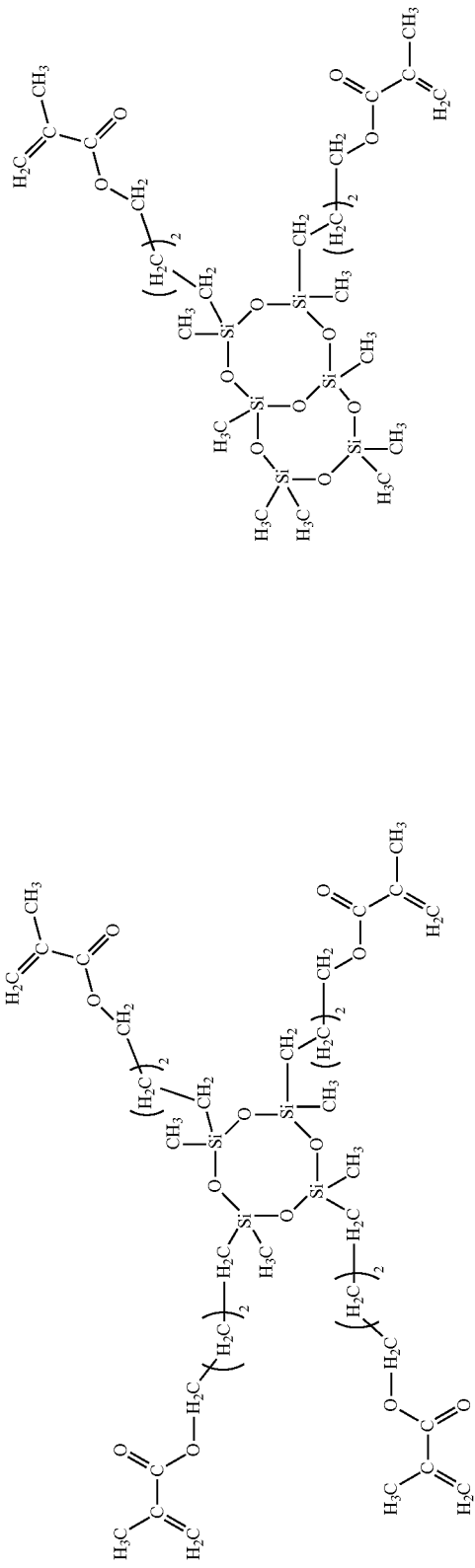

In the formula (57), m represents an integer of 30 on average, and n represents an integer of 0 on average.

As a result of Si NMR measurement, the following peaks corresponding to the constitutional units were observed:

F1: −18.2 ppm
T: −66.2 ppm

The value of a/(b+c) was 0.15.

S: No peak was observed at −32.3 ppm, and the value of d/a was 0.

<Production of Cured Product and Evaluation of Property>

100 parts by mass of the methacryloxy group-containing organopolysiloxane (A12) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 2 below.

Example 13

Production of Methacryloxy Group-Containing Organopolysiloxane (A13)

24 g (0.1 mol) of 1,3,5,7-tetramethylcyclotetrasiloxane as the component (a1), 13 g (0.05 mol) of methyltris(dimethylsiloxy)silane and 0.1 g (0.002 mol) of tetramethylsilane as the component (a2), 116 g (0.2 mol) of hydroxydimethylsiloxy-terminated polydimethylsiloxane (weight-average molecular weight: 760) represented by the average composition formula (B1-13) shown below as the component (b2), 53 g (0.3 mol) of 3-butenylmethacrylate as the component (c)

768 g of toluene, and 0.05 g of hydroquinone monomethyl ether (polymerization inhibitor)

were added to a 3.0-L three-neck flask equipped with a stirrer, a thermometer, and a reflux condenser, and the mixture was heated to 60° C. with stirring in a nitrogen gas atmosphere.

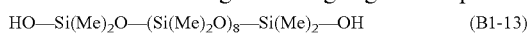
(B1-13)

Then, an isopropanol solution of chloroplatinic acid was added so that the amount of the platinum metal was 40 ppm based on the weight of organopolysiloxane which was an addition reaction product.

The start of dehydration reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 97%.

Then, the reaction system was treated with active carbon, and volatile matter was distilled off to obtain 170 g of methacryloxy group-containing organopolysiloxane (A13) represented by the general formula (60) shown below.

The obtained methacryloxy group-containing organopolysiloxane (A13) had a functional group equivalent weight of 756 g/mol, a weight-average molecular weight of 182100 calculated by GPC measurement, and a viscosity of 42300 mPa·s at 25° C.

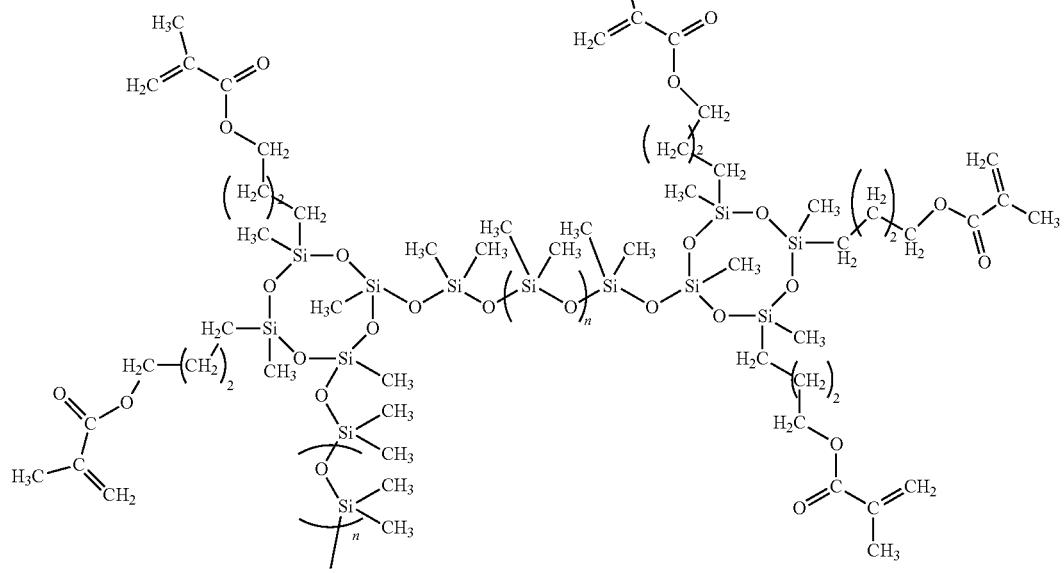
(60)

-continued

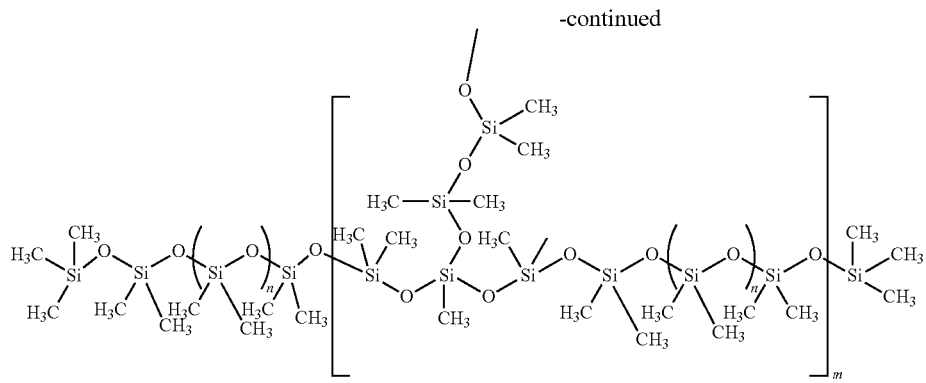

In the formula (60), m represents an integer of 50 on average, and n represents an integer of 8 on average.

As a result of Si NMR measurement, the following peaks corresponding to the constitutional units were observed:
F1: −18.2 ppm
T: −66.2 ppm
D3: −21.2 ppm
S: −32.3 ppm The value of a/(b+c) was 1.25, and the value of d/a was 0.10.

<Production of Cured Product and Evaluation of Property>

100 parts by mass of the methacryloxy group-containing organopolysiloxane (A13) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 2 below.

Example 14

Production of Methacryloxy Group-Containing Organopolysiloxane (A14)

96 g (0.4 mol) of 1,3,5,7-tetramethylcyclotetrasiloxane as the component (a1),
107 g (0.8 mol) of 1,1,3,3-tetramethyldisiloxane as the component (a2),
269 g (1.4 mol) of vinyldimethylsiloxy-terminated dimethyldisiloxane (molecular weight: 186) represented by the average composition formula (B1-14) shown below as the component (b1),
97 g (0.7 mol) of 3-butenylmethacrylate as the component (c)
2138 g of toluene, and
0.05 g of hydroquinone monomethyl ether (polymerization inhibitor)
were added to a 3.0-L three-neck flask equipped with a stirrer, a thermometer, and a reflux condenser, and the mixture was heated to 60° C. with stirring in a nitrogen gas atmosphere.

$$CH_2=CHSi(Me)_2O—(Si(Me)_2O)_8—Si(Me)_2CH=CH_2 \quad (B1\text{-}14)$$

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept within a range of 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 520 g of methacryloxy group-containing organopolysiloxane (A14) represented by the general formula (61) and the general formula (62) shown below.

The obtained methacryloxy group-containing organopolysiloxane (A14) had a functional group equivalent weight of 1300 g/mol, a weight-average molecular weight of 11000 calculated by GPC measurement, and a viscosity of 600 mPa·s at 25° C.

The methacryloxy group-containing organopolysiloxane (A14) was obtained using both the starting materials (a1) and (a2) as hydrogen polysiloxane components each having at least one SiH group in one molecule. This reduced a crosslinked structure in the obtained methacryloxy group-containing organopolysiloxane (A14) and thus reduced the viscosity.

(61)
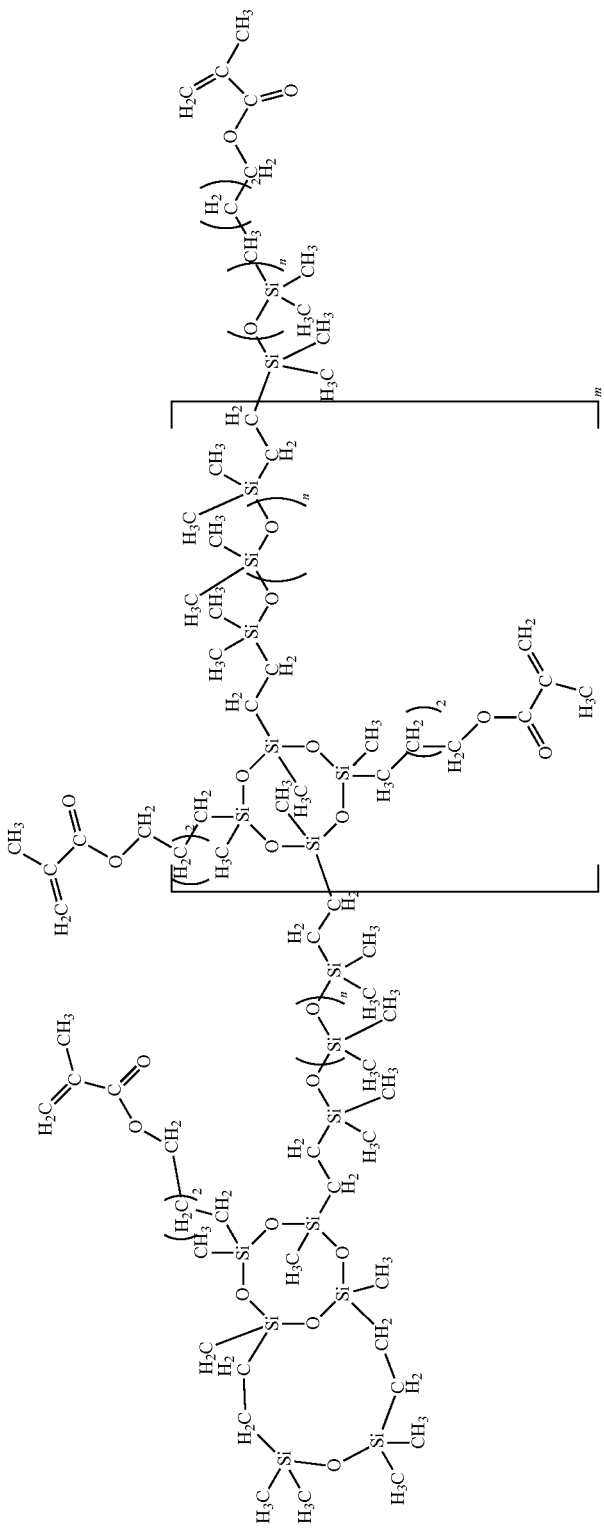
(62)
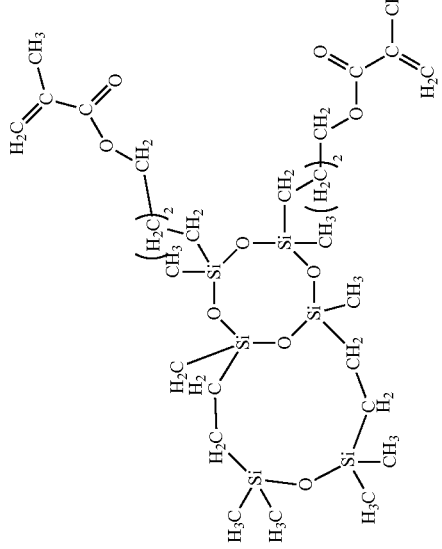

In the formula (61), m represents an integer of 30 on average, n represents an integer of 0 on average, and r represents an integer of 0 on average.

As a result of Si NMR measurement, the following peaks corresponding to the constitutional units were observed:
F1: −18.2 ppm
M1: +8.8 ppm
D2: −19.8 ppm
F2: +7.0 ppm
The value of a/(b+c) was 0.16.
S: No peak was observed at −32.3 ppm, and the value of d/a was 0.

<Production of Cured Product and Evaluation of Property>

100 parts by mass of the methacryloxy group-containing organopolysiloxane (A14) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 2 below.

Example 15

Production of Methacryloxy Group-Containing Organopolysiloxane (A2)

For reaction of the first stage,
53 g (0.2 mol) of 1,3,5,7-tetramethylcyclotetrasiloxane as the component (a1),
27 g (0.1 mol) of methyltris(dimethylsiloxy)silane as the component (a2),
40 g (0.3 mol) of 3-butenylmethacrylate as the component (c)
1600 g of toluene, and
0.05 g of hydroquinone monomethyl ether (polymerization inhibitor)
were added to a 3.0-L three-neck flask equipped with a stirrer, a thermometer, and a reflux condenser, and the mixture was heated to 60° C. with stirring in a nitrogen gas atmosphere.

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept at 55 to 65° C. by heat retention or water or air cooling.

For reaction of the second stage, 242 g (0.3 mol) of the vinyldimethylsiloxy-terminated polydimethylsiloxane (weight-average molecular weight: 780) represented by the average composition formula (B1-1) was added as the component (b1) to the reaction solution of the first stage. This reaction system was stirred for 72 hours while its temperature was kept at 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 360 g of methacryloxy group-containing organopolysiloxane (A2) represented by the general formula (41) shown above.

The obtained methacryloxy group-containing organopolysiloxane (A2) had a functional group equivalent weight of 714 g/mol, a weight-average molecular weight of 382000 calculated by GPC measurement, and a viscosity of 2600 mPa·s at 25° C.

As a result of Si NMR measurement, the following peaks corresponding to the constitutional units were observed:
F1: −18.2 ppm
M1: +8.8 ppm
T: −66.2 ppm
D2: −19.8 ppm
D3: −21.2 ppm
The value of a/(b+c) was 0.78.
S: No peak was observed at −32.3 ppm, and the value of d/a was 0.

<Production of Cured Product and Evaluation of Property>

100 parts by mass of the methacryloxy group-containing organopolysiloxane (A2) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 2 below.

Example 16

Production of Methacryloxy Group-Containing Organopolysiloxane (A2)

The methacryloxy group-containing organopolysiloxane (A2) was obtained in the same way as in Example 2.

<Production of Cured Product and Evaluation of Property>

100 parts by mass of the methacryloxy group-containing organopolysiloxane (A2) were mixed with 3 parts by mass of 1-hydroxy-cyclohexyl-phenyl ketone (manufactured by BASF Japan Ltd., trade name: IRGACURE 184) and 3 parts by mass of 2-methyl-1-[4-methylthio-phenyl]-2-morpholinopropan-1-one (manufactured by BASF Japan Ltd., trade name: IRGACURE 907), and the mixture was stirred until totally uniform, and then degassed to obtain a curable composition.

A spacer made of silicon (50 mm long×50 mm wide×3 mm high) was loaded on a glass plate (50 mm long×50 mm wide×5 mm thick) and used as a mold, and the curable composition was poured within the spacer and sandwiched between the glass plate and another glass plate.

Then, the composition was exposed to light through the glass plate with a cumulative light quantity of 2000 mJ/cm$^2$ using an ultraviolet irradiation apparatus (manufactured by Sen Engineering Co., Ltd.) equipped with a high-pressure mercury-vapor lamp.

The composition was cured in an environment involving a temperature of 23° C. and a humidity of 60% RH.

Then, the mold was released to obtain a cured product.

Results of evaluating the properties of the obtained cured product are shown in Table 2 below.

Example 17

Production of Methacryloxy Group-Containing Organopolysiloxane (A2)

The methacryloxy group-containing organopolysiloxane (A2) was obtained in the same way as in Example 2.

<Production of Cured Product and Evaluation of Property>

100 parts by mass of the methacryloxy group-containing organopolysiloxane (A2) were mixed with 3 parts by mass of 3-methacryloxypropylmethyldimethoxysilane (KBM-502, manufactured by Shin-Etsu Chemical Co., Ltd.) and 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 2 below.

Comparative Example 1

Production of Methacryloxy Group-Containing Organopolysiloxane (A15)

134 g (1.0 mol) of 1,1,3,3-tetramethyldisiloxane,
420 g (3.0 mol) of 3-butenylmethacrylate,
1600 g of toluene, and
0.05 g of hydroquinone monomethyl ether (polymerization inhibitor)
were added to a 3.0-L three-neck flask equipped with a stirrer, a thermometer, and a reflux condenser, and the mixture was heated to 60° C. with stirring in a nitrogen gas atmosphere.

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept at 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 405 g of methacryloxy group-containing organopolysiloxane (A15) represented by the general formula (63) shown below.

The obtained methacryloxy group-containing organopolysiloxane (A15) had a functional group equivalent weight of 415 g/mol, a weight-average molecular weight of 400 calculated by GPC measurement, and a viscosity of 150 mPa·s at 25° C.

(63)

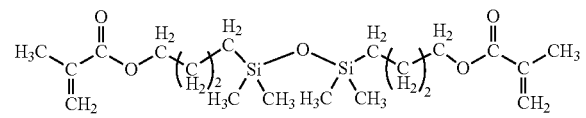

<Production of Cured Product and Evaluation of Property>

100 parts by mass of the methacryloxy group-containing organopolysiloxane (A15) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition.

This curable composition was poured into a mold made of SUS316 and cured through reaction at 100° C. for 4 hours and further at 150° C. for 1 hour to obtain a cured product.

Results of evaluating the properties of the obtained cured product are shown in Table 3 below.

Comparative Example 2

Methacryloxy Group-Containing Organopolysiloxane (A16)

X22-164C manufactured by Shin-Etsu Chemical Co., Ltd. was used as a methacryloxy group-containing organopolysiloxane (A16) represented by the general formula (64) shown below.

The methacryloxy group-containing organopolysiloxane (A16) had a functional group equivalent weight of 2300 g/mol, a weight-average molecular weight of 4500 calculated by GPC measurement, and a viscosity of 3600 mPa·s at 25° C.

(64)

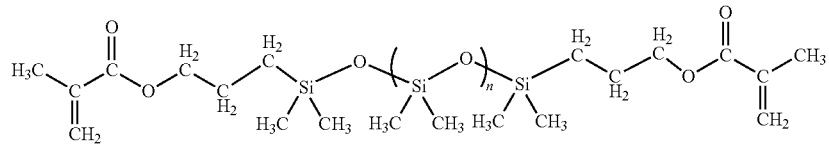

<Production of Cured Product and Evaluation of Property>

100 parts by mass of the methacryloxy group-containing organopolysiloxane (A16) were mixed with 2.5 parts by mass of tert-amylperoxy-2-ethylhexanoate (manufactured by Kayaku Akzo Corp., trade name: Trigonox 121-50E, 50% by mass of solution) in a nitrogen atmosphere, and the mixture was stirred until totally uniform, and then degassed to obtain a curable composition. This curable composition was poured into a mold made of SUS316 and cured through reaction at 100° C. for 4 hours and further at 150° C. for 1 hour to obtain a cured product.

Results of evaluating the properties of the obtained cured product are shown in Table 3 below.

Comparative Example 3

Production of Epoxy Group-Containing Organopolysiloxane (A17)

53 g (0.2 mol) of 1,3,5,7-tetramethylcyclotetrasiloxane as the component (a1),
27 g (0.1 mol) of methyltris(dimethylsiloxy)silane as the component (a2),
242 g (0.3 mol) of vinyldimethylsiloxy-terminated polydimethylsiloxane (weight-average molecular weight: 780) represented by the average composition formula (B1-1) shown above as the component (b1),
104 g (0.9 mol) of vinylcyclohexeneoxide as the component (c), and
1300 g of toluene
were added to a 3.0-L three-neck flask equipped with a stirrer, a thermometer, and a reflux condenser, and the mixture was heated to 60° C. with stirring in a nitrogen gas atmosphere.

Then, an isopropanol solution of chloroplatinic acid was added so that the amount of the platinum metal was 20 ppm based on the weight of organopolysiloxane which was an addition reaction product.

The start of hydrosilylation reaction was confirmed, and this reaction system was then stirred for 72 hours while its temperature was kept at 55 to 65° C. by heat retention or water or air cooling.

As a result of analyzing the contents in the flask, the rate of reaction of SiH groups was 99%.

Then, the reaction system was treated with active carbon, and volatile matter was distilled off to obtain 310 g of epoxy group-containing organopolysiloxane (A17) represented by the general formula (65) shown below.

The epoxy group-containing organopolysiloxane (A17) was free from an unsaturated bond-containing group.

The obtained epoxy group-containing organopolysiloxane (A17) had a weight-average molecular weight of 30500 calculated by GPC measurement, and a viscosity of 5600 mPa·s at 25° C.

(65)
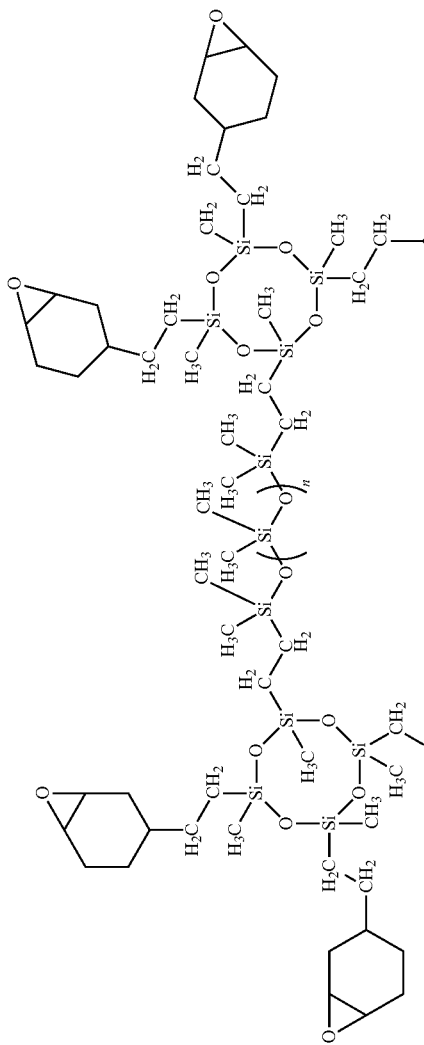
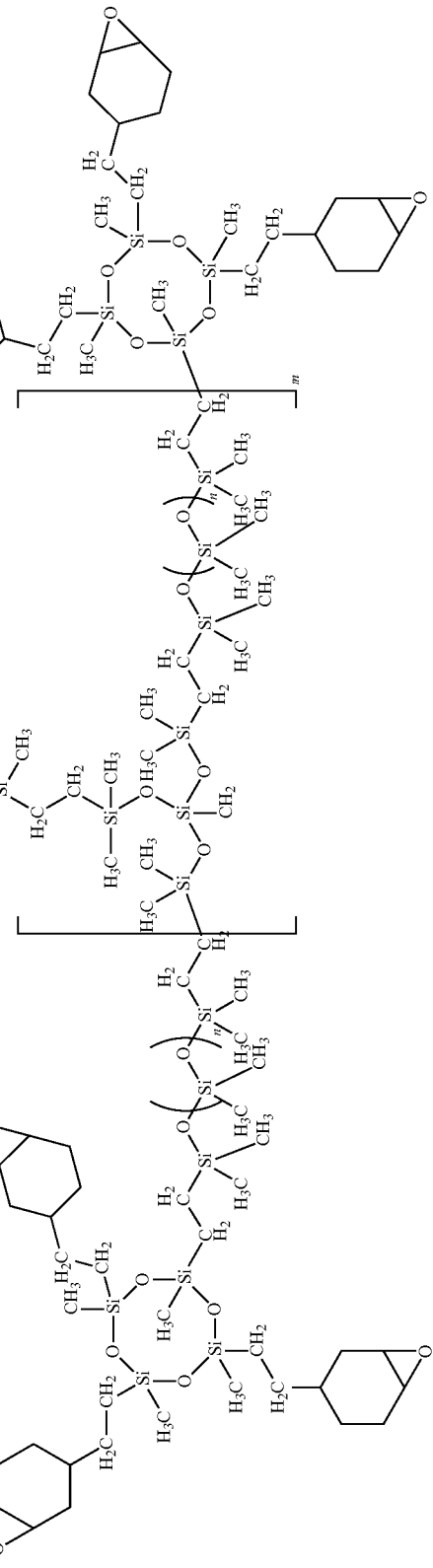

In the formula (65), m represents an integer of 10 on average, and n represents an integer of 8 on average.

<Production of Cured Product and Evaluation of Property>

100 parts by mass of the epoxy group-containing organopolysiloxane (A17) were mixed with 60.5 parts by mass of methylhexahydrophthalic anhydride and 1 part by mass of diazabicycloundecene octoate, and the mixture was stirred until totally uniform, and then degassed to obtain a curable composition.

This curable composition was poured into a mold and cured through reaction at 120° C. for 1 hour and further at 150° C. for 2 hours to obtain a cured product.

Results of evaluating the properties of the obtained cured product are shown in Table 3 below.

Comparative Example 4

Curable Resin Composition (A18)

KER-2500 manufactured by Shin-Etsu Chemical Co., Ltd., which is commercially available as a curable resin for optical semiconductor sealing materials, was used as the curable resin composition (A18).

<Production of Cured Product and Evaluation of Property>

100 parts by mass of each commercially available KER-2500A and KER-2500B were mixed and stirred until totally uniform, and then degassed to obtain a curable composition.

This curable composition was poured into a mold made of SUS316 and cured through reaction at 100° C. for 1 hour and further at 150° C. for 5 hours to obtain a cured product.

Results of evaluating the properties of the obtained cured product are shown in Table 3 below.

Comparative Example 5

Curable Resin Composition (A19)

ASP-1010 manufactured by Shin-Etsu Chemical Co., Ltd., which is commercially available as a curable resin for optical semiconductor sealing materials, was used as the curable resin composition (A19).

<Production of Cured Product and Evaluation of Property>

Commercially available ASP-1010A (trade name, manufactured by Shin-Etsu Chemical Co., Ltd.) and ASP-1010B (trade name, manufactured by Shin-Etsu Chemical Co., Ltd.) (both, 100 parts by mass) were mixed and stirred until totally uniform, and then degassed to obtain a curable composition.

This curable composition was poured into a mold made of SUS316 and cured through reaction at 100° C. for 1 hour and further at 150° C. for 5 hours to obtain a cured product.

Results of evaluating the properties of the obtained cured product are shown in Table 3 below.

Comparative Example 6

Curable Resin Composition (A20)

FX-001 manufactured by Kaneka Corp., which is commercially available as a curable resin for optical semiconductor sealing materials, was used as the curable resin composition (A20).

<Production of Cured Product and Evaluation of Property>

Commercially available FX-001A (trade name, manufactured by Kaneka Corp.; 40 parts by mass) and FX-001B (trade name, manufactured by Kaneka Corp.; 60 parts by mass) were mixed and stirred until totally uniform, and then degassed to obtain a curable composition.

This curable composition was poured into a mold made of SUS316 and cured through reaction at 100° C. for 1 hour and further at 180° C. for 0.5 hours to obtain a cured product.

Results of evaluating the properties of the obtained cured product are shown in Table 3 below.

TABLE 1

|  | Example 1 | Example 2 | Example 3 | Example 4 | Example 5 | Example 6 | Example 7 | Example 8 |
|---|---|---|---|---|---|---|---|---|
| Organosiloxane (A1) having unsaturated bond-containing group | 100 parts by mass | | | | | | | |
| Methacryloxy group-containing organosiloxane (A2) | | 100 parts by mass | | | | | | |
| Methacryloxy group-containing organosiloxane (A3) | | | 100 parts by mass | | | | | |
| Methacryloxy group-containing organosiloxane (A4) | | | | 100 parts by mass | | | | |
| Methacryloxy group-containing organosiloxane (A5) | | | | | 100 parts by mass | | | |
| Methacryloxy group-containing organosiloxane (A6) | | | | | | 100 parts by mass | | |
| Methacryloxy group-containing organosiloxane (A7) | | | | | | | 100 parts by mass | |
| Methacryloxy group-containing organosiloxane (A8) | | | | | | | | 100 parts by mass |
| Methacryloxy group-containing organosiloxane (A9) | | | | | | | | |
| Methacryloxy group-containing organosiloxane (A10) | | | | | | | | |
| Methacryloxy group-containing organosiloxane (A11) | | | | | | | | |
| Methacryloxy group-containing organosiloxane (A12) | | | | | | | | |
| Methacryloxy group-containing organosiloxane (A13) | | | | | | | | |
| Methacryloxy group-containing organosiloxane (A14) | | | | | | | | |

TABLE 1-continued

|  | Example 1 | Example 2 | Example 3 | Example 4 | Example 5 | Example 6 | Example 7 | Example 8 |
|---|---|---|---|---|---|---|---|---|
| Methacryloxy group-containing organosiloxane (A15) | | | | | | | | |
| Methacryloxy group-containing organosiloxane (A16) | | | | | | | | |
| Epoxy group-containing organosiloxane (A17) | | | | | | | | |
| Curable resin composition (A18) | | | | | | | | |
| Curable resin composition (A19) | | | | | | | | |
| Curable resin composition (A20) | | | | | | | | |
| 3-Methacryloxypropylmethyl-dimethoxysilane | | | | | | | | |
| Methylhexahydrophthalic anhydride | | | | | | | | |
| Thermal radical generator | 2.5 parts by mass | 2.5 parts by mass | 2.5 parts by mass | 2.5 parts by mass | 2.5 parts by mass | 2.5 parts by mass | 2.5 parts by mass | 2.5 parts by mass |
| Photo-radical generator | | | | | | | | |
| Diazabicycloundecene octoate | | | | | | | | |
| Rate of reaction of SiH | excellent | excellent | good | excellent | excellent | excellent | excellent | good |
| Thermal yellowing resistance | good | excellent | excellent | excellent | excellent | excellent | excellent | good |
| Light resistance | good | excellent | excellent | excellent | excellent | excellent | excellent | good |
| Heat and cold shock resistance | good | excellent | good | good | good | excellent | excellent | good |
| Hardness | good | excellent | excellent | excellent | excellent | good | good | good |
| Adhesion | good | good | good | good | good | good | good | good |
| Gas barrier | excellent | good | good | good | excellent | excellent | good | good |

TABLE 2

|  | Example 9 | Example 10 | Example 11 | Example 12 | Example 13 | Example 14 | Example 15 | Example 16 | Example 17 |
|---|---|---|---|---|---|---|---|---|---|
| Organosiloxane (A1) having unsaturated bond-containing group | | | | | | | | | |
| Methacryloxy group-containing organosiloxane (A2) | | | | | | | 100 parts by mass | 100 parts by mass | 100 parts by mass |
| Methacryloxy group-containing organosiloxane (A3) | | | | | | | | | |
| Methacryloxy group-containing organosiloxane (A4) | | | | | | | | | |
| Methacryloxy group-containing organosiloxane (A5) | | | | | | | | | |
| Methacryloxy group-containing organosiloxane (A6) | | | | | | | | | |
| Methacryloxy group-containing organosiloxane (A7) | | | | | | | | | |
| Methacryloxy group-containing organosiloxane (A8) | | | | | | | | | |
| Methacryloxy group-containing organosiloxane (A9) | 100 parts by mass | | | | | | | | |
| Methacryloxy group-containing organosiloxane (A10) | | 100 parts by mass | | | | | | | |
| Methacryloxy group-containing organosiloxane (A11) | | | 100 parts by mass | | | | | | |
| Methacryloxy group-containing organosiloxane (A12) | | | | 100 parts by mass | | | | | |
| Methacryloxy group-containing organosiloxane (A13) | | | | | 100 parts by mass | | | | |
| Methacryloxy group-containing organosiloxane (A14) | | | | | | 100 parts by mass | | | |
| Methacryloxy group-containing organosiloxane (A15) | | | | | | | | | |
| Methacryloxy group-containing organosiloxane (A16) | | | | | | | | | |
| Epoxy group-containing organosiloxane (A17) | | | | | | | | | |
| Curable resin composition (A18) | | | | | | | | | |
| Curable resin composition (A19) | | | | | | | | | |
| Curable resin composition (A20) | | | | | | | | | |
| 3-Methacryloxypropylmethyl-dimethoxysilane | | | | | | | | | 3 parts by mass |
| Methylhexahydrophthalic anhydride | | | | | | | | | |
| Thermal radical generator | 2.5 parts by mass | 2.5 parts by mass | 2.5 parts by mass | 2.5 parts by mass | 2.5 parts by mass | 2.5 parts by mass | 2.5 parts by mass | | 2.5 parts by mass |

TABLE 2-continued

| | Example 9 | Example 10 | Example 11 | Example 12 | Example 13 | Example 14 | Example 15 | Example 16 | Example 17 |
|---|---|---|---|---|---|---|---|---|---|
| Photo-radical generator | | | | | | | | | 2.5 parts by mass |
| Diazabicycloundecene octoate | | | | | | | | | |
| Rate of reaction of SiH | good | good | excellent | excellent | good | excellent | excellent | excellent | excellent |
| Thermal yellowing resistance | excellent | excellent | excellent | excellent | excellent | excellent | excellent | excellent | good |
| Light resistance | excellent | excellent | excellent | excellent | excellent | excellent | excellent | excellent | excellent |
| Heat and cold shock resistance | excellent | good | good | good | excellent | excellent | excellent | excellent | excellent |
| Hardness | excellent | excellent | excellent | excellent | good | good | excellent | excellent | excellent |
| Adhesion | good | good | good | good | good | good | good | good | excellent |
| Gas barrier | good | good | excellent | excellent | good | excellent | good | good | good |

TABLE 3

| | Comparative Example 1 | Comparative Example 2 | Comparative Example 3 | Comparative Example 4 | Comparative Example 5 | Comparative Example 6 |
|---|---|---|---|---|---|---|
| Organosiloxane (A1) having unsaturated bond-containing group | | | | | | |
| Methacryloxy group-containing organosiloxane (A2) | | | | | | |
| Methacryloxy group-containing organosiloxane (A3) | | | | | | |
| Methacryloxy group-containing organosiloxane (A4) | | | | | | |
| Methacryloxy group-containing organosiloxane (A5) | | | | | | |
| Methacryloxy group-containing organosiloxane (A6) | | | | | | |
| Methacryloxy group-containing organosiloxane (A7) | | | | | | |
| Methacryloxy group-containing organosiloxane (A8) | | | | | | |
| Methacryloxy group-containing organosiloxane (A9) | | | | | | |
| Methacryloxy group-containing organosiloxane (A10) | | | | | | |
| Methacryloxy group-containing organosiloxane (A11) | | | | | | |
| Methacryloxy group-containing organosiloxane (A12) | | | | | | |
| Methacryloxy group-containing organosiloxane (A13) | | | | | | |
| Methacryloxy group-containing organosiloxane (A14) | | | | | | |
| Methacryloxy group-containing organosiloxane (A15) | 100 parts by mass | | | | | |
| Methacryloxy group-containing organosiloxane (A16) | | 100 parts by mass | | | | |
| Epoxy group-containing organosiloxane (A17) | | | 100 parts by mass | | | |
| Curable resin composition (A18) | | | | 100 parts by mass | | |
| Curable resin composition (A19) | | | | | 100 parts by mass | |
| Curable resin composition (A20) | | | | | | 100 parts by mass |
| 3-Methacryloxypropylmethyl-dimethoxysilane | | | | | | |
| Methylhexahydrophthalic anhydride | | | 60.5 parts by mass | | | |
| Thermal radical generator | 2.5 parts by mass | 2.5 parts by mass | | 2.5 parts by mass | 2.5 parts by mass | 2.5 parts by mass |
| Photo-radical generator | | | | | | |
| Diazabicycloundecene octoate | | | 1 part by mass | | | |
| Rate of reaction of SiH | excellent | — | excellent | — | — | — |
| Thermal yellowing resistance | excellent | excellent | poor | excellent | good | good |
| Light resistance | excellent | excellent | poor | excellent | poor | good |
| Heat and cold shock resistance | poor | excellent | excellent | excellent | excellent | poor |
| Hardness | excellent | poor | excellent | poor | good | good |
| Adhesion | good | good | excellent | good | good | good |
| Gas barrier | good | poor | excellent | poor | poor | excellent |

The organopolysiloxane of the present embodiment has, in its molecular structure, constitutional units F1, M1, and T in any combination of
(i) F1 and M1,
(ii) F1 and T, and
(iii) F1, M1, and T,
wherein the constitutional units F1, M1, and T are represented by the general formulas (1), (2), and (3), respectively.

The obtained organopolysiloxane having the constitutional units F1, M1, and T was excellent in thermal yellowing resistance and light resistance.

Also, the organopolysiloxane locally having, in its molecular structure, a cross-linked structure-forming site composed of the constitutional unit F1 and a stress-relieving site composed of siloxane containing the constitutional unit M1 or T had all hardness, heat and cold shock resistance, and gas barrier.

Examples 1 to 17 yielded organopolysiloxane capable of forming a transparent cured product that fully satisfied all of thermal yellowing resistance, light resistance, heat and cold shock resistance, hardness, adhesion, and gas barrier, at a level required particularly for use in optical semiconductors, and a curable resin composition containing the organopolysiloxane.

Comparative Examples 1 to 6 lacked the constitution of the present embodiment and thus failed to offer a certain property among thermal yellowing resistance, light resistance, heat and cold shock resistance, hardness, adhesion, and gas barrier or a practically sufficient property from the viewpoint of a balance among these properties.

The present application is based on International Patent Application No. PCT/JP2011/058115 filed with the Japan Patent Office on Mar. 30, 2011, and the contents of which are incorporated herein by reference.

INDUSTRIAL APPLICABILITY

The organopolysiloxane of the present invention and the curable resin composition containing the organopolysiloxane have industrial applicability as die bonding materials for optical semiconductors, coating materials, curable resin compositions for nanoimprint, and materials for the field of inks.

The invention claimed is:
1. An organopolysiloxane represented by any formula selected from the group consisting of formulae (14) through (25) and (28) through (31):

(14)
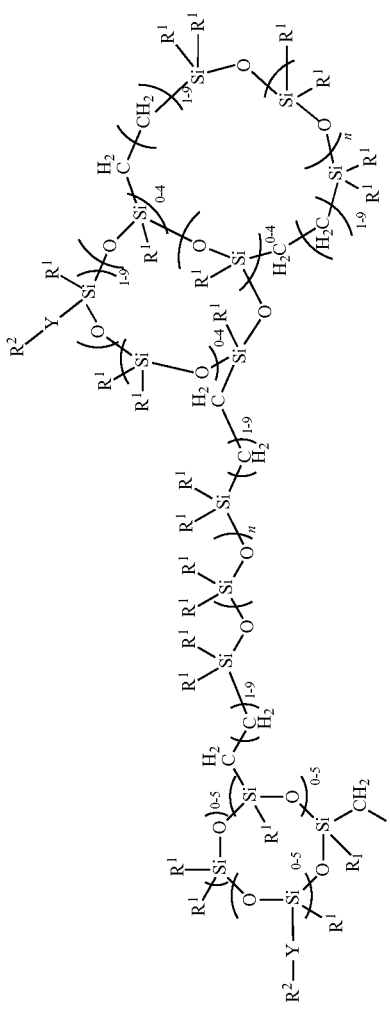
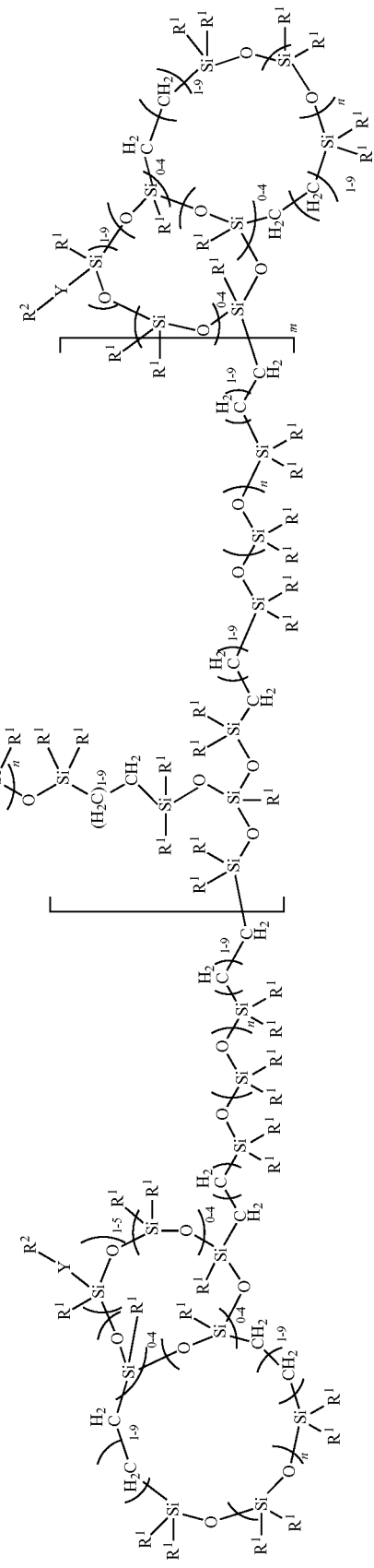

-continued
(15)
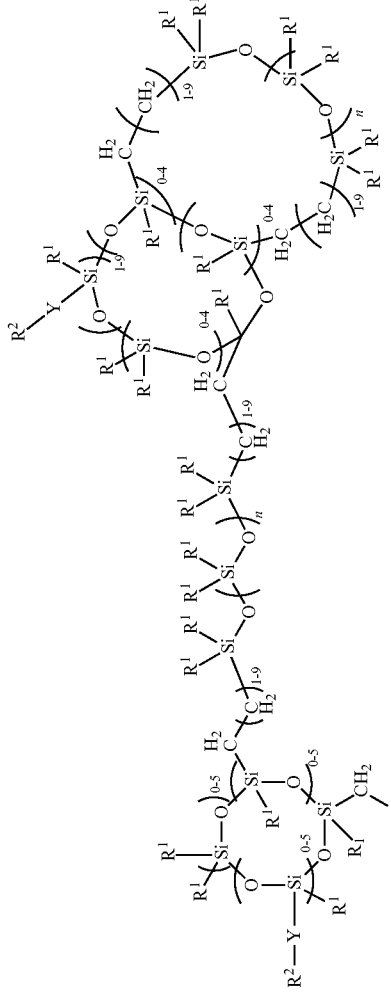
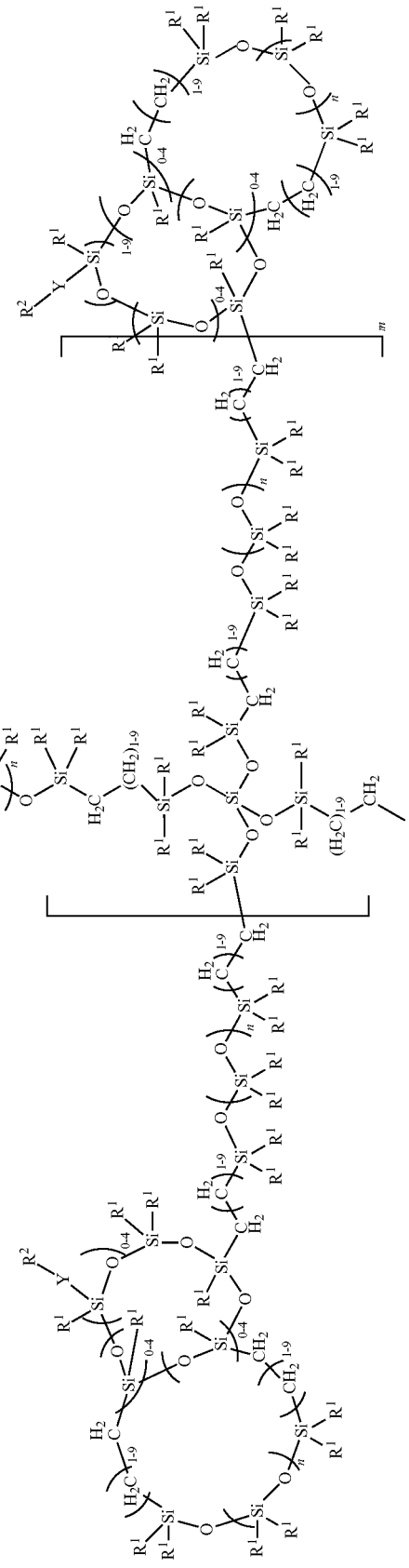

-continued
(16)
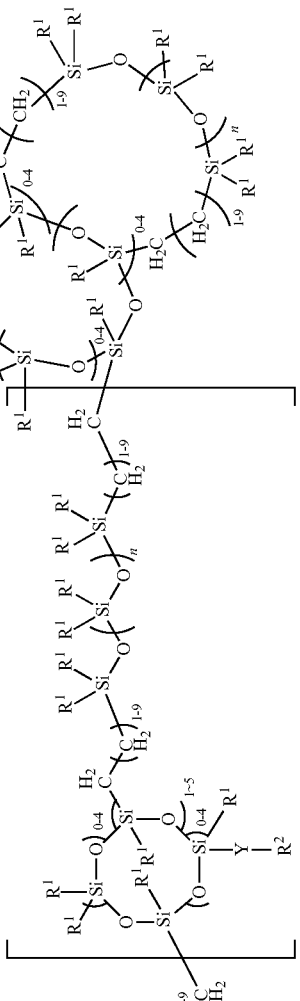
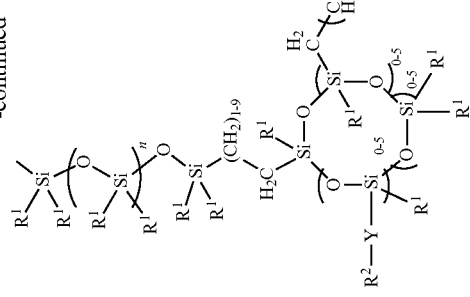
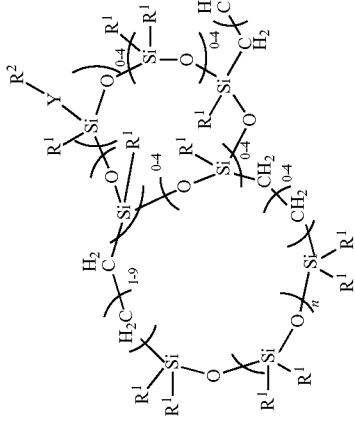

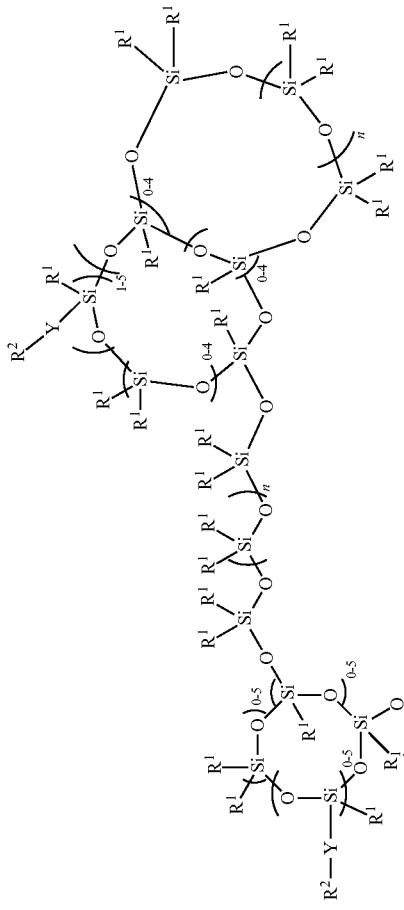
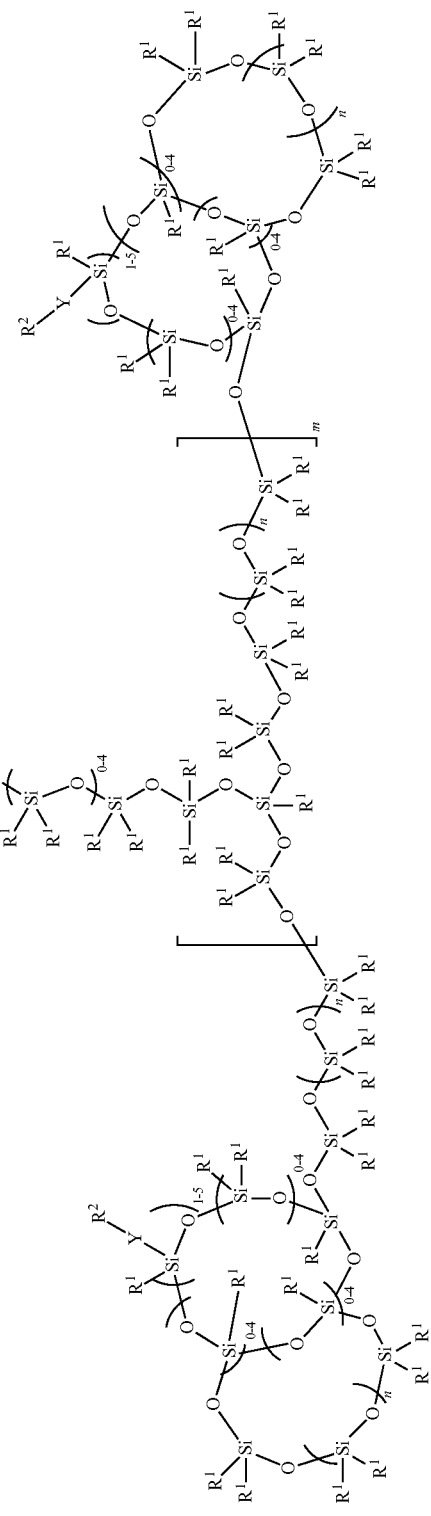
(17)

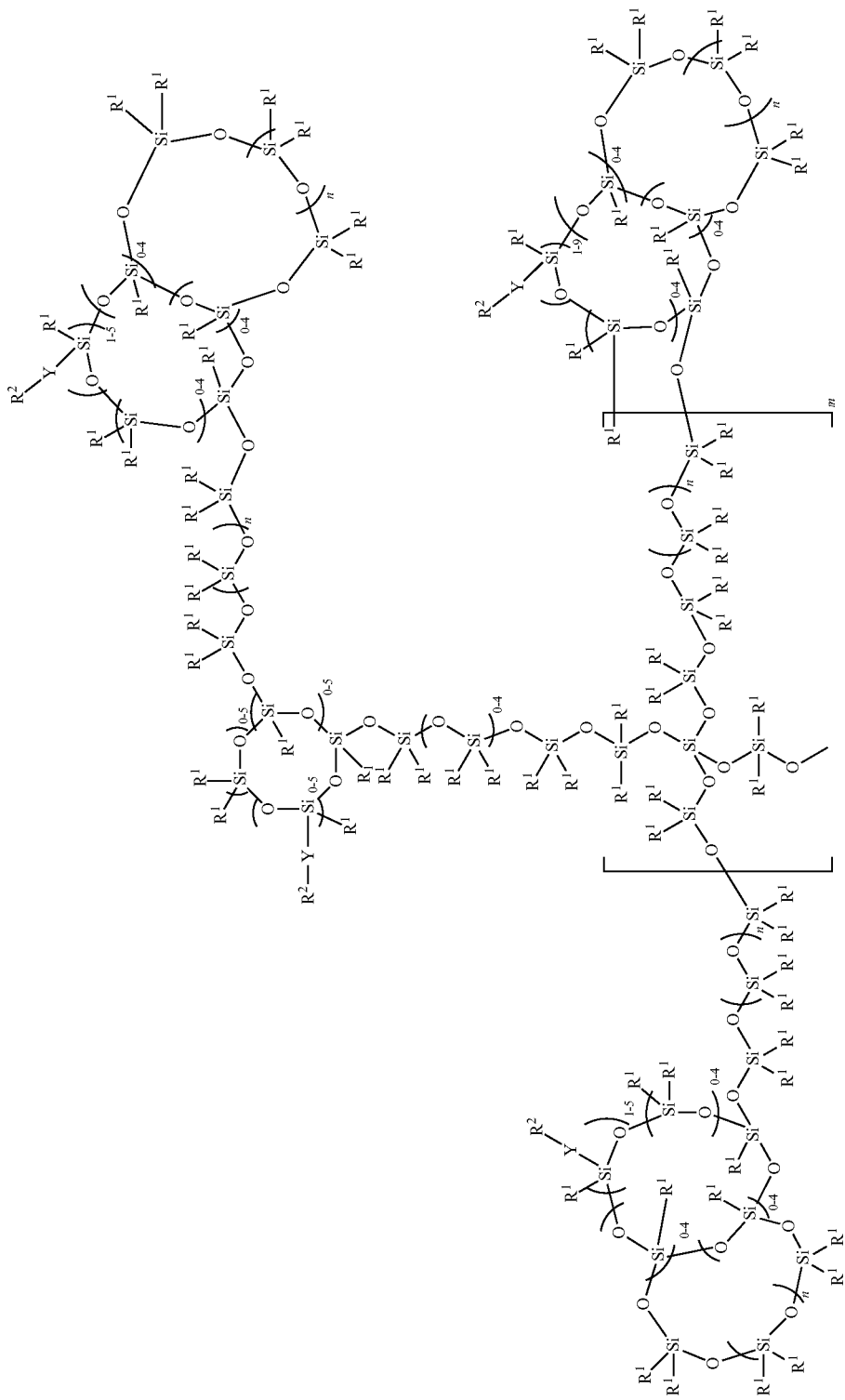

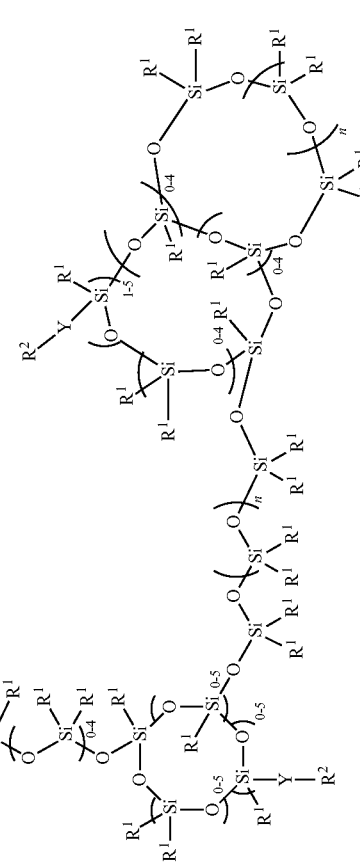
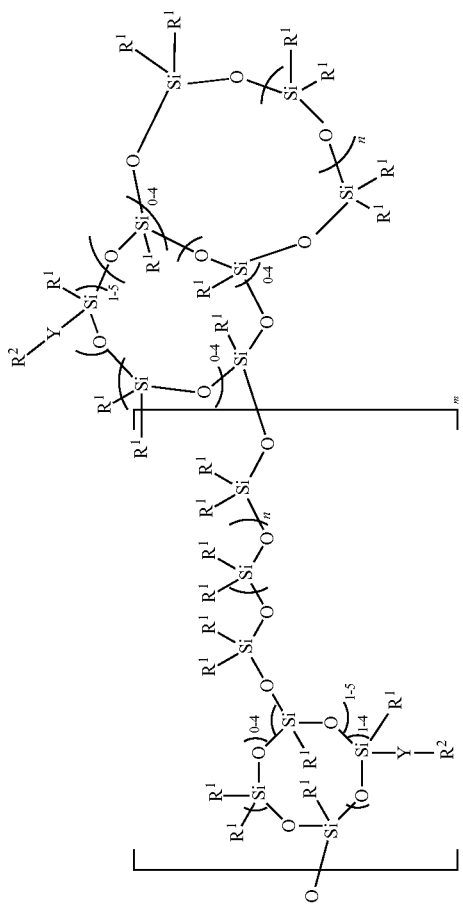
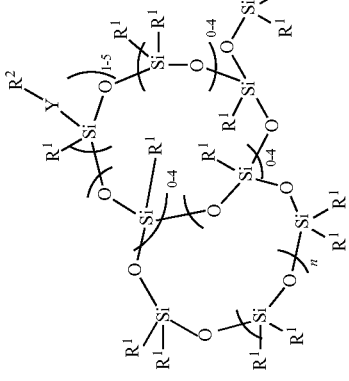
(19)

-continued
(20)
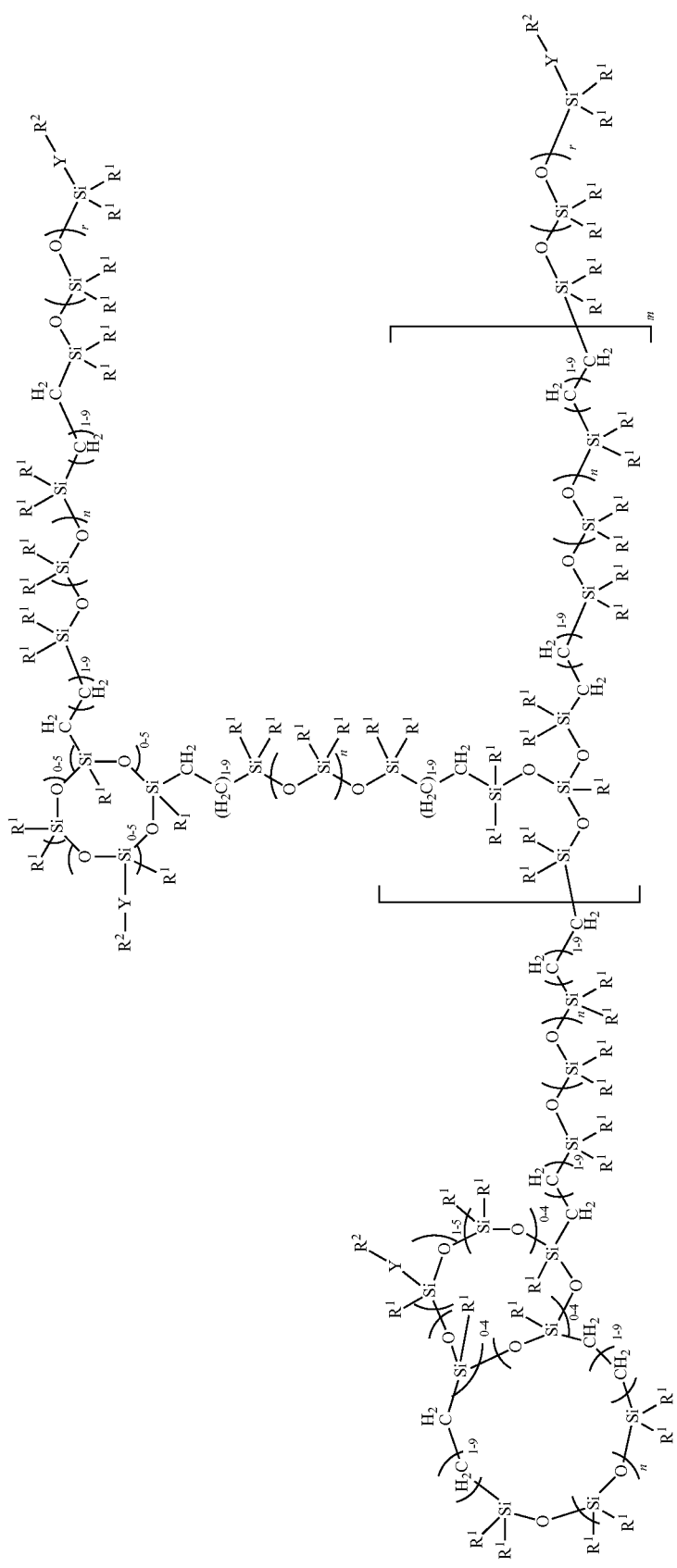

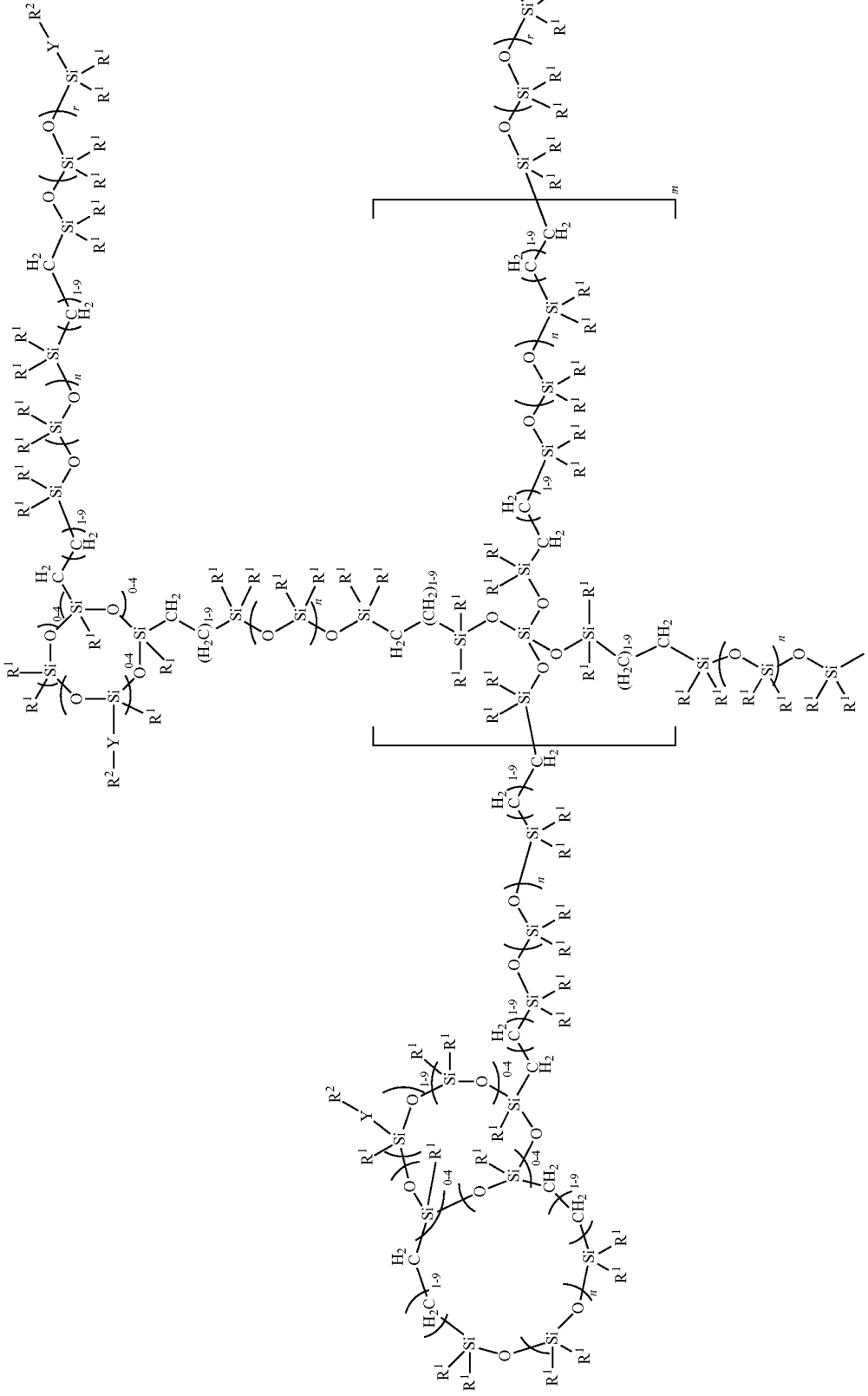

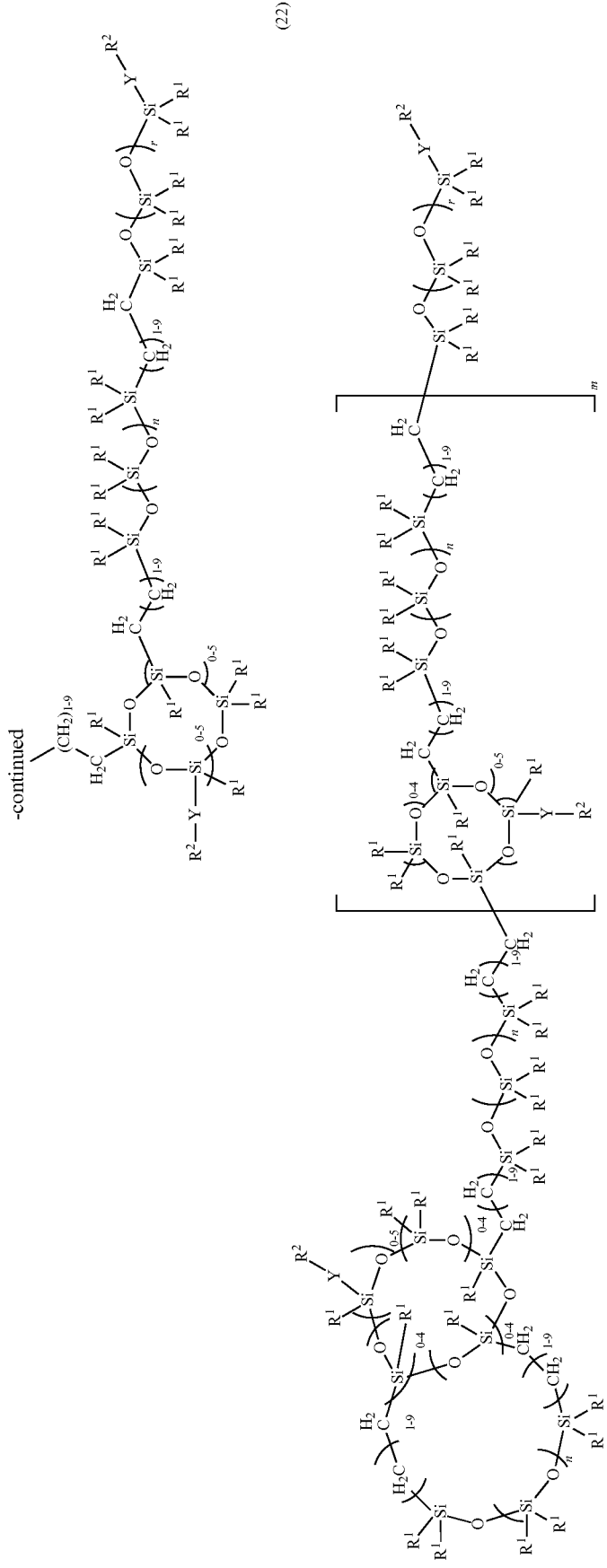
(22)

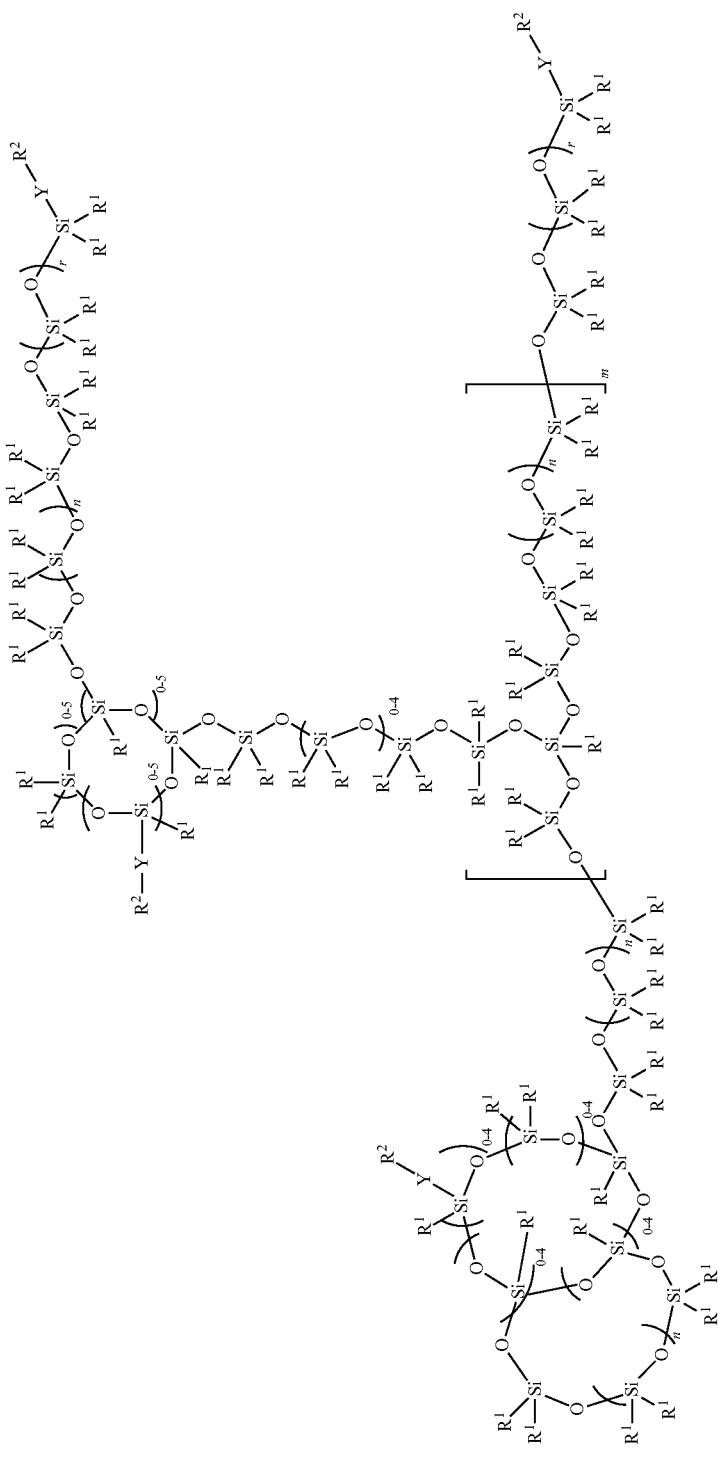

-continued
(24)
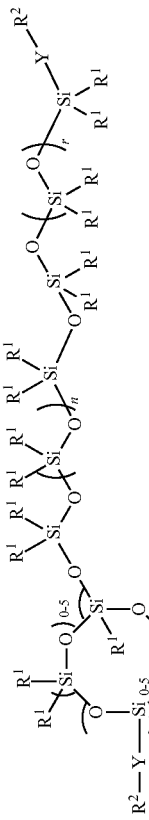
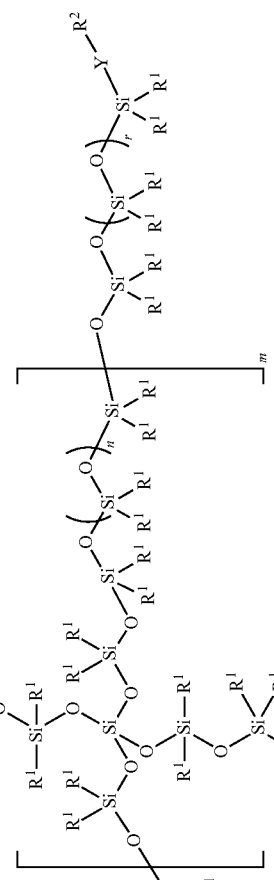
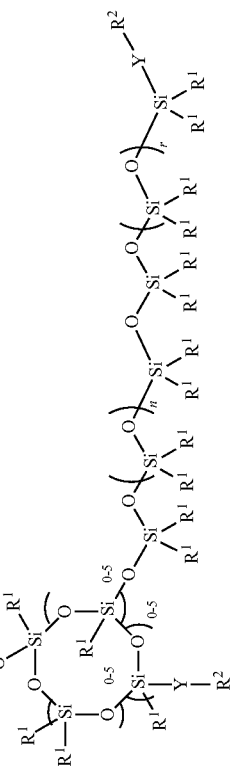
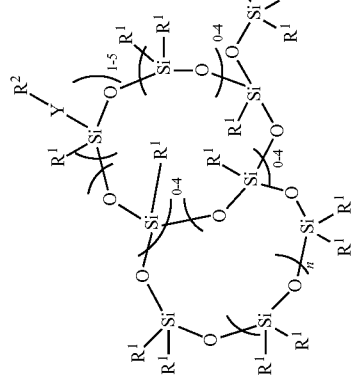

-continued
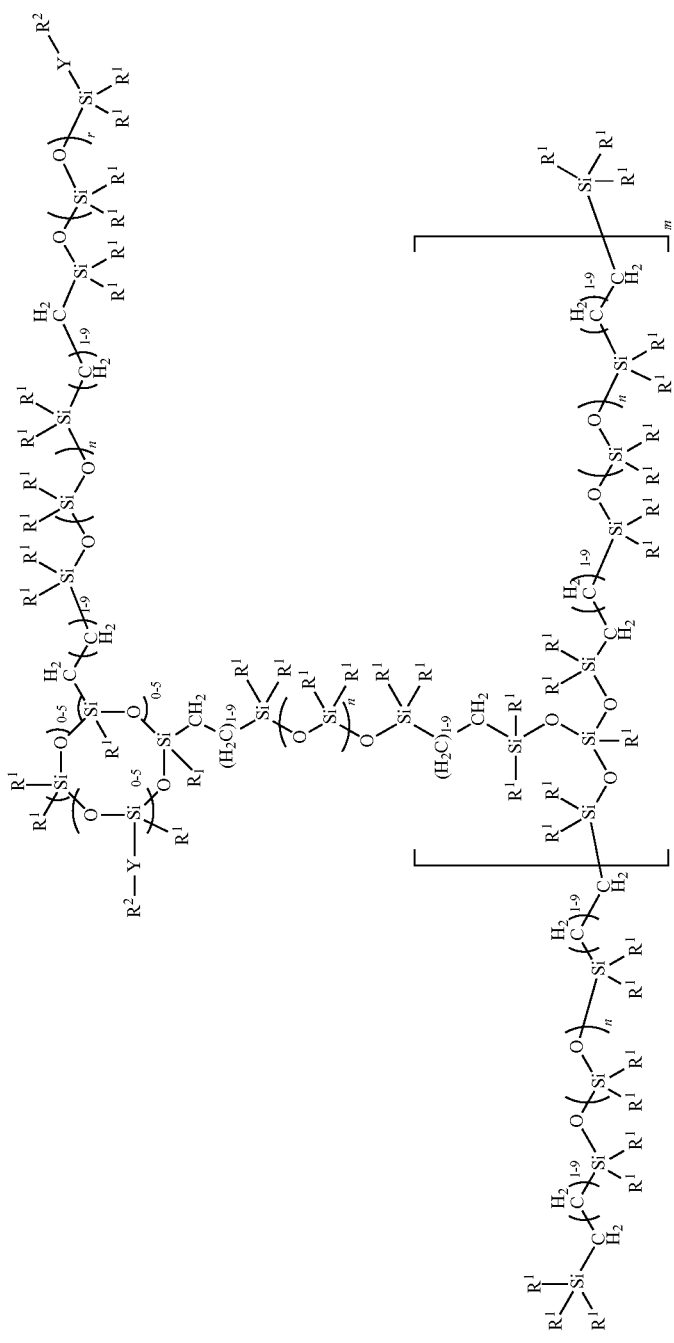
(25)

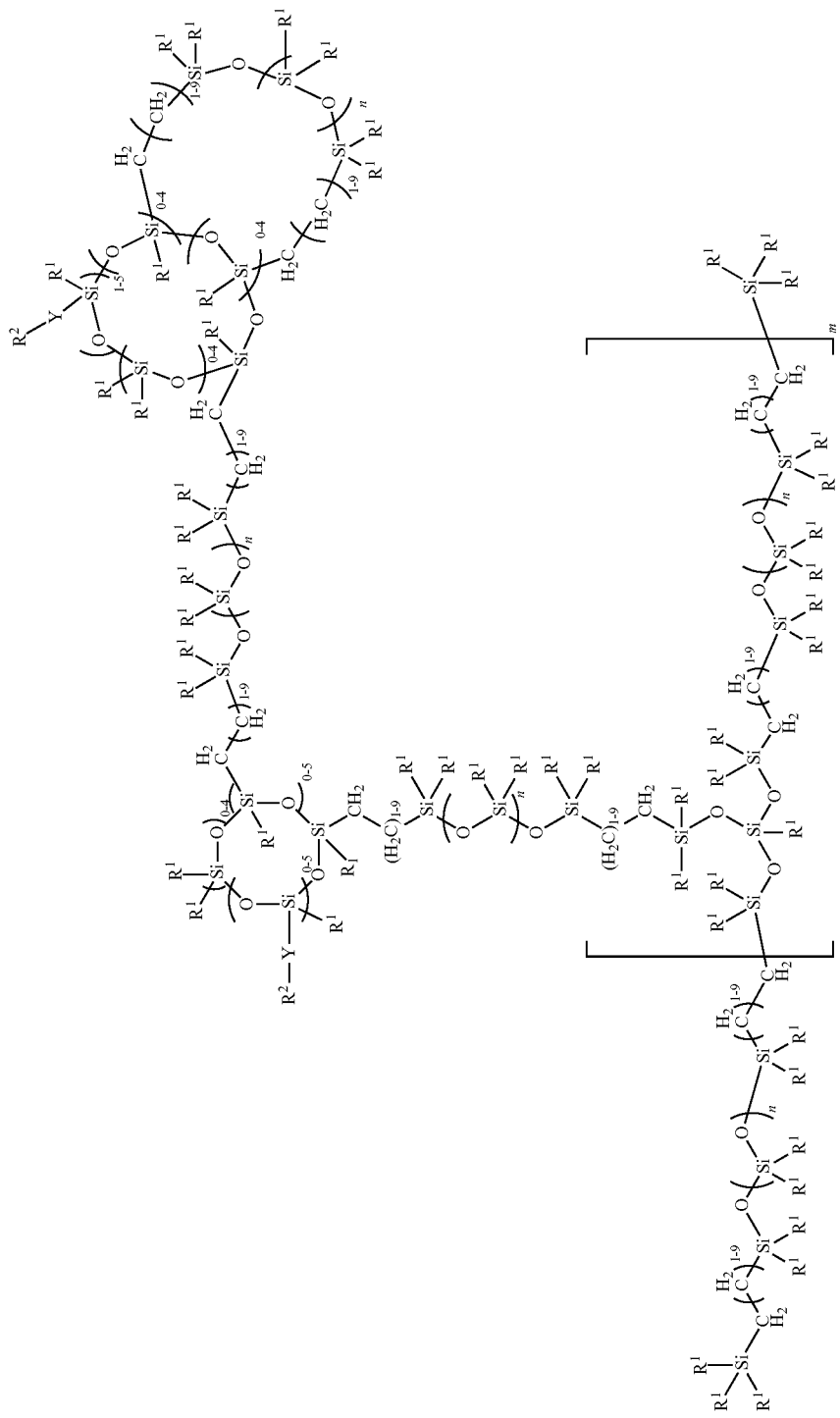

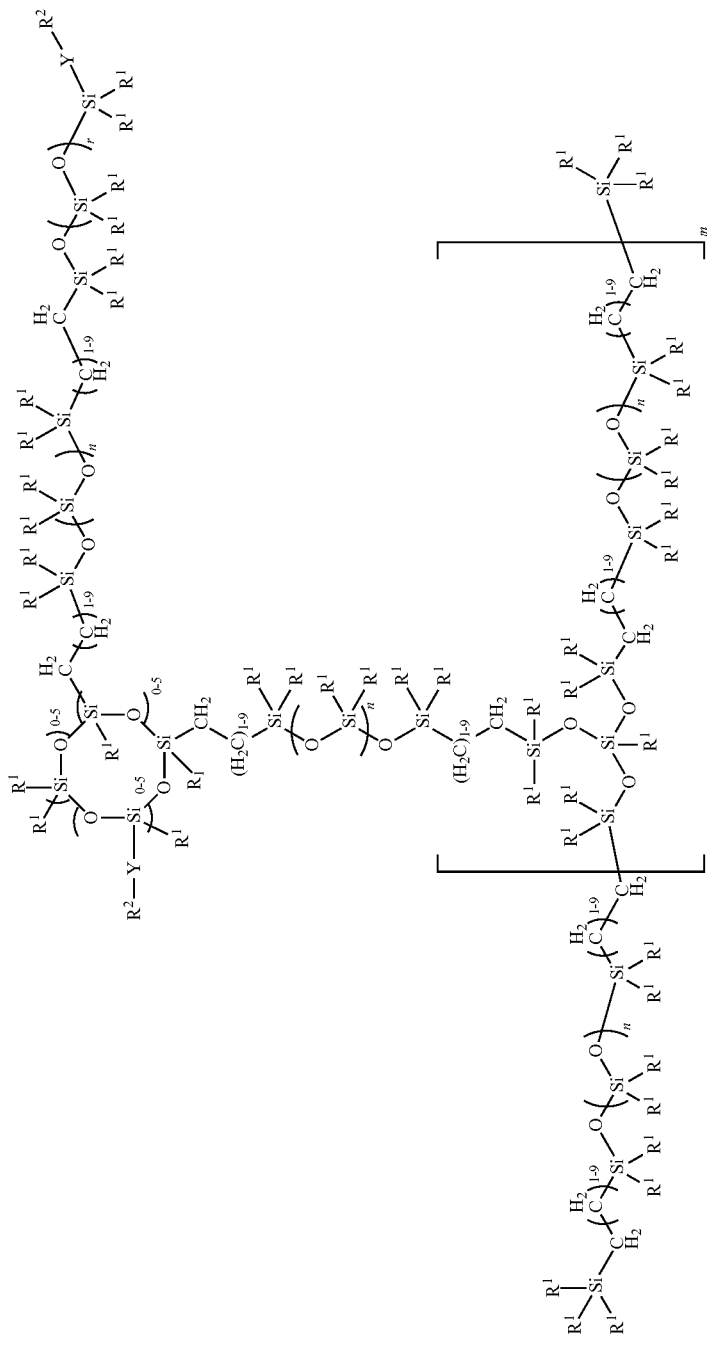
(29)

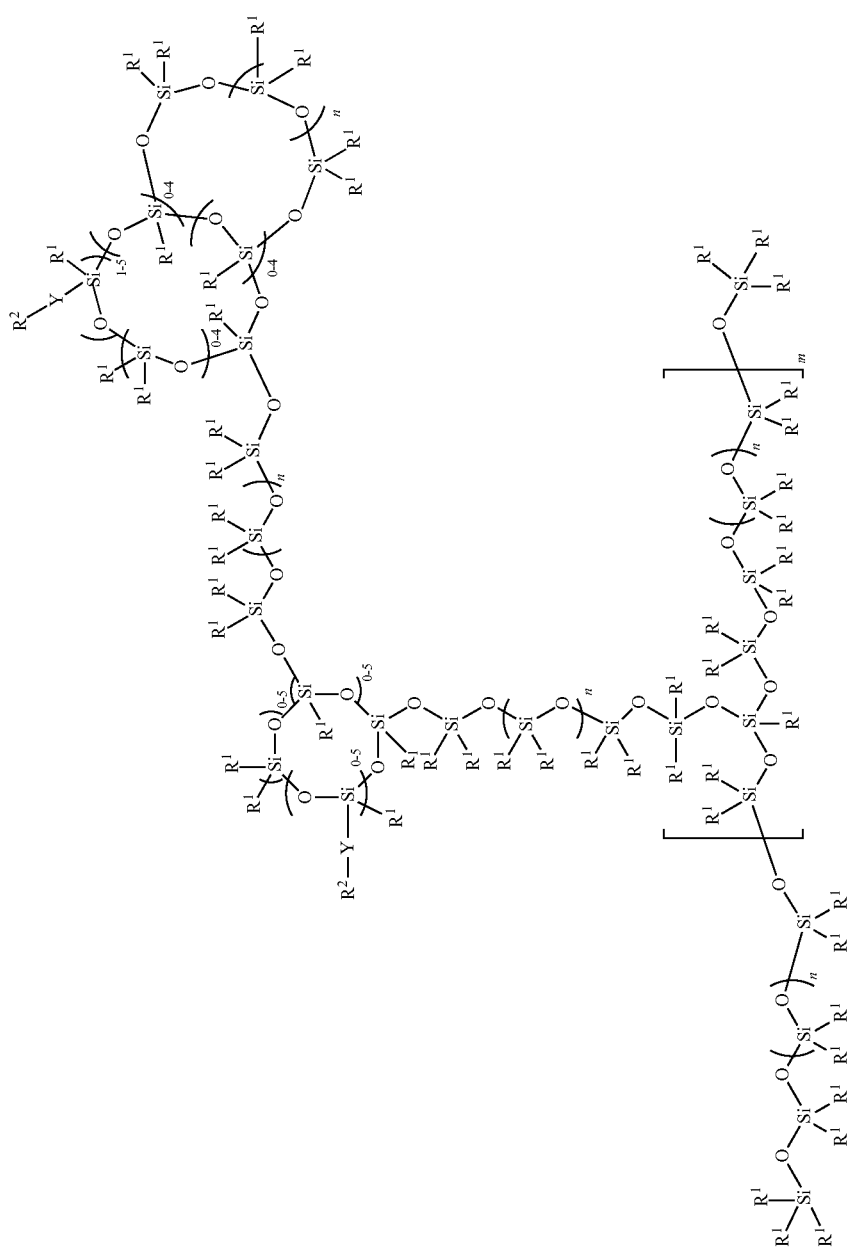

-continued
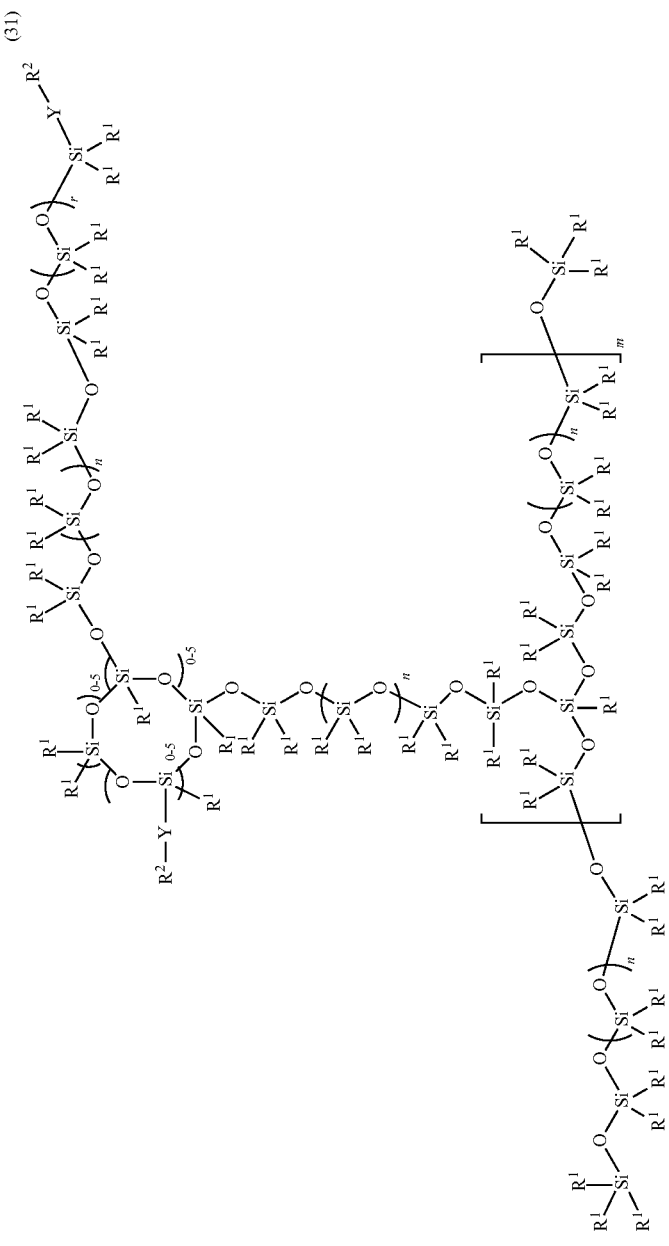
(31)

wherein $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group, in which the substituted $R^1$ is substituted with a hydroxy containing group, a cyano group, and/or a halogen containing group;

$R^2$ represents an unsaturated bond-containing group having 2 to 10 carbon atoms;

Y represents a divalent hydrocarbon group having 2 to 10 carbon atoms;

m represents an integer of 0 to 2000;

n represents an integer of 0 to 20; and r represents an integer of 0 to 20.

2. The organopolysiloxane according to claim 1, wherein formulae (14) through (25) and (28) through (31) have constitutional units F1, M1, and T in any combination of (i) F1 and M1, (ii) F1 and T, and (iii) F1, M1, and T, wherein the constitutional units F1, M1, and T are represented by general formulas (1), (2), and (3), respectively:

F1:

  (1)

M1:

  (2)

T:

  (3)

wherein X represents a divalent hydrocarbon group having 2 to 10 carbon atoms; and a, b, and c each independently represent an integer of 1 or larger, wherein F1 represents a unit constituting cyclic organopolysiloxane, and $R^2$ in the constitutional unit F1 represented by the general formula (1) is an acryloxy group or a methacryloxy group.

3. The organopolysiloxane according to claim 1, wherein the organopolysiloxane comprises a constitutional unit F2 represented by general formula (8) as constitutional units containing the $R^2$ moiety, provided that $R^{21}$ in formula (8) is included in the $R^2$ moiety:

F2:

  (8)

wherein $R^{21}$ represents an acryloxy group or a methacryloxy group, wherein

F2 represents a unit constituting chain organopolysiloxane.

4. The organopolysiloxane according to claim 1, comprising 0.1 to 100 parts by mass of cyclic organopolysiloxane represented by general formula (9) based on 100 parts by mass of the organopolysiloxane:

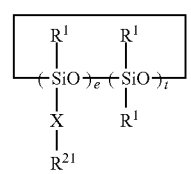  (9)

wherein $R^{21}$ represents an acryloxy group or a methacryloxy group;

X represents a divalent hydrocarbon group having 2 to 10 carbon atoms;

e represents an integer of 1 or larger;

f represents an integer of 0 or larger; and e+f represents an integer of 3 to 20.

5. The organopolysiloxane according to claim 1, comprising 0.01 to 1000 parts by mass of a compound represented by general formula (10) based on 100 parts by mass of the organopolysiloxane:

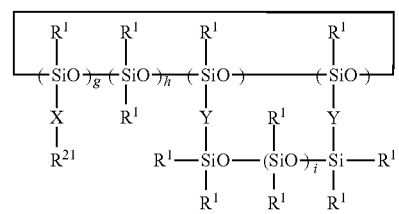  (10)

wherein $R^{21}$ represents an acryloxy group or a methacryloxy group;

X represents a divalent hydrocarbon group having 2 to 10 carbon atoms;

g represents an integer of 1 or larger;

h represents an integer of 0 or larger; and i represents an integer of 0 to 20.

6. The organopolysiloxane according to claim 1, wherein the organopolysiloxane contains cyclic organopolysiloxane represented by general formula (9) and a compound represented by general formula (10):

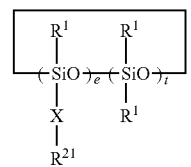  (9)

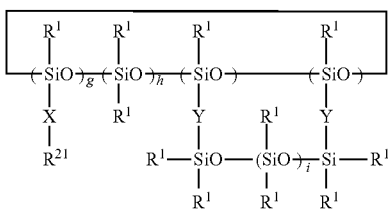

(10)

wherein
R²¹ represents an acryloxy group or a methacryloxy group;
X represents a divalent hydrocarbon group having 2 to 10 carbon atoms;
e represents an integer of 1 or larger;
f represents an integer of 0 or larger;
e+f represents an integer of 3 to 20;
g represents an integer of 1 or larger;
h represents an integer of 0 or larger; and
i represents an integer of 0 to 20,
wherein a ratio ([WB]/[WA]) of a content [WB] of the compound represented by the general formula (10) to a content [WA] of the compound represented by the general formula (9) is 0.1 or larger and 20.0 or smaller, the ratio being calculated according to formula (III) from peak intensity obtained in measurement by matrix-assisted laser desorption/ionization time-of-flight mass spectrometry:

$$[WB]/[WA] = \frac{\text{Intensity of a peak corresponding to the total sum of the mass of the structure of the general formula (10) and the mass 23 of sodium}}{\text{Intensity of a peak corresponding to the total sum of the mass of the structure of the general formula (9) and the mass 23 of sodium}}.$$ (III)

7. The organopolysiloxane according to claim 1, wherein $R^1$ is an alkyl group having 1 to 10 carbon atoms.

8. The organopolysiloxane according to claim 7, wherein $R^1$ is a methyl group.

9. The organopolysiloxane according to claim 1, wherein $R^2$ comprises an acryloxy group or a methacryloxy group, wherein the acryloxy group or the methacryloxy group has a functional group equivalent weight of 210 to 2100 g/mol.

10. The organopolysiloxane according to claim 1, wherein the organopolysiloxane has a weight-average molecular weight of 700 to 5000000 and a viscosity of 50 to 1000000 mPa·s at 25° C.

11. A method for producing organopolysiloxane according to claim 1, comprising the step of performing the addition reaction of
hydrogen polysiloxane (a1) represented by general formula (11):

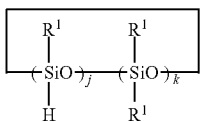

(11)

wherein $R^1$ represents any selected from the group consisting of a substituted or unsubstituted alkyl group having 1 to 10 carbon atoms, a substituted or unsubstituted cycloalkyl group having 3 to 10 carbon atoms, a substituted or unsubstituted aryl group, and a substituted or unsubstituted aralkyl group;
j represents an integer of 1 or larger;
k represents an integer of 0 or larger; and
j+k represents an integer of 3 to 20,
optional hydrogen polysiloxane (a2) having one or more hydrogen atom(s) directly bonded to silicon atom(s),
i) vinyl group-containing organopolysiloxane (b1) having two or more vinyl groups directly bonded to silicon atoms, or polysiloxane (b2) having two or more hydroxy groups directly bonded to silicon atoms, and
ii) an organic compound (c) having two or more unsaturated bonds in one molecule in the presence of a hydrosilylation reaction catalyst (d).

12. The method for producing organopolysiloxane according to claim 11, wherein the step of performing the addition reaction comprises the steps of:
preparing a reaction solution containing
the hydrogen polysiloxane (a1) represented by the general formula (11), and the optional hydrogen polysiloxane (a2) having one or more hydrogen atom(s) directly bonded to silicon atom(s); and
the vinyl group-containing organopolysiloxane (b1) having two or more vinyl groups directly bonded to silicon atoms, and the organic compound (c) having two or more unsaturated bonds in one molecule; or
the polysiloxane (b2) having two or more hydroxy groups directly bonded to silicon atoms, and the organic compound (c) having two or more unsaturated bonds in one molecule; and
adding the hydrosilylation reaction catalyst (d) to the reaction solution.

13. The method for producing organopolysiloxane according to claim 11, wherein the step of performing the addition reaction comprises, in order, the steps of:
preparing a reaction solution containing
the hydrogen polysiloxane (a1) represented by the general formula (11), the optional hydrogen polysiloxane (a2) having one or more hydrogen atom(s) directly bonded to silicon atom(s), and the organic compound (c) having two or more unsaturated bonds in one molecule;
adding the hydrosilylation reaction catalyst (d) to the reaction solution to form an adduct of the hydrogen polysiloxane (a1) represented by the general formula (11), the optional hydrogen polysiloxane (a2) having one or more hydrogen atom(s) directly bonded to silicon atom(s), and the organic compound (c) having two or more unsaturated bonds in one molecule; and
adding, to the reaction solution, the vinyl group-containing diorganopolysiloxane (b1) having two or more vinyl groups directly bonded to silicon atoms or the polysiloxane (b2) having two or more hydroxy groups directly bonded to silicon atoms.

14. A curable resin composition comprising
100 parts by mass of the organopolysiloxane according to claim 1, and
0.5 to 10 parts by mass of a thermal radical generator.

15. A curable resin composition comprising
100 parts by mass of the organopolysiloxane according to claim 1, and
0.5 to 20 parts by mass of a photo-radical generator.

16. The curable resin composition according to claim 14, further comprising 0.1 to 10 parts by mass of a silane coupling agent based on 100 parts by mass of the organopolysiloxane according to claim 1.

17. The curable resin composition according to claim 14, further comprising 0.001 parts by mass or less of a hydrosilylation reaction catalyst (d) based on 100 parts by mass of the organopolysiloxane.

18. The curable resin composition according to claim 14, further comprising 0.1 to 500 parts by mass of an inorganic oxide based on 100 parts by mass of the organopolysiloxane.

19. A sealing material for optical semiconductors, comprising a curable resin composition according to claim 14.

20. A die bonding material for optical semiconductors, comprising a curable resin composition according to claim 14.

21. A coating material comprising a curable resin composition according to claim 14.

22. A curable resin composition for nanoimprint, comprising a curable resin composition according to claim 14.

23. An ink comprising a curable resin composition according to claim 14 and a colorant.

24. An optical semiconductor package obtained by molding a sealing material for optical semiconductors according to claim 19.

25. The organopolysiloxane according to claim 1, wherein formulae (14) through (25) and (28) through (31) have constitutional units F1, M1, and T in any combination of (i) F1 and M1,
(ii) F1 and T, and
(iii) F1, M1, and T, wherein the constitutional units F1, M1, and T are represented by general formulas (1), (2), and (3), respectively:

F1:

M1:

T:

wherein X represents a divalent hydrocarbon group having 2 to 10 carbon atoms; and a, b, and c each independently represent an integer of 1 or larger, wherein F1 represents a unit constituting cyclic organopolysiloxane, and a, b, and c in the general formulas (1) to (3) satisfy formula (I):

$$0.1 \leq a/(b+c) \leq 5 \quad (I).$$

26. The organopolysiloxane according to claim 1, wherein the organopolysiloxane is represented by the formula (16).

27. The organopolysiloxane according to claim 1, wherein each of m, n, and r represents an integer larger than 0.

* * * * *